(12) United States Patent
Flom

(10) Patent No.: US 11,974,736 B2
(45) Date of Patent: May 7, 2024

(54) METHODS AND DEVICES FOR ACCESSING AND RETRACTING A CAPSULE OF A JOINT

(71) Applicant: Stryker Corporation, Kalamazoo, MI (US)

(72) Inventor: James Flom, Redwood City, CA (US)

(73) Assignee: Stryker Corporation, Kalamazoo, MI (US)

(*) Notice: Subject to any disclaimer, the term of this patent is extended or adjusted under 35 U.S.C. 154(b) by 21 days.

(21) Appl. No.: 17/317,451

(22) Filed: May 11, 2021

(65) Prior Publication Data
US 2021/0338221 A1    Nov. 4, 2021

Related U.S. Application Data

(63) Continuation of application No. 16/235,057, filed on Dec. 28, 2018, now Pat. No. 11,000,266, which is a continuation of application No. 15/620,901, filed on Jun. 13, 2017, now Pat. No. 10,166,020, which is a continuation of application No. 14/143,951, filed on
(Continued)

(51) Int. Cl.
| | |
|---|---|
| *A61B 17/02* | (2006.01) |
| *A61B 17/34* | (2006.01) |
| *A61B 34/00* | (2016.01) |
| *A61B 17/00* | (2006.01) |
| *A61B 17/04* | (2006.01) |
| *A61B 17/32* | (2006.01) |
| *A61B 18/00* | (2006.01) |

(52) U.S. Cl.
CPC ........ *A61B 17/025* (2013.01); *A61B 17/0218* (2013.01); *A61B 17/3417* (2013.01); *A61B 34/73* (2016.02); *A61B 2017/00637* (2013.01); *A61B 2017/0225* (2013.01); *A61B 2017/0275* (2013.01); *A61B 2017/0409* (2013.01); *A61B 2017/0417* (2013.01); *A61B 2017/320048* (2013.01); *A61B 2017/3488* (2013.01); *A61B 2018/00273* (2013.01); *A61B 2018/00279* (2013.01)

(58) Field of Classification Search
CPC .............. A61B 17/025; A61B 17/0281; A61B 2017/0275
See application file for complete search history.

(56) References Cited

U.S. PATENT DOCUMENTS

| | | |
|---|---|---|
| 4,741,330 A | 5/1988 | Hayhurst |
| 5,250,055 A | 10/1993 | Moore et al. |
| (Continued) | | |

*Primary Examiner* — Nicholas W Woodall
(74) *Attorney, Agent, or Firm* — Pandiscio & Pandiscio

(57) ABSTRACT

Devices and methods are disclosed herein for accessing the hip joint. A first device can be securely attached to the capsule of a joint. The first device can tent the capsule to increase the volume of the peripheral compartment. A second device can be biased against the first device to pierce the tented capsule and create a portal. Devices and methods are also disclosed herein for distending the capsule of a joint. A distention device may access a portal established within the capsule. The distention device can expand the capsule by applying an expansive force within the peripheral compartment. The distention device can maintain distention of the peripheral compartment while other devices access the joint.

24 Claims, 65 Drawing Sheets

Related U.S. Application Data

Dec. 30, 2013, now Pat. No. 9,675,336, which is a continuation of application No. 12/961,213, filed on Dec. 6, 2010, now Pat. No. 8,617,167.

(60) Provisional application No. 61/266,785, filed on Dec. 4, 2009.

(56) References Cited

U.S. PATENT DOCUMENTS

| | | | |
|---|---|---|---|
| 5,407,427 A * | 4/1995 | Zhu | A61B 17/34 604/26 |
| 5,906,210 A | 5/1999 | Herbert | |
| 6,165,184 A | 12/2000 | Verdura et al. | |
| 6,436,098 B1 * | 8/2002 | Michelson | A61B 17/025 623/908 |
| 6,488,691 B1 | 12/2002 | Carroll et al. | |
| 6,656,182 B1 | 12/2003 | Hayhurst | |
| 6,953,480 B2 | 10/2005 | Mears et al. | |
| 7,244,273 B2 | 7/2007 | Pedersen et al. | |
| 8,361,112 B2 | 1/2013 | Carroll, II et al. | |
| 8,617,167 B2 | 12/2013 | Weisel et al. | |
| 8,726,909 B2 * | 5/2014 | Cox | A61B 17/29 606/139 |
| 9,622,779 B2 | 4/2017 | Horton et al. | |
| 9,675,336 B2 | 6/2017 | Weisel et al. | |
| 2009/0018594 A1 * | 1/2009 | Laufer | A61B 17/0401 607/3 |
| 2009/0312807 A1 | 12/2009 | Boudreault et al. | |
| 2010/0160939 A1 * | 6/2010 | Braido | A61B 17/32053 606/170 |
| 2011/0040154 A1 | 2/2011 | Reznik | |
| 2011/0144442 A1 | 6/2011 | Farrell et al. | |

* cited by examiner (SECTION F-F)

(SECTION F-F)

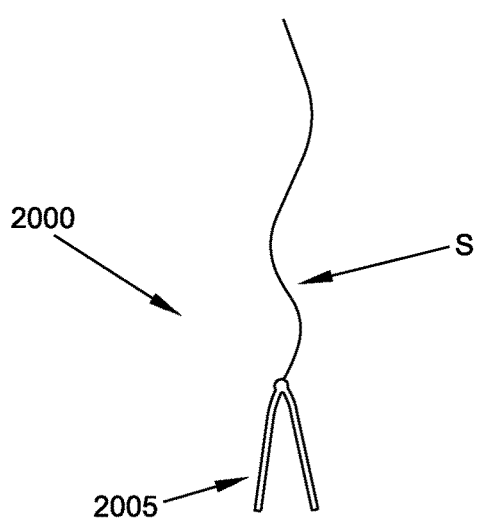
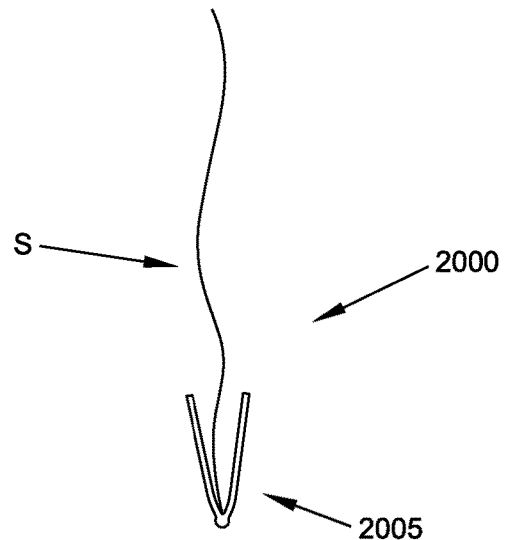
FIG. 28A                FIG. 28B
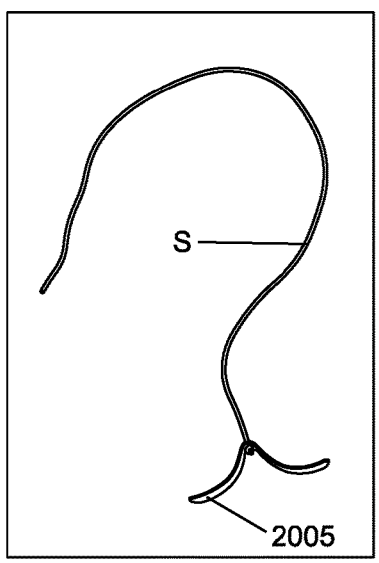
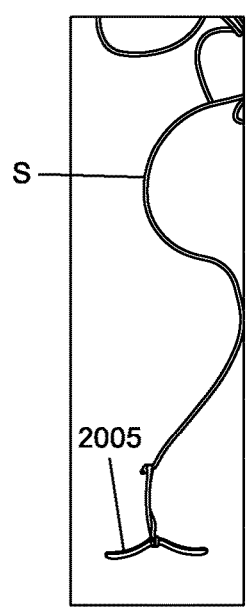
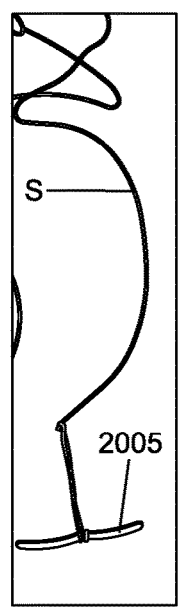
FIG. 28C          FIG. 28D          FIG. 28E

SIDE VIEW

FRONT VIEW

CROSS-SECTIONAL VIEWS

METHODS AND DEVICES FOR ACCESSING AND RETRACTING A CAPSULE OF A JOINT

REFERENCE TO PENDING PRIOR PATENT APPLICATIONS

This patent application is a continuation of pending prior U.S. patent application Ser. No. 16/235,057, filed Dec. 28, 2017 by Stryker Corporation for METHODS AND DEVICES FOR ACCESSING AND RETRACTING A CAPSULE OF A JOINT, which patent application is a continuation of prior U.S. patent application Ser. No. 15/620,901, filed Jun. 13, 2017 by Pivot Medical, Inc. for METHODS AND DEVICES FOR ACCESSING AND RETRACTING A CAPSULE OF A JOINT, which patent application is a continuation of prior U.S. patent application Ser. No. 14/143,951, filed Dec. 30, 2013 by Pivot Medical, Inc. for METHODS AND DEVICES FOR ACCESSING AND RETRACTING A CAPSULE OF A JOINT, which in turn is a continuation of prior U.S. patent application Ser. No. 12/961,213, filed Dec. 6, 2010 by Thomas Weisel et al. for METHODS AND DEVICES FOR ACCESSING AND RETRACTING A CAPSULE OF A JOINT, which patent application claims benefit of prior U.S. Provisional Patent Application Ser. No. 61/266,785, filed Dec. 4, 2009 by Hanson S. Gifford et al. for METHODS AND DEVICES TO ACCESS A CAPSULE OF A JOINT.

The five (5) above-identified patent applications are hereby incorporated herein by reference.

FIELD OF THE INVENTION

The present invention relates to medical devices and methods for accessing a joint, and more specifically to devices and methods for providing minimally invasive access into the hip joint.

BACKGROUND OF THE INVENTION

Obtaining arthroscopic access into orthopedic joints to perform surgical procedures can be extremely challenging. This is particularly true of the hip joint, which has two tissue barriers that must be crossed in order to gain access to the inner part of the joint. The outer barrier is known as the capsule. a series of tight overlapping ligaments surrounding the joint, effectively sealing off the hip joint from the remainder of the body. The area within the capsule is known as the peripheral compartment.

Within the peripheral compartment, the joint is fluidly sealed by a skirt-like tissue known as the labrum which is attached to the acetabular rim and hugs tightly around the base of the femoral head. The labrum femoral head interface creates a vacuum seal within the joint which helps to hold the femoral head tightly within the acetabulum. In order to gain access to the central compartment (i.e., the portion of the joint within the labrum lying between the femoral head and acetabulum) the seal of the labrum must be broken and instruments then introduced into the very narrow opening between the bottom edge of the labrum and femoral head.

In arthroscopic surgery, access to the peripheral compartment is typically obtained through the use of elongate tubular devices (e.g., arthroscopic portals or cannulas), which are inserted through the patient's skin and through the ligaments of the capsule to provide a tunnel or lumen through which instruments may be introduced. Multiple access portals are typically employed, with one access portal being used for visualization (e.g., for placement of an arthroscope), and the remaining portal(s) being available for the introduction of other instruments.

However, the creation of access portals can be problematic. For one thing, the patient's anatomy (e.g., bone, blood vessels, nerves, etc.) can greatly restrict the possible portal locations. Furthermore, some hip structures (e.g., the articular cartilage on the femoral head, the articular cartilage on the acetabular cup, etc.) can be quite delicate, thereby requiring great precision when forming the access portal so as to avoid damaging delicate structures. Additionally, some of the intervening tissue (e.g., the joint capsule) can be quite tough, thus requiring substantial force to penetrate the tissue, and thereby raising the danger of accidental plunging as an access tool breaks through the intervening tissue. Such accidental plunging increases the risk of inadvertently damaging delicate joint structures (e.g. articular cartilage).

Due to the numerous difficulties and concerns associated with forming an access portal, surgeons have traditionally resorted to a multi-step procedure for forming the access portal.

More particularly, surgeons have traditionally first passed a small needle (sometimes referred to as an access needle) down to the interior of the hip joint. This is generally done by first using external anatomical landmark and tactile feedback for needle guidance; then, as the sharp tip of access needle enters the capsule of the joint and approaches delicate structures (e.g. articular cartilage), fluoroscopy is used to carefully direct final needle placement. Inexperienced surgeons, or experienced surgeons dealing with particularly problematic cases, may also use fluoroscopy during the earlier stages of needle placement.

Next, a guidewire is placed through the lumen of the access needle, then the access needle is removed. Next, the tissue surrounding the guidewire is opened laterally by passing a series of tissue dilators over the guidewire. These dilators progressively increase in diameter so as to dilate the tissue disposed between the skin and the interior of the joint.

Once the opening from the top surface of the skin down to the interior of the joint has been established, a tubular liner (sometimes referred to as an "access cannula") is inserted over the guidewire, and the guidewire may be withdrawn from the joint. This access cannula holds the incision open and provides a surgical pathway (or "corridor") from the top surface of the skin down to the interior of the hip joint, thereby enabling instrumentation (e.g., arthroscopes, surgical instruments, etc.) to be passed through the central lumen of the access cannula so as to reach the remote surgical site within the joint.

This multi-step process requires substantial effort on the part of the surgeon, increases the instrumentation necessary for the procedure, and extends the duration of the procedure.

Surgeons have also created portals by inserting long spinal needles into the joint under fluoroscopic guidance In order to avoid damaging the cartilage of the hip joint with the needle, the femur is distracted from the pelvis by approximately 5 to 10 millimeters to create a gap between the femoral head and the acetabulum of the pelvis. The needle is accordingly guided into the gap.

Hip distraction typically requires the use a distraction table, a surgical table that includes a post placed against the patient's perineum and a tensioning device which fastens to the patient's foot or ankle and allows high forces (e.g., 50 to 70 pounds) to be exerted on the patient's leg to distract the femur and create space within the joint. These tables not only are large, cumbersome and expensive, but they limit the mobility of the joint during the procedure and frequently produce complications such as nerve damage.

Even with use of a distraction table, damage to the cartilage and other joint tissue may be difficult to avoid. The capsule surrounding the hip joint is significantly denser and "tougher" than tissue externally surrounding the capsule. Accordingly, a high amount of force is required to pierce the capsule, even with use of a sharp needle. However, the capsule is relatively thin, 2 to 15 millimeters, and the high amount of force required to pierce it can inadvertently cause a needle to uncontrollably "pop" through the capsule and damage tissue beyond. The space within the peripheral compartment is also relatively small for use with arthroscopic devices. Accordingly, several portals must be created to enable proper access to the joint. Each time a portal is created, the risk of unintended harm is increased.

Methods and devices have been proposed for accessing the hip joint without using a distraction table. For example, commonly assigned U.S. patent application Ser. No. 12/483, 446, filed Jun. 12, 2009, entitled "Methods and Apparatus for Joint Distraction", the entirety of which is incorporated by reference herein, discloses various internal distraction devices for distracting the hip and other joints. These devices use balloons or other expandable features placed within the central compartment to displace the femoral head further away from the acetabulum in order to allow access for surgical instruments. While such devices eliminate the need for a distraction table, challenges may still be encountered in introducing these devices into the peripheral and central compartments. Further, even where a conventional distraction table is used, the placement of portals and the introduction of instruments into the peripheral and central compartments remain challenging.

On account of the foregoing, there is a substantial need for a simpler, faster and more convenient approach for creating an access portal to the interior of the hip joint.

More particularly, there is a substantial need for a new approach for deploying an access cannula into the interior of the hip joint.

There is also a substantial need for locking an access cannula so that its distal tip is constrained within the capsule of the hip joint so as to facilitate the insertion and removal of instruments.

In addition to the foregoing, there is also a significant need for creating additional workspace once access is gained to the interior of the hip joint, whereby to afford surgeons improved visualization at the surgical site and more room to maneuver.

SUMMARY OF THE INVENTION

These and other objects of the present invention are addressed by the provision and use of a novel method and apparatus for accessing a capsule of a joint.

More particularly, in one embodiment of the present invention, a capsule of a joint may be accessed by attaching a first device to the capsule of the joint. The capsule may then be distended by placing a second device into the capsule through a passage in the first device.

In another embodiment of the invention there is provided a system for creating a portal in a capsule of a joint. The system may include an elongated needle. The system may also include an elongated sheath with an inner surface. The inner surface may be diametrically sized to freely slide over the elongated needle, the elongated sheath including a plurality of grasping members coupled near a distal end thereof.

Yet another embodiment of the invention provides a method for accessing a capsule of a joint. A needle may be advanced to a capsule of a joint. A sheath may be advanced over the needle to the capsule, the sheath holding an expansion device. Grasping members of the expansion device may be engaged into the capsule to secure the expansion device to the capsule. The needle may be advanced through the capsule of the joint to create a penetration therein.

Yet another embodiment of the invention provides a system for creating a portal in a capsule of a joint. The system may include an elongated needle. The system may also include an elongated sheath with an inner surface. The inner surface diametrically may be sized to freely slide over the elongated needle. The system may also include an elongated expansion device, which may include a plurality of grasping members at one end of the expansion device, the expansion device may be radially constrained by the inner surface of the elongated sheath.

Yet another embodiment of the invention provides a system for creating a. portal in a capsule of a joint. The system may include an elongated needle. The system may also include an elongated sheath with an inner surface. The inner surface may be diametrically sized to freely slide over the elongated needle. The system may also include an elongated expansion device housed at the inner surface of the elongated sheath. The expansion device may have a plurality of grasping members at one end, the grasping members being biased radially inward. An inner shaft may be slidably disposed within the expansion device and sized to urge the grasping members towards radially inward when distally advanced.

Yet another embodiment of the invention provides a method for accessing a capsule of a joint. A needle may be advanced to a capsule of a joint. A sheath may be advanced over the needle to the capsule, a wall of the sheath holding grasping members constrained in a straightened configuration. The grasping members may be engaged into the capsule to secure the sheath to the capsule. The needle may be advanced through the capsule of the joint to create a penetration therein.

Yet another embodiment of the invention provides a system for creating a portal in a capsule of a joint. The system may include an elongated sheath with an inner diameter sized to freely slide over the elongated needle. The elongated sheath may include a wall with a plurality of pathways and including expandable zones between the pathways. A plurality of wires may be slidably housed within the plurality of pathways. The plurality of wires may include a plurality of hooks.

Yet another embodiment of the invention provides a method for accessing a capsule of a joint. A needle may be advanced to a capsule of a joint. A cannula may be advanced over the needle to the capsule. A first portion of the cannula may be maintained in place. A second portion of the cannula may be rotated with respect to the stationary first portion to engage grasping members of the expansion device into the capsule to secure the cannula to the capsule. The needle may be advanced through the capsule of the joint to create a penetration therein.

Yet another embodiment of the invention provides a system for accessing a capsule of a joint. The system may include an elongated inner tube including a. plurality of expandable hooks. An elongated outer tube may be rotatably engaged to the inner tube. The outer tube may include a plurality of slots. The plurality of expandable hooks may be slidably engaged with the plurality of slots.

Yet another embodiment of the invention provides a method for accessing a capsule of a joint. A capsule of a joint may be accessed. A cannula may be attached to the capsule of the joint. A penetration may be created in the capsule. The capsule may be distended using a distension device.

Yet another embodiment of the invention provides a system for creating a portal in a capsule of a joint. The system may include an elongated needle. An elongated cannula may be diametrically sized to freely slide over the elongated needle. The cannula may have a plurality of grasping members at one end of the expansion device. An elongated distension device may be moveably coupled to the elongated cannula.

Yet another embodiment of the invention provides a method for distending a capsule of a joint. A capsule of a joint may be accessed. A penetration through the capsule may be created. A delivery device holding a distention device maybe inserted into the penetration. The distention device may be deposited into the portal and removed from the delivery device. The distention device may be activated to expand within the capsule.

Yet another embodiment of the invention provides a system for distending a capsule of a joint. The system may include a piston device. The piston device may include first and second atraumatic bumpers. One atraumatic bumper may be attached to an end of the elongate body and the other to an end of the moveable shaft. The system may include an elongated applicator including a holding device removably coupled to one of the bumpers.

Yet another embodiment of the invention provides a method for distending a capsule of a joint. A capsule of a joint may be accessed. A first portal and a second portal may be created through the capsule. A magnetic end of a first flexible strap may be guided into first portal. A magnetic end of a second flexible strap may be guided into the second portal. The magnetic ends may couple within the capsule. Either the first or second strap may be withdrawn from the capsule to place a mid-portion of the other of the first or second strap within the capsule. The non-withdrawn first or second strap may be pulled from both portals to distend the capsule away from the joint.

Yet, another embodiment of the invention provides a system for distending a capsule of a joint. The system may include a first and second cannula. The system may also include a first and second elongated strap. Each strap may be sized to slide within the first and second cannula. Each strap may include a magnetic member attached at an end of each strap configured to magnetically attract the magnetic member on the other strap.

In one preferred form of the invention, there is provided a method for accessing a capsule of a joint, the method comprising:
 accessing a capsule of a joint;
 attaching a first device to the capsule of the joint;
 distending the capsule; and
 placing a second device into the capsule through a passage in the first device.

In another preferred form of the invention, there is provided a system for creating a portal in a capsule of a joint, the system comprising:
 an elongated needle; and
 an elongated sheath with an inner surface, the inner surface diametrically sized to freely slide over the elongated needle, the elongated sheath including a plurality of grasping members coupled near a distal end thereof.

In another preferred form of the invention, there is provided a method for accessing a capsule of a joint, the method comprising:
 advancing a needle to a capsule of a joint;
 advancing a sheath over the needle to the capsule, the sheath holding an expansion device;
 engaging grasping members of the expansion device into the capsule to secure the expansion device to the capsule; and
 advancing the needle through the capsule of the joint to create a penetration therein.

In another preferred form of the invention, there is provided a system for creating a portal in a capsule of a joint, the system comprising:
 an elongated needle;
 an elongated sheath with an inner surface, the inner surface diametrically sized to freely slide over the elongated needle; and
 an elongated expansion device including a plurality of grasping members at one end of the expansion device, the expansion device being radially constrained by the inner surface of the elongated sheath.

In another preferred form of the invention, there is provided a system for creating a portal in a capsule of a joint, the system comprising:
 an elongated needle;
 an elongated sheath with an inner surface, the inner surface diametrically sized to freely slide over the elongated needle;
 an elongated expansion device housed at the inner surface of the elongated sheath, the expansion device including a plurality of grasping members at one end, the grasping members being biased radially inward; and an inner shaft slidably disposed within the expansion device and sized to urge the grasping members radially outward when distally advanced.

In another preferred form of the invention, there is provided a method for accessing a capsule of a joint, the method comprising:
 advancing a needle to a capsule of a joint;
 advancing a sheath over the needle to the capsule, a wall of the sheath holding grasping members constrained in a straight configuration;
 engaging the grasping members into the capsule to secure the sheath to the capsule; and
 advancing the needle through the capsule of the joint to create a penetration therein.

In another preferred form of the invention, there is provided a system for creating a portal in a capsule of a joint, the system comprising:
 an elongated sheath with an inner diameter sized to freely slide over the elongated needle, the elongated sheath including a wall with a plurality of pathways and including expandable zones between the pathways; and
 a plurality of wires slidably housed within the plurality of pathways, the plurality of wires including a plurality of hooks.

In another preferred form of the invention, there is provided a method for accessing a capsule of a joint, the method comprising:
 advancing a needle to a capsule of a joint;
 advancing a cannula over the needle to the capsule;
 maintaining a first portion of the cannula in place;
 rotating a second portion of the cannula with respect to the stationary first portion to engage grasping members of the expansion device into the capsule so as to secure the cannula to the capsule; and
 advancing the needle through the capsule of the joint to create a penetration therein.

In another preferred form of the invention, there is provided a system for accessing a capsule of a joint, the system comprising:
an elongated inner tube including a plurality of expandable hooks; and
an elongated outer tube rotatably engaged to the inner tube, the outer tube including a plurality of slots, the plurality of expandable hooks being slidably engaged with the plurality of slots.

In another preferred form of the invention, there is provided a method for accessing a capsule of a joint, the method comprising:
accessing a capsule of a joint;
attaching a cannula to the capsule of the joint;
creating a penetration in the capsule; and
distending the capsule using a distension device.

In another preferred form of the invention, there is provided a system for creating a portal in a capsule of a joint, the system comprising:
an elongated needle;
an elongated cannula diametrically sized to freely slide over the elongated needle, the cannula including a plurality of grasping members at one end of the expansion device; and
an elongated distension device moveably coupled to the elongated cannula.

In another preferred form of the invention, there is provided a method for distending a capsule of a joint, the method comprising:
accessing a capsule of a joint;
creating a penetration through the capsule;
inserting a delivery device holding a distention device into the penetration;
depositing the distention device into the portal and removing the delivery device; and
activating the distention device to expand within the capsule.

In another preferred form of the invention, there is provided a system for distending a capsule of a joint, the system comprising:
a piston device comprising:
an elongate body, a moveable shaft extending from the elongate body;
first and second atraumatic bumpers, one atraumatic bumper being attached to an end of the elongate body and the other to an end of the moveable shaft; and
an elongated applicator, the elongated applicator including a holding device removably coupled to one of the bumpers.

In another preferred form of the invention, there is provided a method for distending a capsule of a joint, the method comprising:
accessing a capsule of a joint;
creating a first portal and a second portal through the capsule;
guiding a magnetic end of a first flexible strap into the first portal;
guiding a magnetic end of a second flexible strap into the second portal, the magnetic ends coupling within the capsule;
withdrawing either the first or second strap from the capsule to place a mid-portion of the other of the first or second strap within the capsule; and
pulling on the non-withdrawn first or second strap from both portals to distend the capsule away from the joint.

In another preferred form of the invention, there is provided a system for distending a capsule of a joint, the system comprising:
first and second cannulas; and
first and second elongated straps, each strap sized to slide within the first and second cannula, each strap including a magnetic member attached to an end of the strap configured to magnetically attract the magnetic member on the other strap.

In another preferred form of the invention, there is provided an apparatus for accessing the interior of a joint and creating additional work space within the interior of a joint, the apparatus comprising:
an elongated shaft having a distal end and a proximal end, and a lumen extending between the distal end and the proximal end; and
an elongated sleeve for disposition over the elongated shaft, the elongated sleeve having a distal end and a proximal end and a lumen extending between the distal end and the proximal end, wherein the distal end of the elongated shaft comprises an expandable collar.

In another preferred form of the invention, there is provided a method of accessing the interior of a joint and creating additional work space within the interior of a joint, the method comprising:
providing an apparatus comprising:
an elongated shaft having a distal end and a proximal end, and a lumen extending between the distal end and the proximal end; and
an elongated sleeve for disposition over the elongated shaft, the elongated sleeve having a distal end and a proximal end and a lumen extending between the distal end and the proximal end, wherein the distal end of the elongated shaft comprises an expandable collar;
passing the apparatus into the joint so that the distal end of the elongated sleeve is positioned on the interior of a capsule of a joint;
expanding the expandable collar; and
tenting the capsule so as to create additional work space within the capsule of the joint.

In another preferred form of the invention, there is provided an apparatus for retracting a capsule of a joint, the apparatus comprising:
a length of suture; and
an anchor attached to one end of the length of suture.

In another preferred form of the invention, there is provided a method of retracting a capsule of a joint, the method comprising:
providing a length of suture and an anchor attached to one end of the length of suture, wherein the anchor comprises a body which is configured to assume (i) a first, folded configuration when the body is in a stressed condition, and (ii) a second, straight configuration when the body is in an unstressed condition;
loading the suture and the anchor into a sheath so that the anchor assumes its first folding configuration;
passing the sheath into the capsule of a joint;
pushing the anchor through the sheath and into the capsule of the joint so that as the anchor passes into the joint, the anchor assumes its second, straight configuration;
positioning the anchor against the interior surface of the capsule; and
pulling the length of suture proximally so as to retract the capsule of the joint.

In another preferred form of the invention, there is provided an apparatus for retracting a capsule of a joint, the apparatus comprising:
an elongated rod having a proximal end and a distal end; and a retraction element disposed on the distal end of the elongated rod.

In another preferred form of the invention, there is provided a method of retracting a capsule of a joint, the method comprising:

providing an elongated rod having a proximal end and a distal end and a retraction element disposed on the distal end of the elongated rod;
wherein the retraction element comprises a pivoting distal end, and further wherein the pivoting distal end may be pivoted between (i) a first position in which the distal end is aligned with the longitudinal axis of the elongated shaft, and (ii) a second position in which the distal end extends at an angle to the longitudinal axis of the elongated rod;
pivoting the distal end of the elongated rod into the first position;
passing the elongated rod into the capsule of a joint so that the distal end of the elongated rod is positioned within the interior of the joint;
pivoting the distal end of the elongated rod into the second position;
positioning the distal end of the elongated rod against the interior of the capsule; and
pulling the elongated rod proximally so as to retract the capsule of the joint.

In another preferred form of the invention, there is provided a method of retracting a capsule of a joint, the method comprising:

providing an elongated rod having a proximal end and a distal end and a retraction element disposed on the distal end of the elongated rod;
wherein the retraction element comprises a projection, and further wherein the projection may be moved between (i) a first position in which the projection is aligned with the longitudinal axis of the elongated shaft, and (ii) a second position in which the projection extends at an angle to the longitudinal axis of the elongated rod;
moving the projection into the first position;
passing the elongated rod into the capsule of a joint so that the distal end of the elongated rod is positioned within the interior of the joint;
moving the projection into the second position; and
positioning the elongated rod against the interior of the capsule and positioning the projection of the elongated rod against the neck of the femur so as to retract the capsule of the joint.

In another preferred form of the invention, there is provided a method of retracting a capsule of a joint, the method comprising:

providing an elongated rod having a proximal end and a distal end, the distal end comprising a retraction element;
wherein the retraction element comprises a corkscrew;
passing the elongated rod into the capsule of a joint so that the distal end of the elongated rod is positioned on the capsule;
rotating the elongated rod so as to pass the corkscrew through the capsule; and
pulling the elongated rod proximally so as to retract the capsule of the joint.

In another preferred form of the invention, there is provided a method of retracting a capsule of a joint, the method comprising:

providing a length of suture and an anchor attached to one end of the length of suture;
loading the suture and the anchor into a sheath;
passing the sheath into the capsule of a joint;
pushing the anchor through the sheath into the capsule of the joint so that the anchor is positioned on the interior of the capsule, with the suture extending from the anchor; and
pulling the length of suture proximally so as to retract the capsule of the joint.

In another preferred form of the invention, there is provided a method of retracting a capsule of a joint and maintaining the retraction of the capsule of the joint, the method comprising:

providing a length of suture;
providing a cannula having a distal end for positioning in the joint and a proximal end comprising a projection for securing a length of suture;
passing the length of suture through the capsule of the joint so that two free ends of suture extend through the cannula;
pulling the length of suture proximally so as to retract the capsule of the joint; and
securing the length of suture around the projection so as to maintain the retraction of the capsule of the joint.

In another preferred form of the invention, there is provided a method of retracting capsule of a joint, the method comprising:

providing an elongated rod having a proximal end and a distal end, the distal end comprising a hook;
forming a cut in the capsule;
passing the hook of the elongated rod under one side of the cut capsule; and
pulling the elongated rod proximally so as to retract the capsule.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts and further wherein.

Figure 10A:
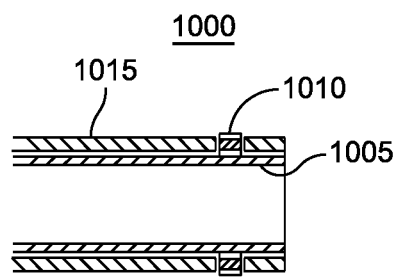
Figure 10B:
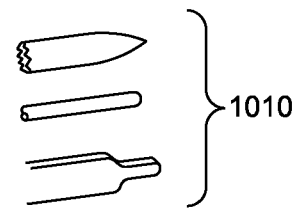
Figure 10C:
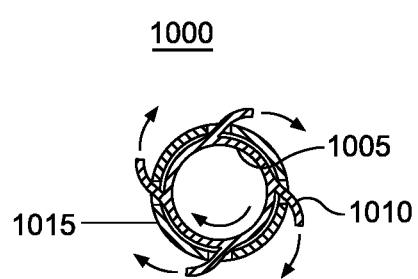
Figure 10D:
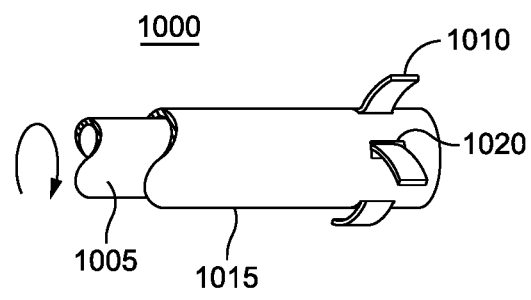
Figure 11A:
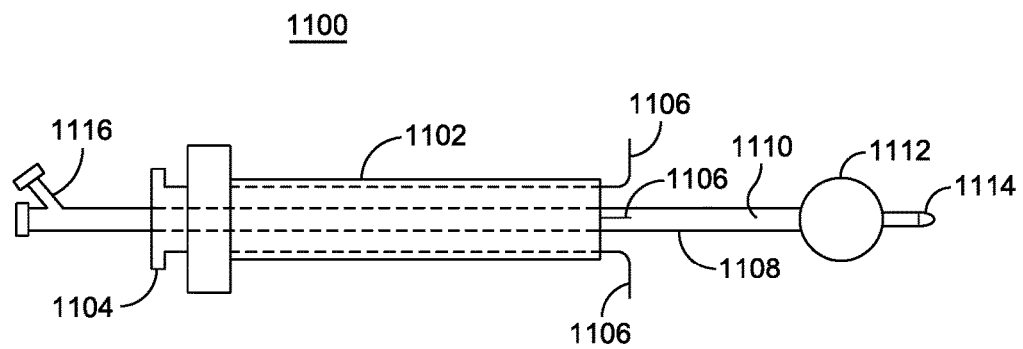
Figure 11B:
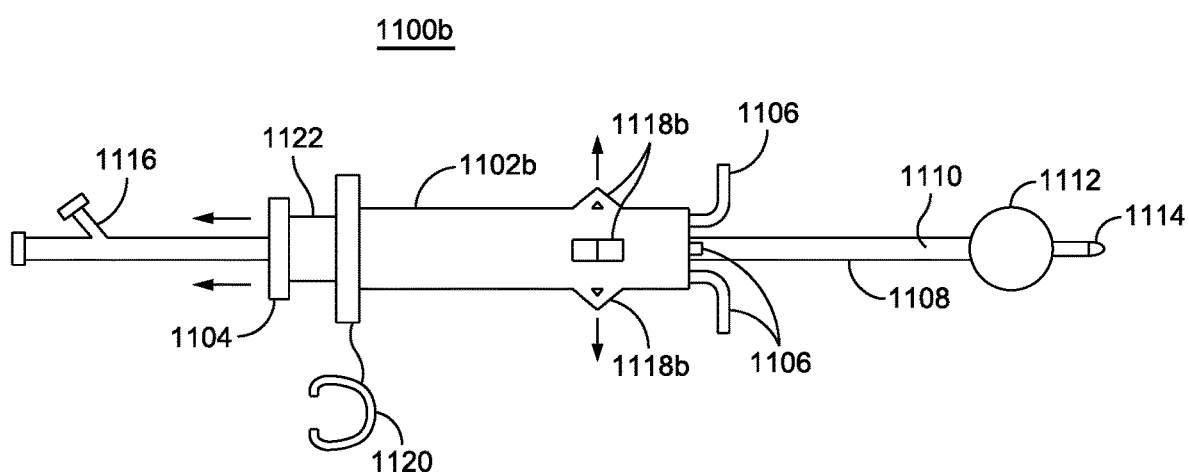
Figure 13A:
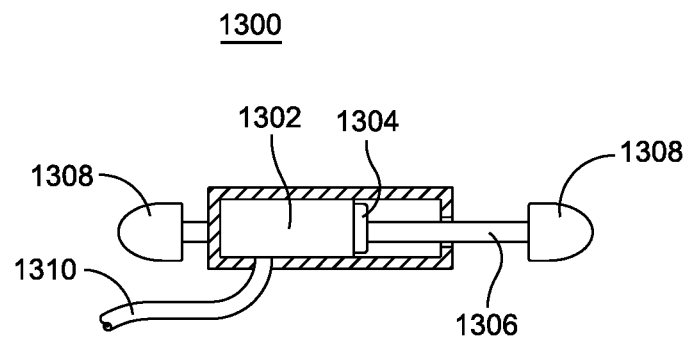
Figure 13B:
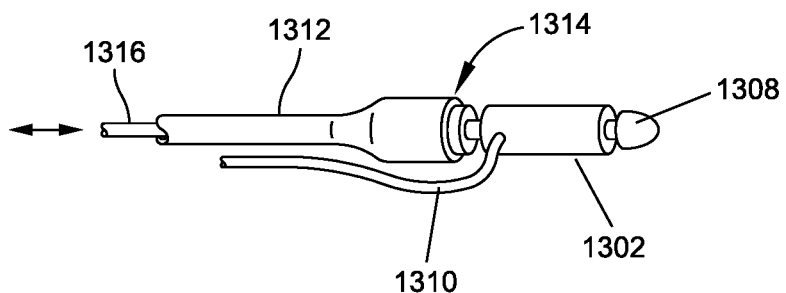
Figure 13C:
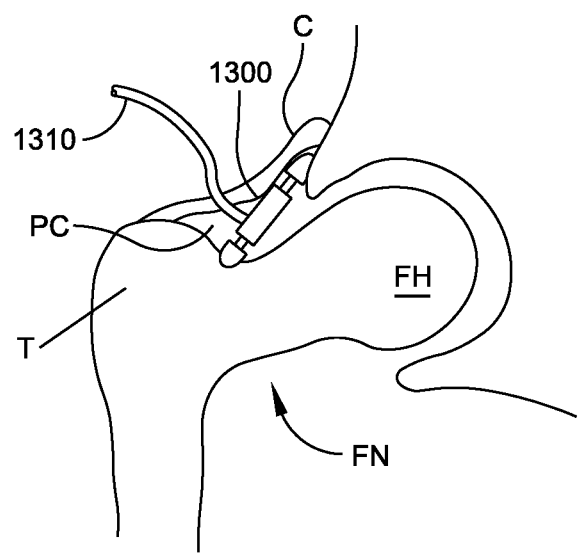
Figure 14A:
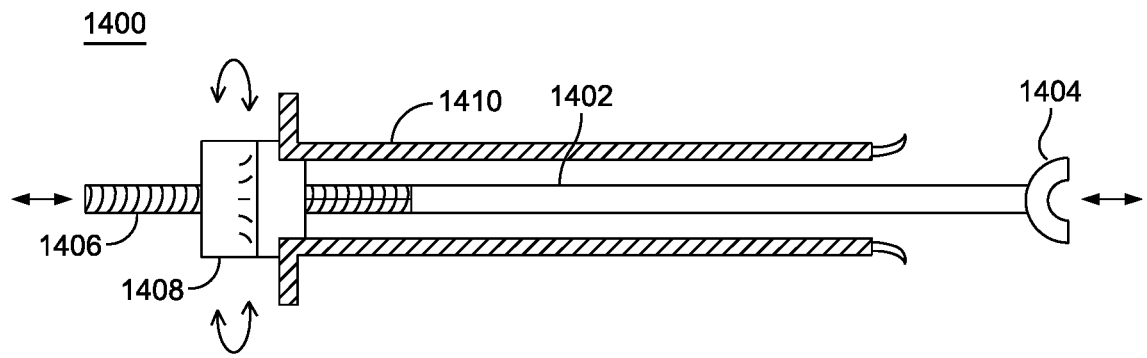
Figure 14B:
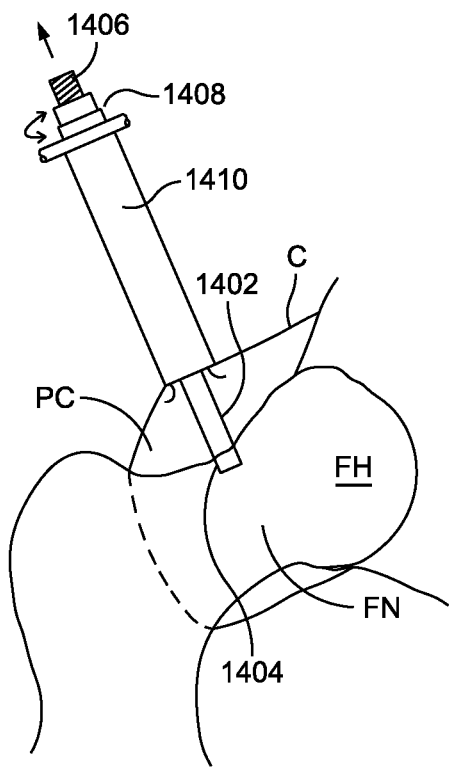
Figure 15A:
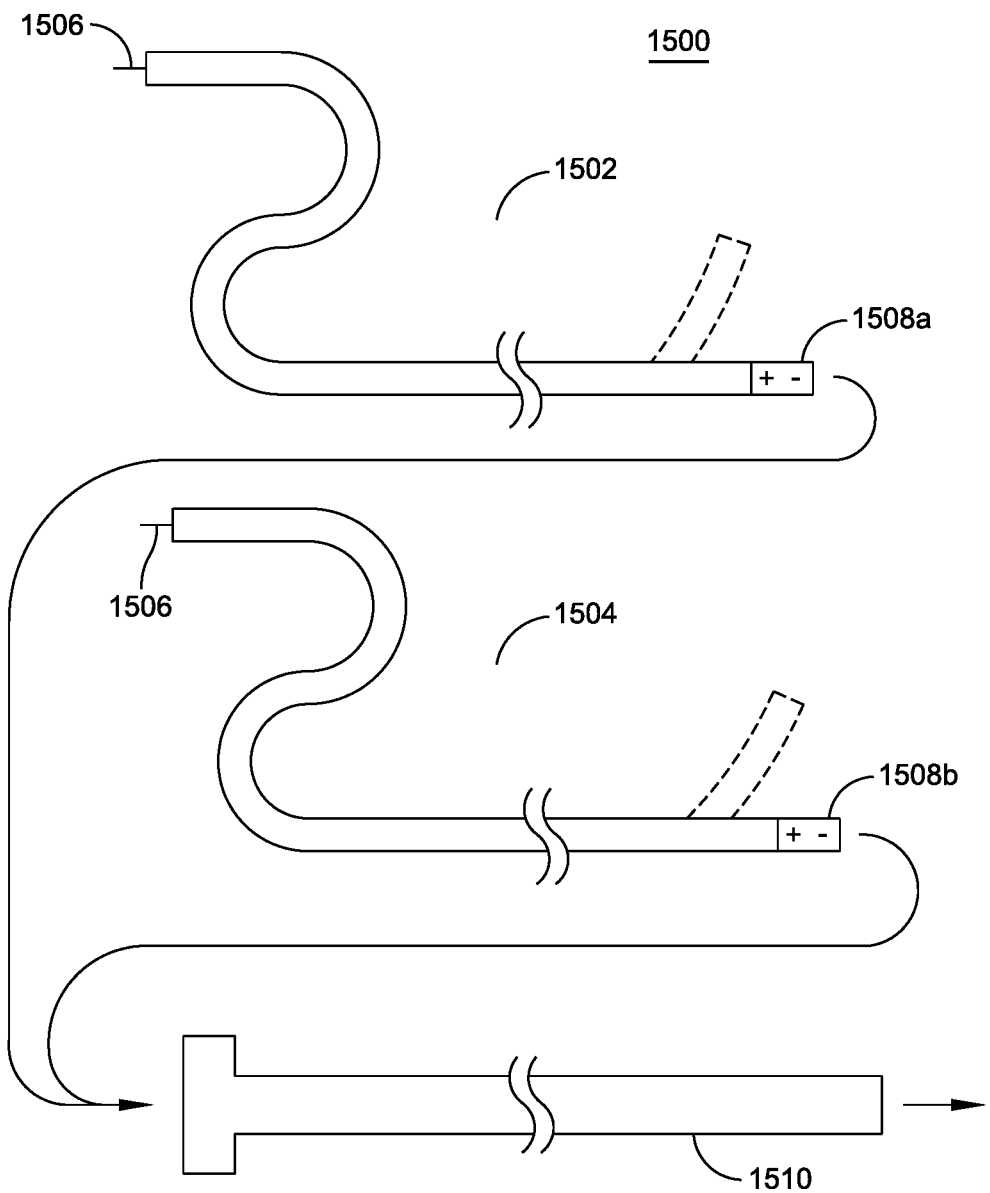
Figure 25:
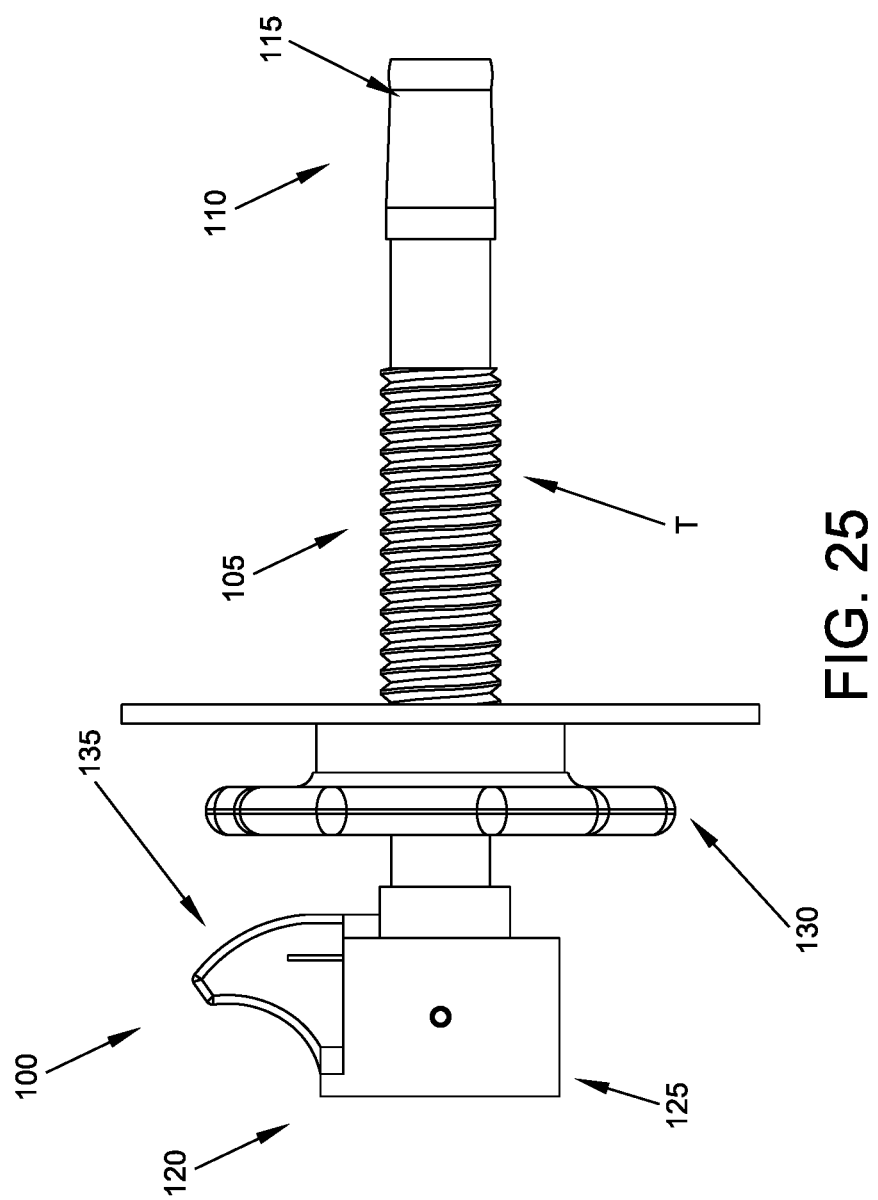
Figure 26:
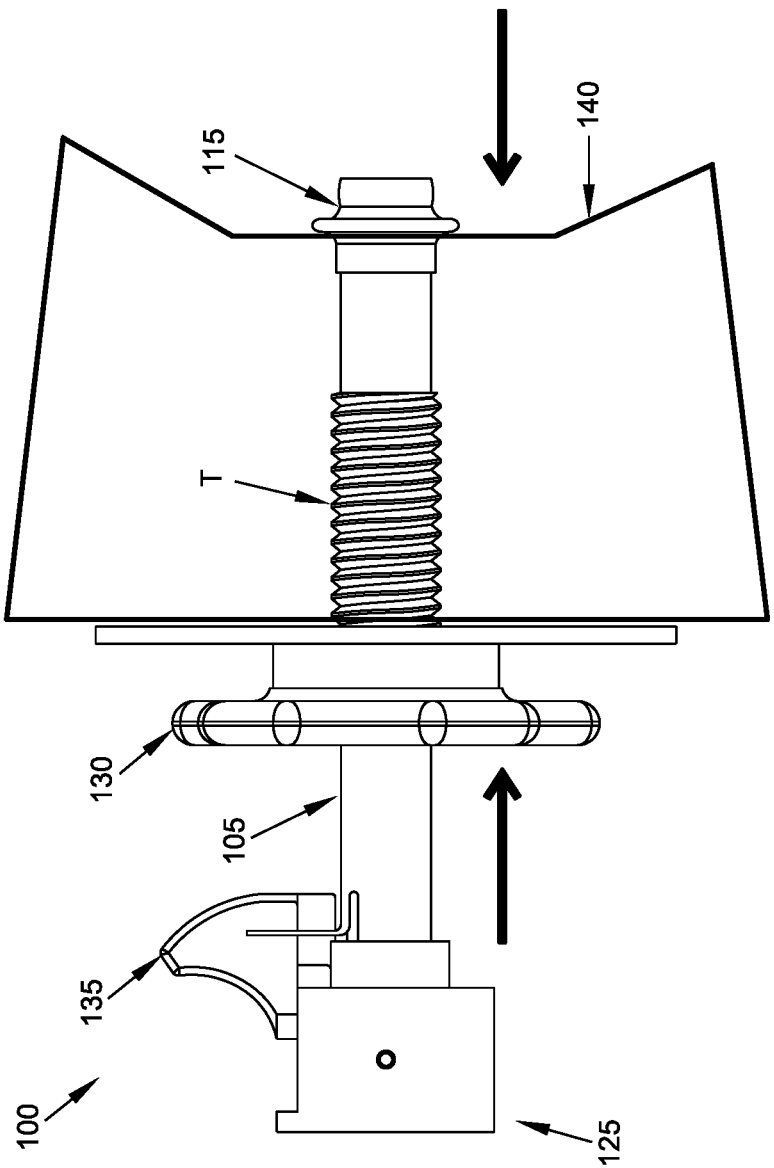
Figure 27:
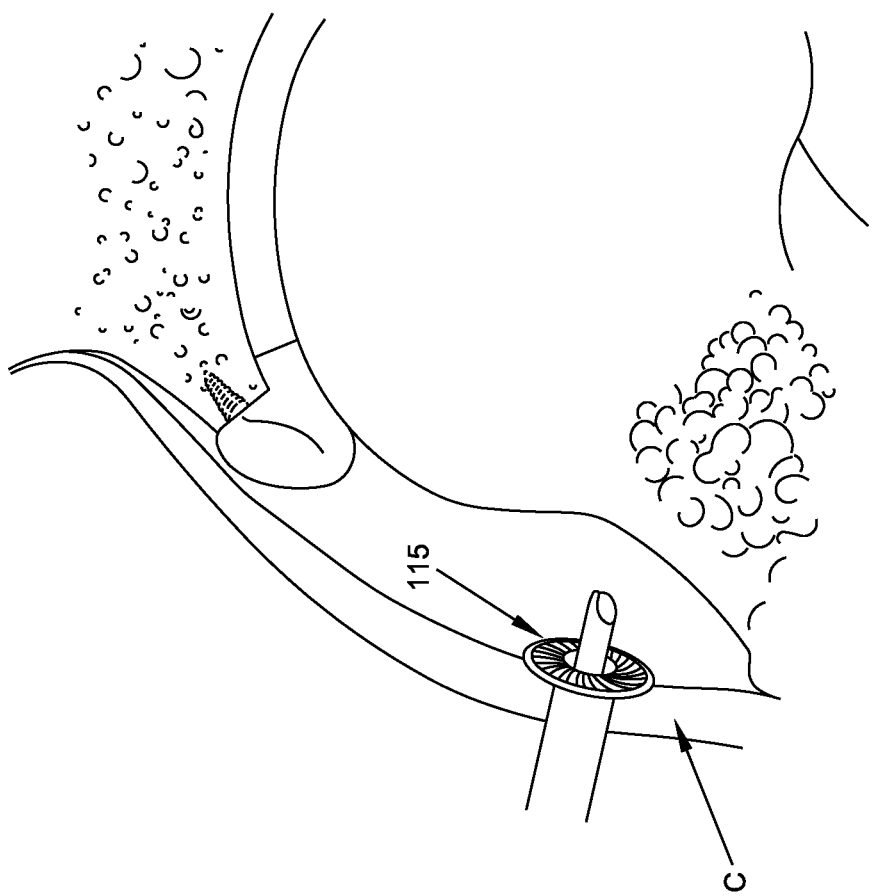
Figure 29:
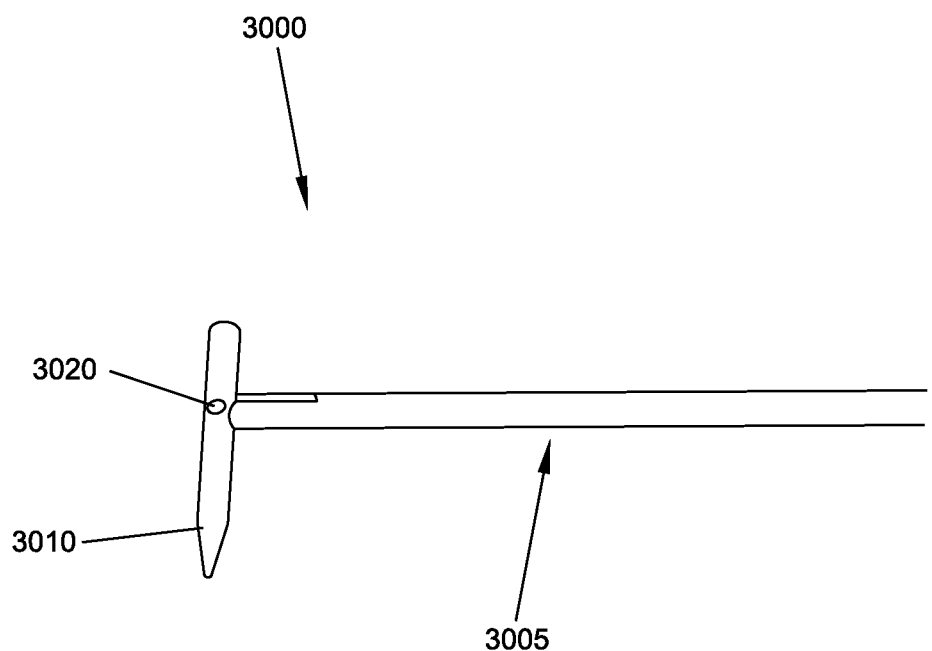
Figure 29A:
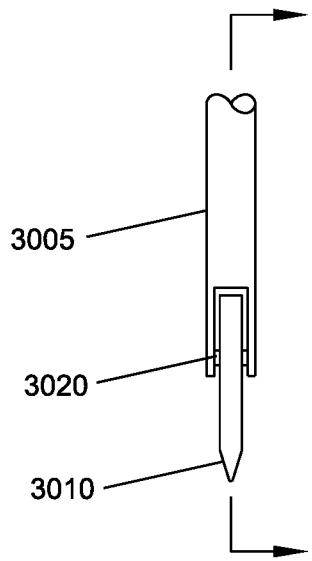
Figure 29B:
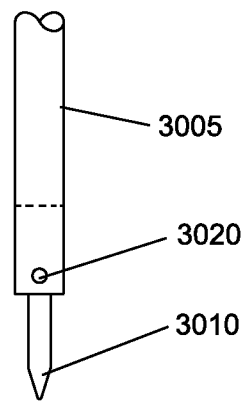
Figure 29C:
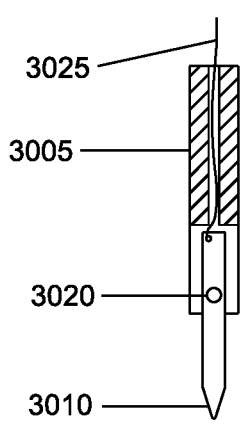
Figure 29D:
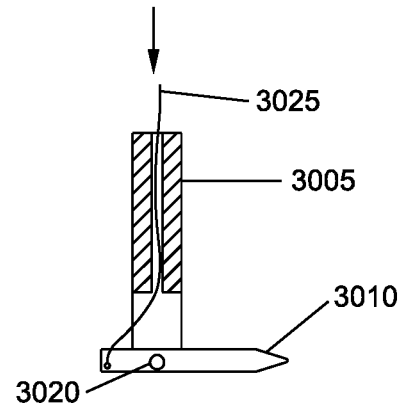
Figure 29E:
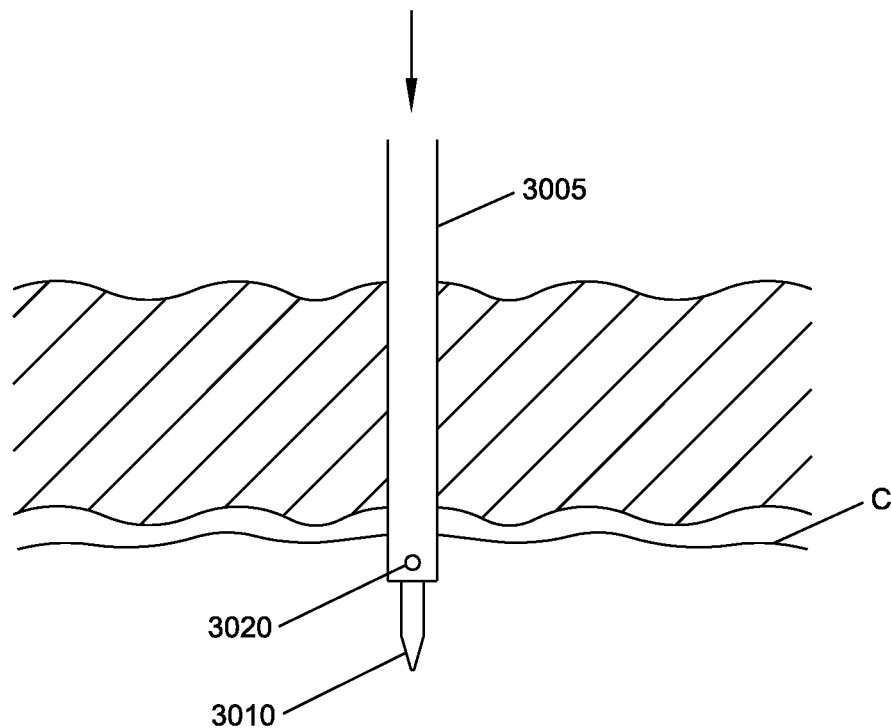
Figure 29F:
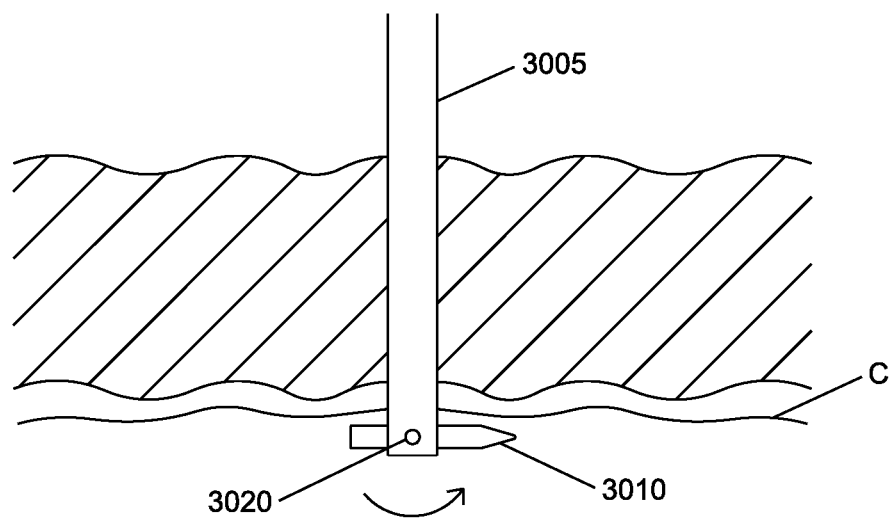
Figure 30:
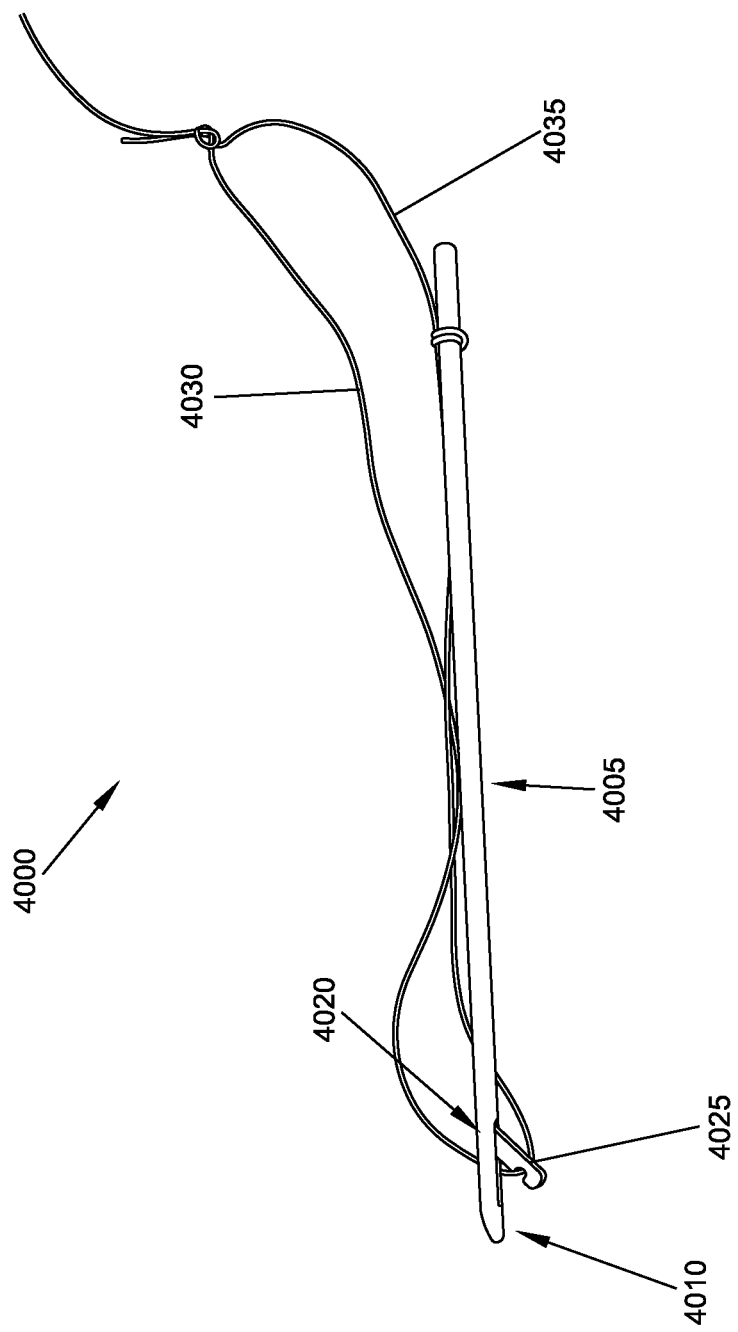
Figure 30A:
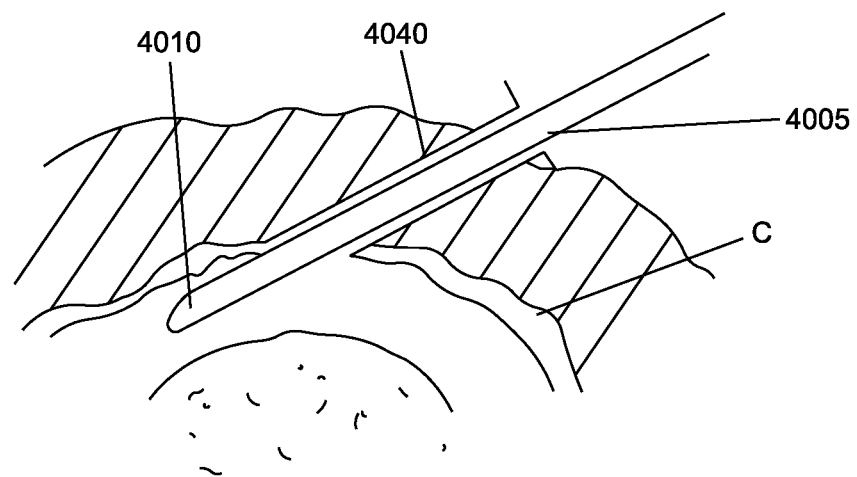
Figure 30B:
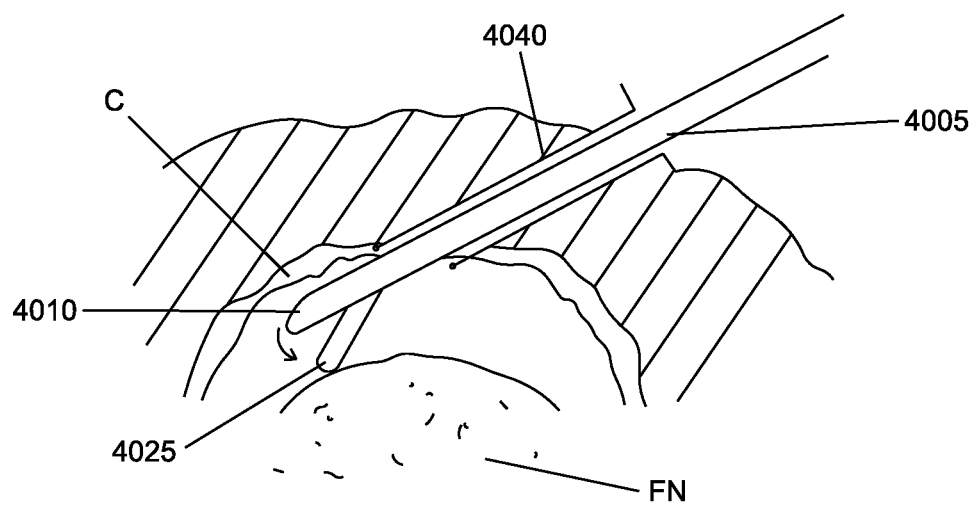
Figure 31:
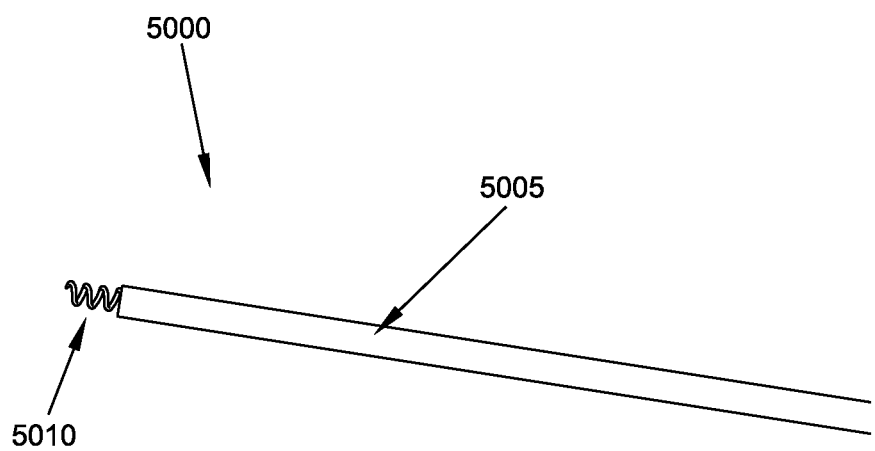
Figure 31A:
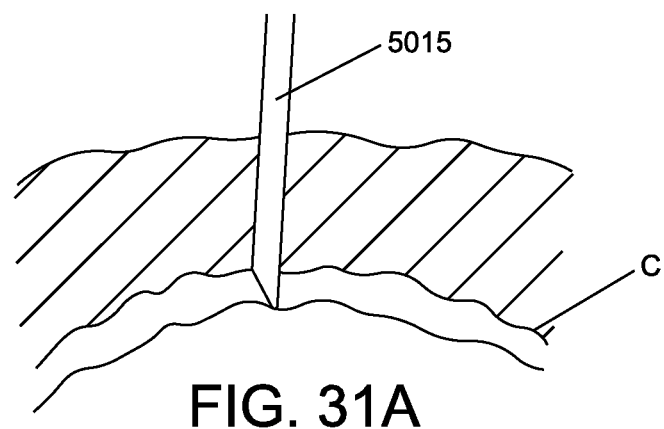
Figure 31B:
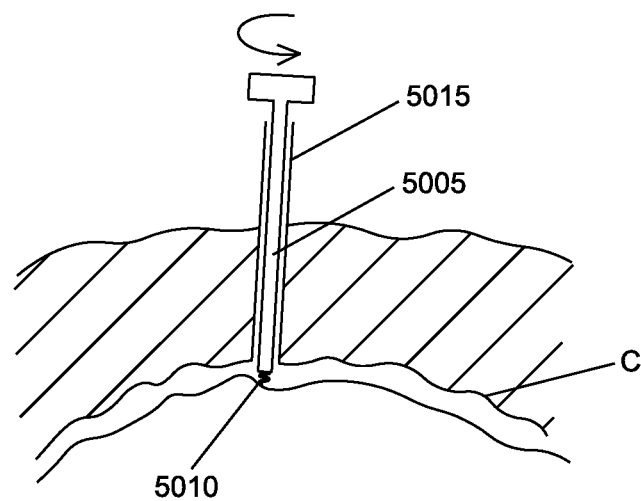
Figure 31C:
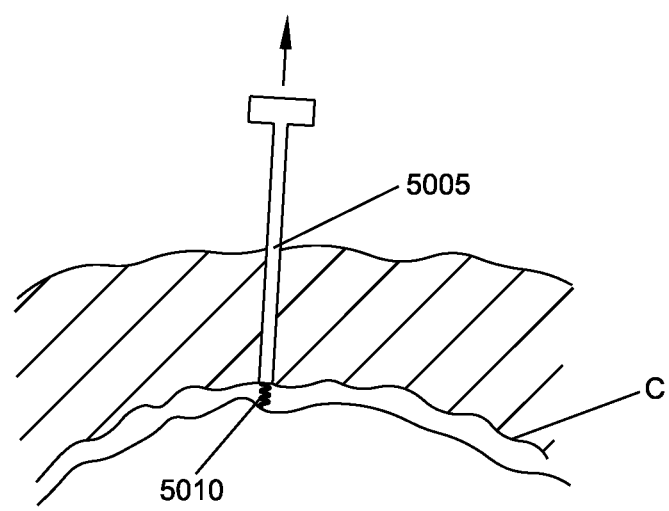
Figure 32:
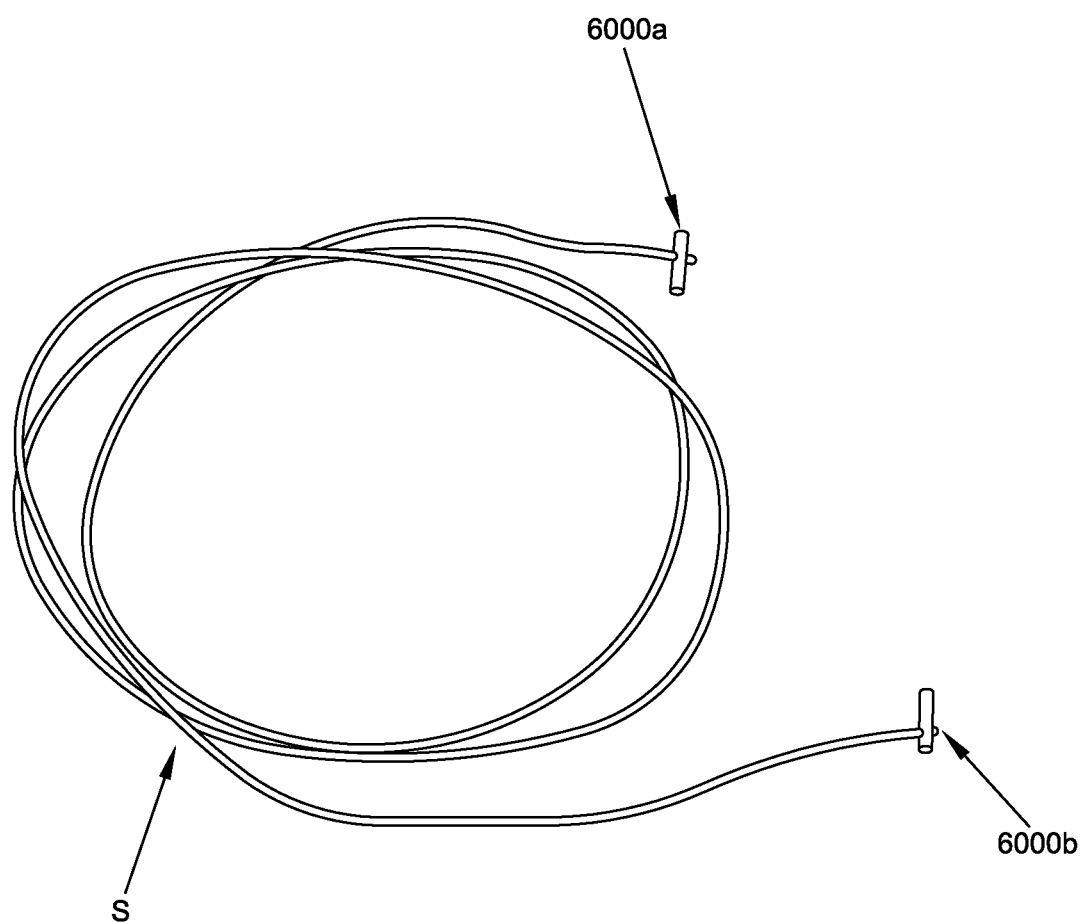
Figure 33:
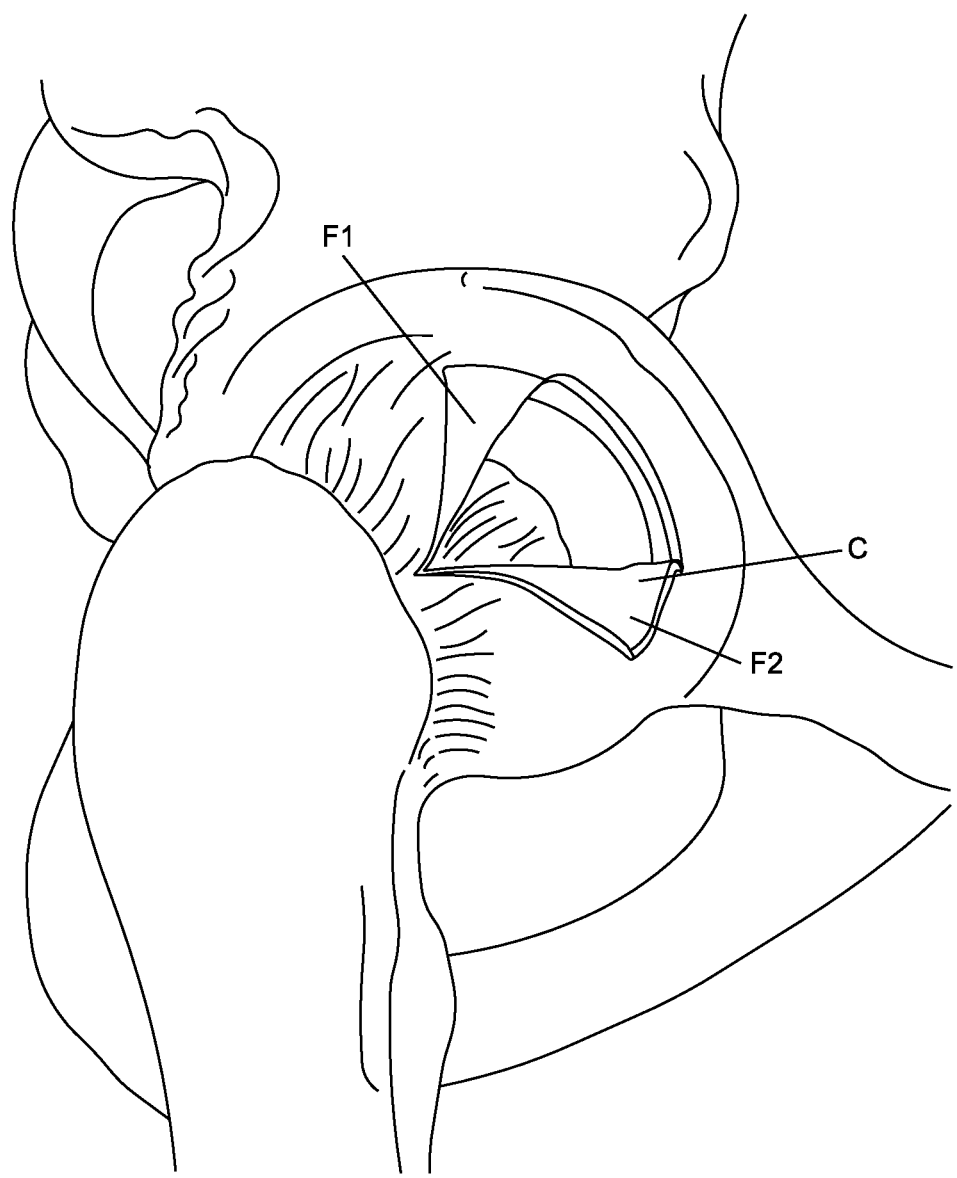
Figure 34:
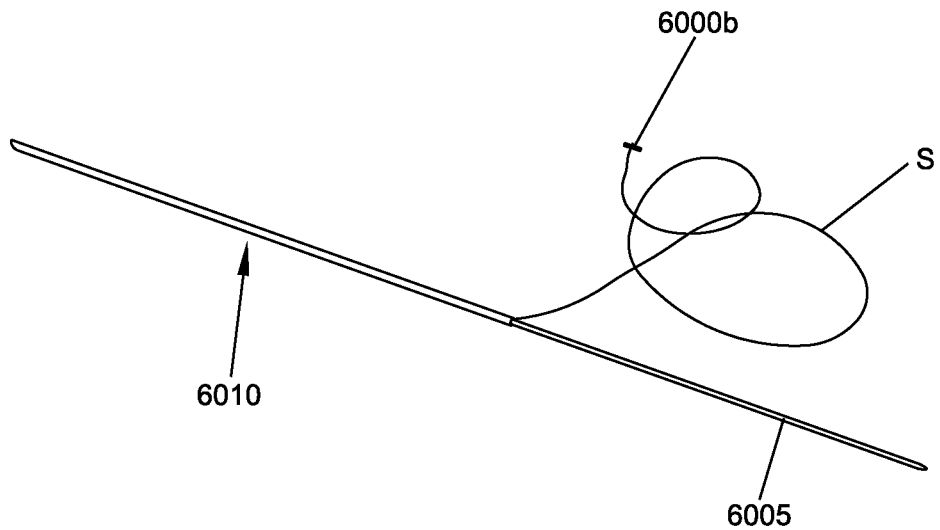
Figure 35:
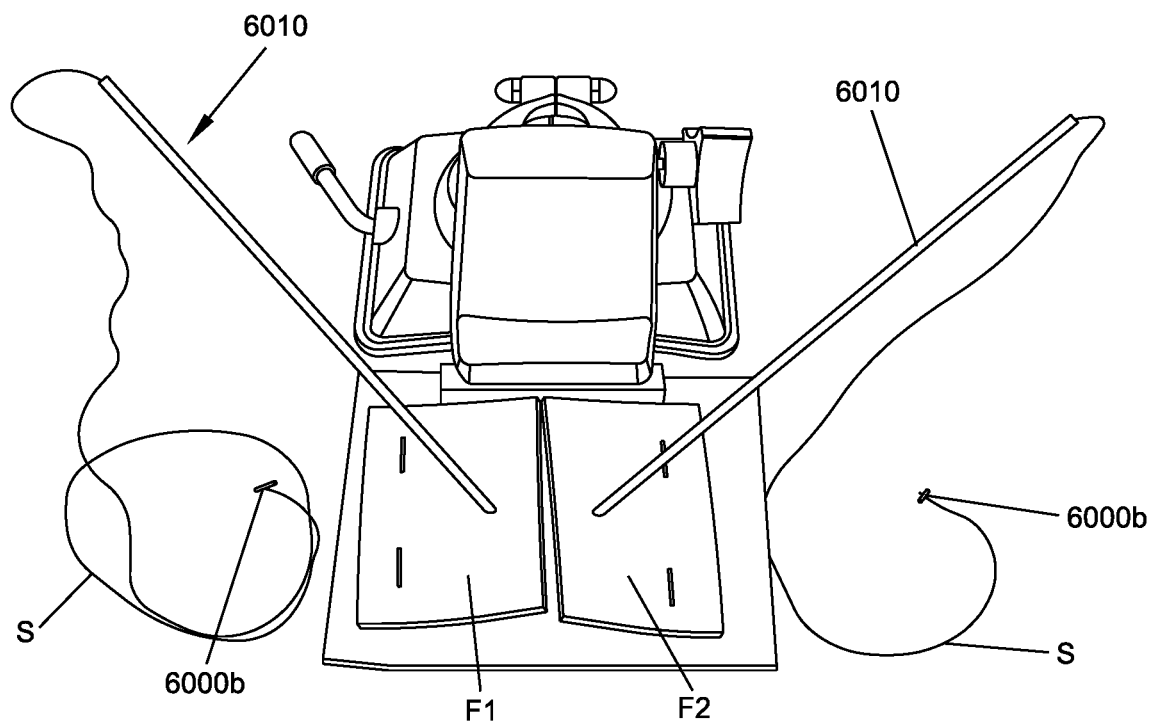
Figure 36A:
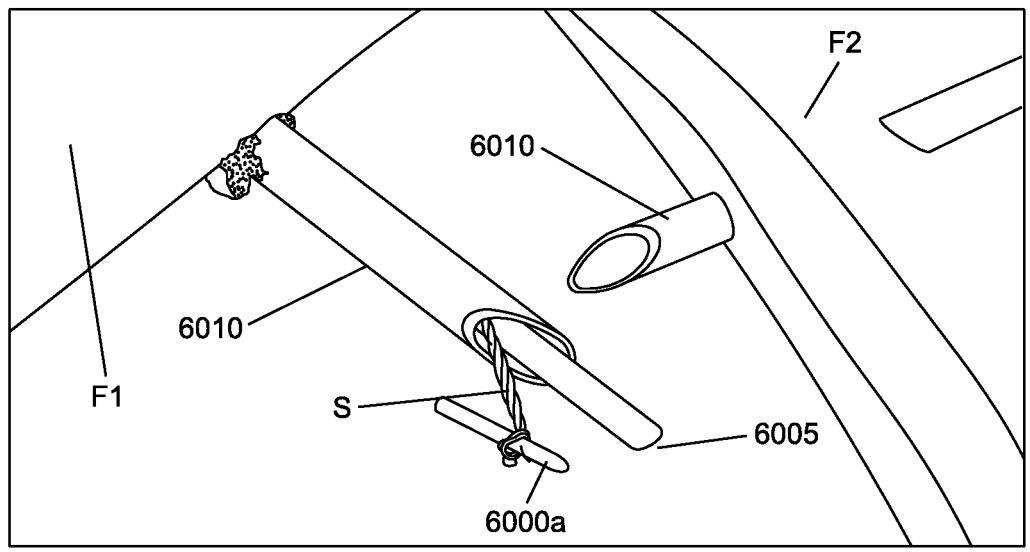
Figure 36B:
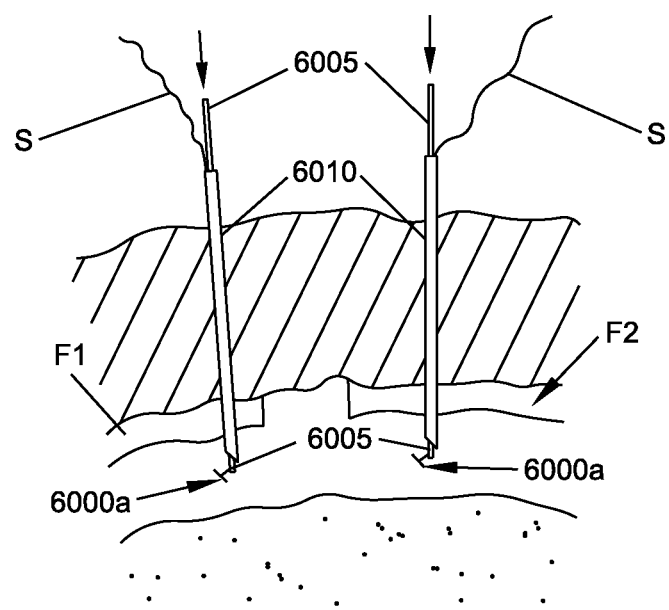
Figure 37:
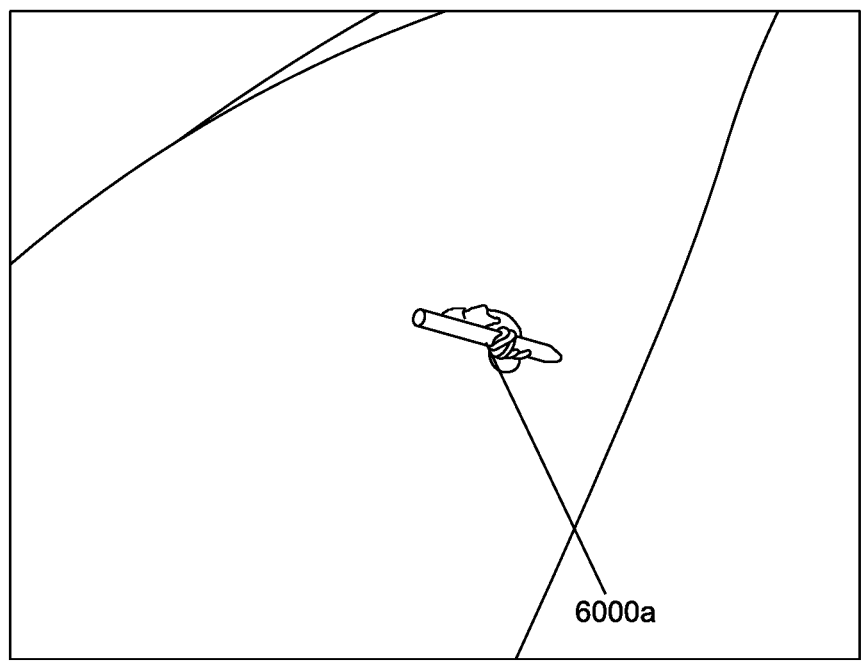
Figure 38A:
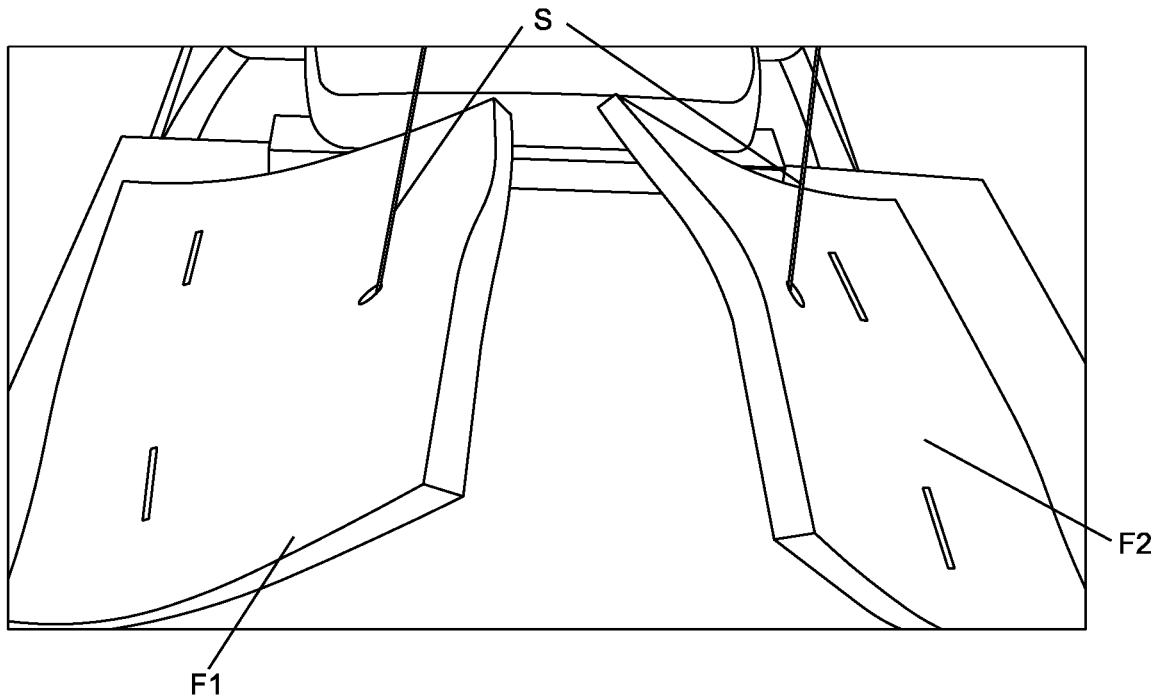
Figure 38B:
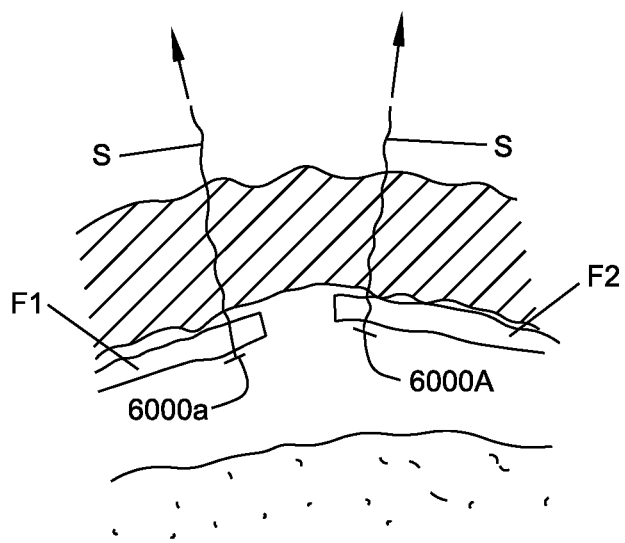
Figure 45:
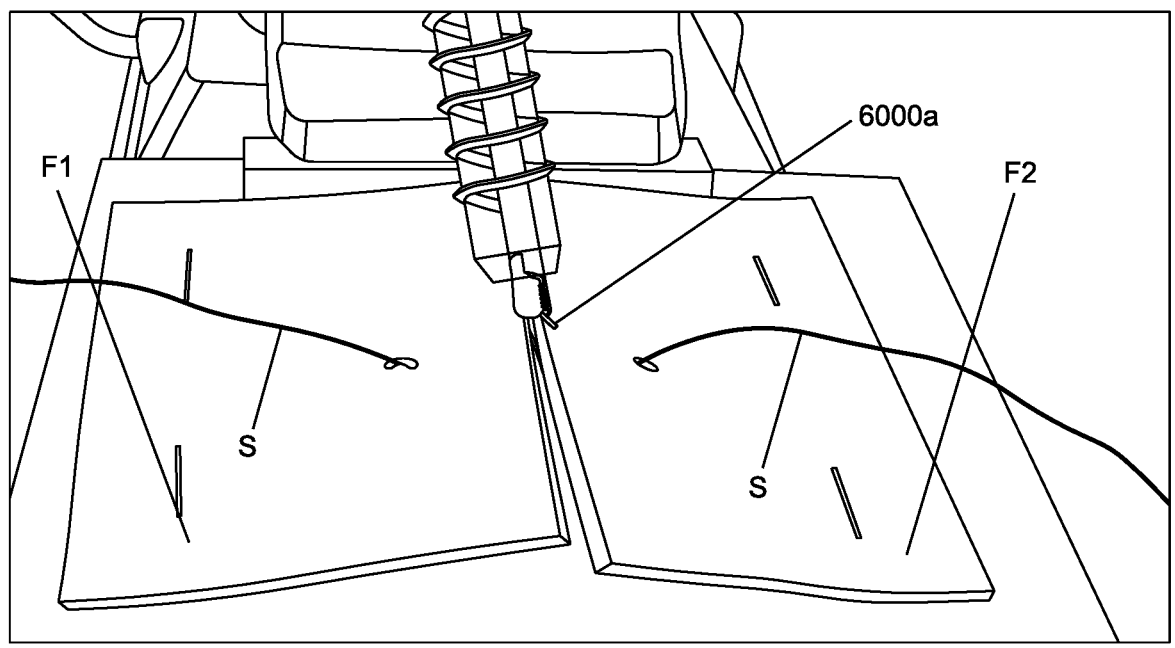
Figure 46:
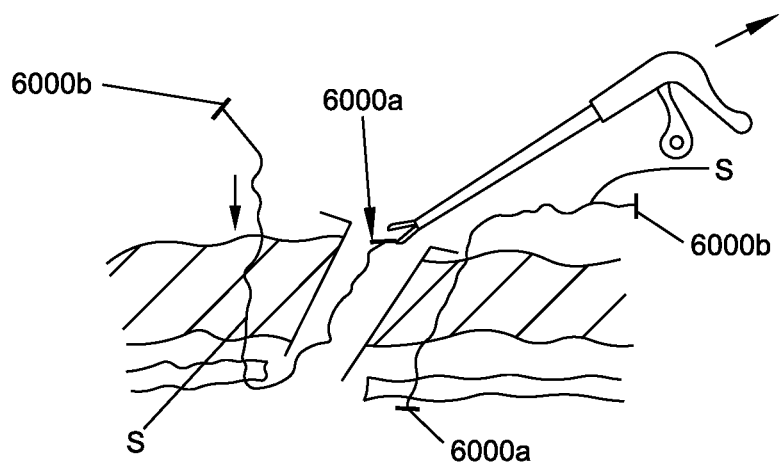
Figure 47A:
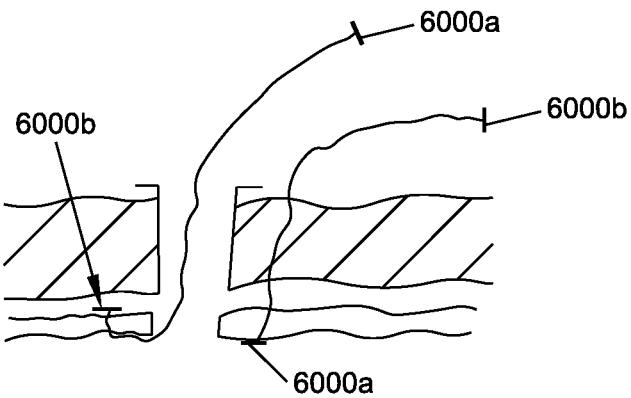
Figure 47B:
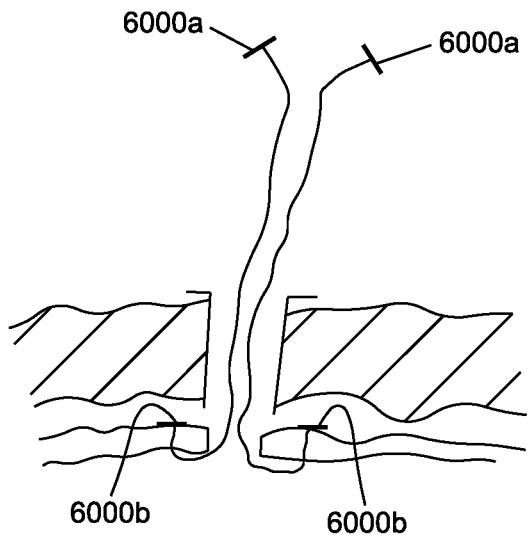
Figure 47C:
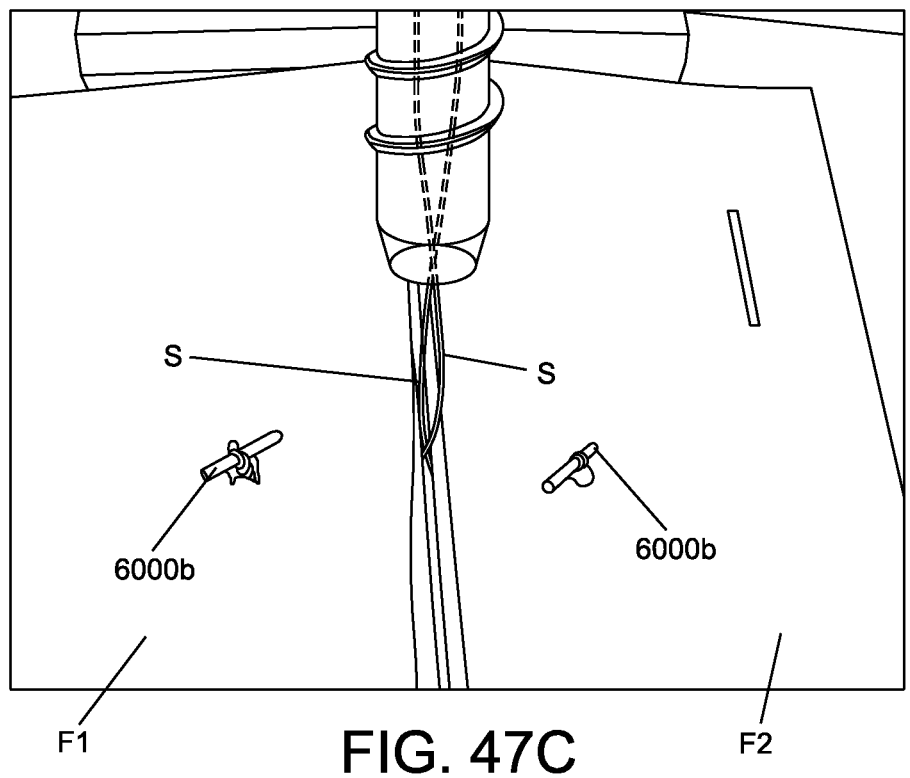
Figure 48:
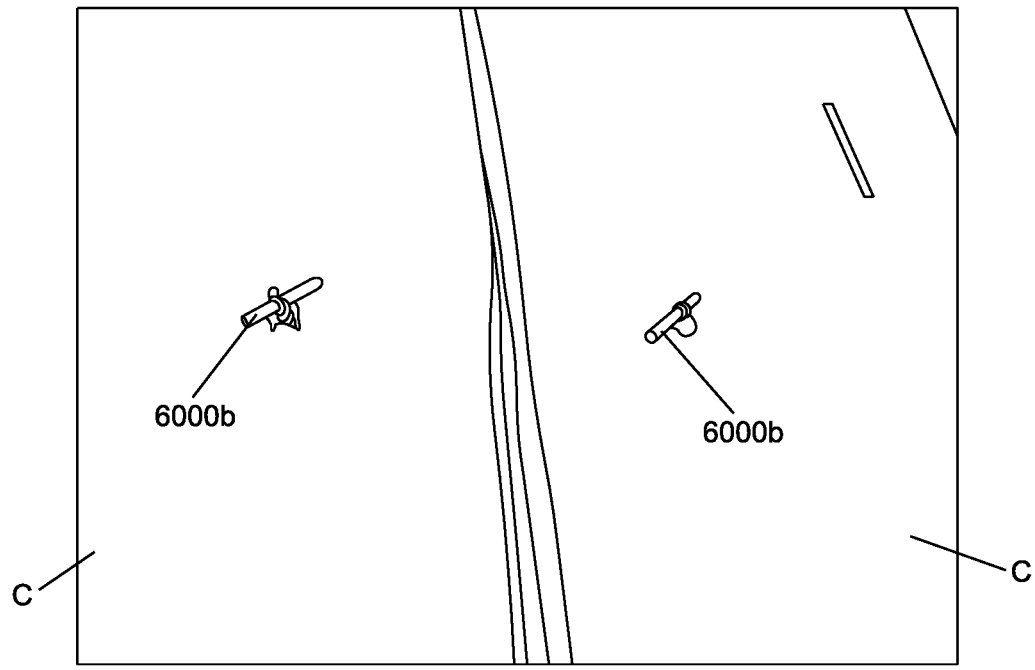
Figure 49:
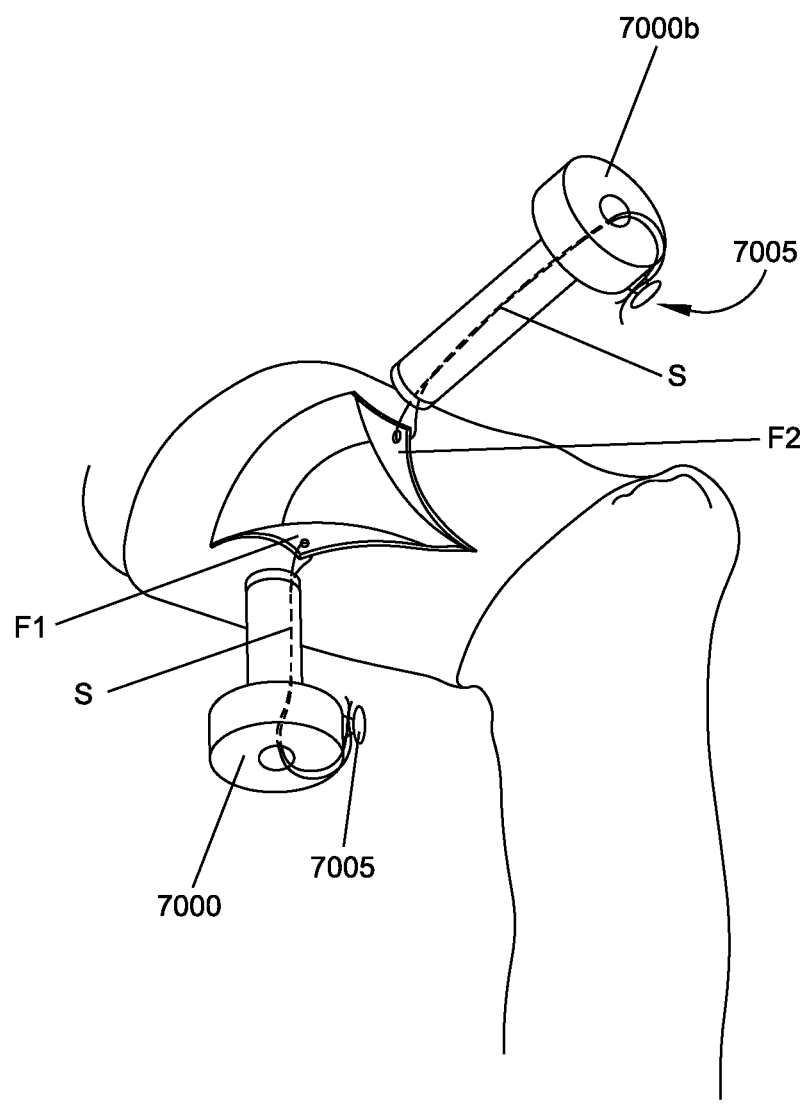
Figure 50:
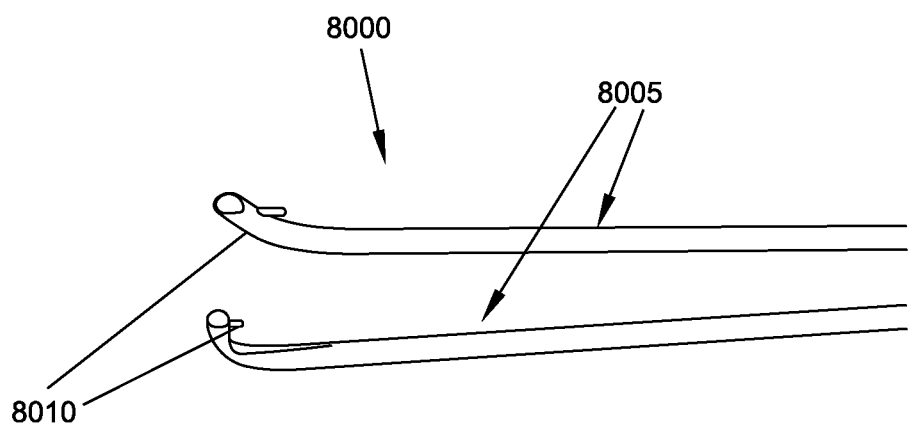

10A is a partial side cross-sectional view of a system for accessing the capsule of a joint, according to an embodiment of the invention;

FIG. 10B is partial side views of grasping devices, according to embodiments of the invention;

FIGS. 10C and 10D are longitudinal cross-sectional and partial side views, respectively, of a system for accessing the capsule of a joint, according to an embodiment of the invention;

FIGS. 11A and 11B are side views of systems for distending a capsule of a joint, according to embodiments of the invention;

11C is a partial cross-sectional view of a hip joint being distended by a system for distending a capsule of a joint, according to an embodiment of the invention;

FIGS. 12A-12E are partial side views of systems for distending a capsule of a joint, according to embodiments of the invention;

FIG. 13A is a cross-sectional view of a device for distending a capsule of a joint, according to an embodiment of the invention;

FIG. 13B is a side view of a system for distending a capsule of a joint, according to an embodiment of the invention;

FIG. 13C is a partial cross-sectional view of a hip joint being distended by a device for distending a capsule of a joint, according to an embodiment of the invention;

FIG. 14A is a cross-sectional view of a system for distending a capsule of a joint, according to an embodiment of the invention;

FIG. 14B is a partial cross-sectional view of a hip joint being distended by a system for distending a capsule of a joint, according to an embodiment of the invention;

FIG. 15A is a side view of a system for distending a capsule of a joint, according to an embodiment of the invention;

FIGS. 15B-15F are partial cross-sectional views of a hip joint being distended by a system for distending a capsule of a joint, according to an embodiment of the invention;

FIGS. 16-19 are schematic views of a locking access cannula, according to an embodiment of the invention;

FIGS. 20-24 are schematic views of a method of using the access cannula of FIGS. 16-19;

FIG. 25 is a schematic view of a tensioning access cannula, according to an embodiment of the invention;

FIGS. 26 and 27 are schematic views of a method of using the tensioning access cannula of FIG. 25;

FIGS. 28A-28E are schematic views of a device for retracting the capsule of a joint, according to an embodiment of the invention;

FIGS. 28F-28I are schematic views of a method of using the device of FIGS. 28A-28E to retract the capsule of a joint, according to an embodiment of the invention;

FIGS. 29 and 29A-29D are schematic views of a device for retracting the capsule of a joint, according to an embodiment of the invention;

FIGS. 29E and 29F are schematic views of a method of using the device of FIGS. 29 and 29A-29D to retract the capsule of a joint, according to an embodiment of the invention;

FIG. 30 is a schematic view of a device for retracting the capsule of a joint, according to an embodiment of the invention;

FIGS. 30A and 30B are schematic views of a method of using the device of FIG. 30 to retract the capsule of a joint, according to an embodiment of the invention;

FIG. 31 is a schematic view of a device for retracting the capsule of a joint, according to an embodiment of the invention;

FIGS. 31A-31C are schematic views of a method of using the device of FIG. 31 to retract the capsule of a joint, according to an embodiment of the invention;

FIG. 32 is a schematic view of a device for retracting the capsule of a joint, according to an embodiment of the invention;

FIGS. 33-38B are schematic views of a method of using the device of FIG. 32 to retract a capsule of a joint, wherein FIGS. 35 and 38 are schematic views taken from the outside of the capsule;

FIGS. 39-48 are schematic views of a method of using the device of FIG. 32 to close the capsule of a joint, wherein FIGS. 39-44 and 46-47B are cross-sectional views of the joint and FIGS. 45, 47C and 48 are schematic views taken from the outside of the capsule; and FIGS. 49 and 50 are schematic views of devices for retracting a capsule of a joint, according to an embodiment of the invention.

DETAILED DESCRIPTION OF THE INVENTION

Devices and methods are disclosed herein for accessing the hip joint. The devices described herein can provide safely made portals within the capsule for access to the peripheral compartment by other devices. For example, the devices described herein generally provide access to the peripheral compartment by grasping and securely engaging the capsule with a first device, typically a cannula or sheath. The first device is secured enough to enable the first device to pull the capsule away from the joint and "tent" of the capsule. Tenting the capsule creates a larger volume within the peripheral compartment. A second device, typically a needle, can then be biased against the first device to apply a piercing force against the tented capsule. The use of counter-traction against the first device allows the second device to be advanced into the capsule in a controlled manner to avoid "popping" uncontrollably into the peripheral compartment. Tenting of the capsule also provides an additional safety margin by providing extra space between the capsule and the tissue beyond it for the second device to traverse. The devices and methods herein do not require the use of a traction table to safely pierce the capsule.

Devices and methods are also disclosed herein for distending the capsule of a joint to enlarge the working area within the peripheral compartment. For example, a distension device can access the peripheral compartment after a safely made portal has been established as described herein.

A distension device can then apply an expansive force within the peripheral compartment to distend and stretch the capsule. Accordingly, the peripheral compartment becomes enlarged which allows for better access by other surgical devices. In some embodiments, the distension device can continually distend the peripheral compartment while other devices access the joint. Distension of the capsule can allow for fewer portals to be established into the capsule, as greater working space is created. It should be understood that the devices of the invention may be useful for access into other joints besides the hip, such as the shoulder, knee, or ankle. It should also be understood that devices of the invention are useable in conjunction with visual guidance systems such as fluoroscopy and arthroscopy systems.

Figure 1:
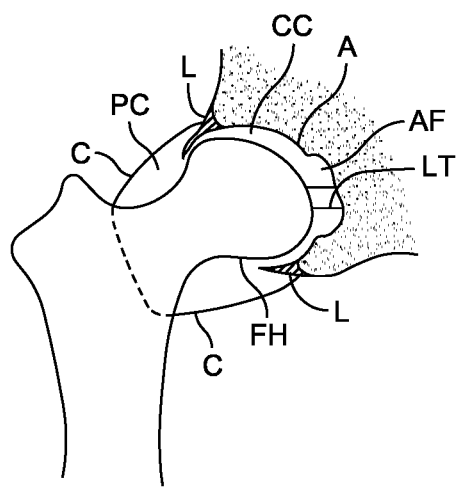
FIG. 1 is a simplified cross-sectional view of a hip joint.

FIG. 1 illustrates the basic anatomy of a hip joint. The hip joint is formed between the head of the femur FH and the acetabulum A, a concave surface of the pelvis. The acetabular fossa AF is a recessed region in the acetabulum. A blanket of ligaments covers the joint forming a capsule C. Additionally, the acetabular labrum L, a fibrocartilaginous lip, surrounds the head of the femur, deepens the joint pocket and increases the surface area of contact. Labrum L divides the hip joint into two compartments within the joint capsule: a central compartment CC and a peripheral compartment PC. Central compartment CC is within the confines of labrum L and contains the majority of the joint cartilage and the ligamentum teres LT, a ligament attached to a depression in the acetabulum (the acetabular notch or fossa) and a depression on the femoral head (the fovea of the head). Peripheral compartment PC is everything outside the labrum and within the capsular ligaments C. The central compartment CC is generally not visible until the joint has been distracted.

Figure 2:
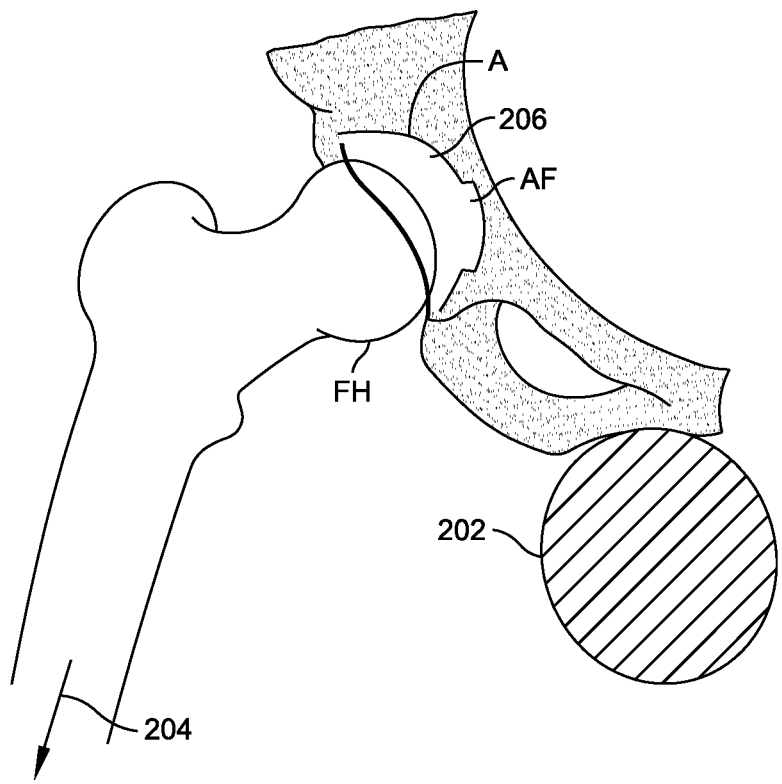
FIG. 2 is a simplified cross-sectional view of a hip joint undergoing a prior art method for distracting a femoral head from an acetabulum.

FIG. 2 illustrates how traction 204 is conventionally applied to a patient's leg and against a post 202 positioned against the perineum region to distract femoral head HI away from acetabulum A, thereby creating a space 206 between the two joint surfaces. This space 206 allows a surgeon to access the joint and perform diagnostic or therapeutic procedures.

Figure 3:
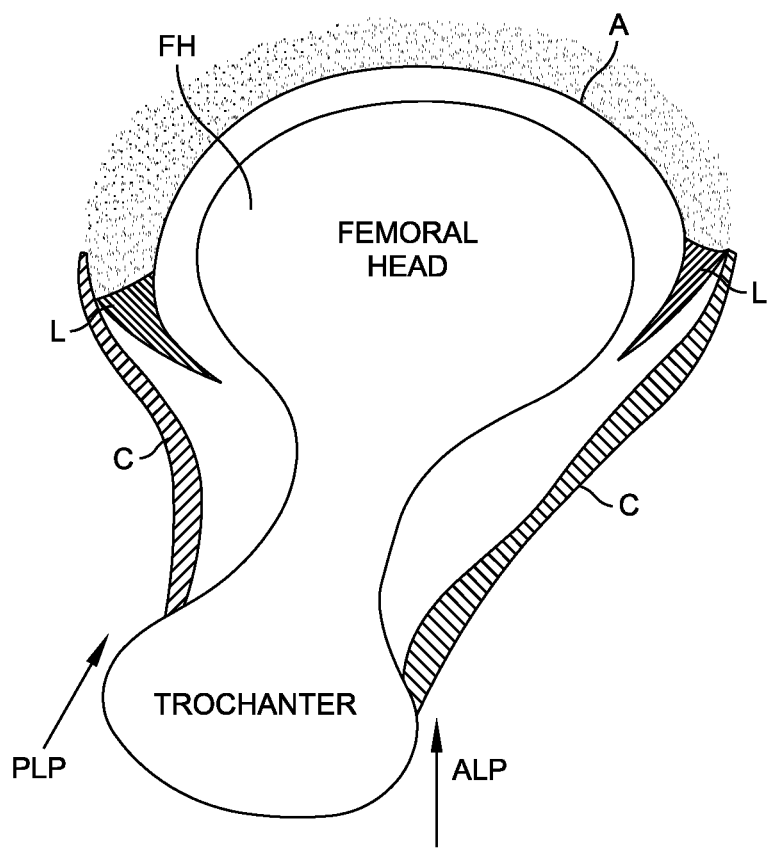
FIG. 3 is a simplified cross-sectional view of a hip joint.

FIG. 3 illustrates some of the possible entry portals for delivering instruments into the hip joint. FIG. 3 is a top view of a hip joint in which femoral head RI rests against acetabulum A. The joint space is covered by capsule C and labrum L. Access into the joint may be obtained by introducing instruments through a posterolateral portal PLP along a side and posterior to the joint or an anterolateral portal ALP along a side and anterior to the joint.

Peripheral Compartment Access

Figure 4A:
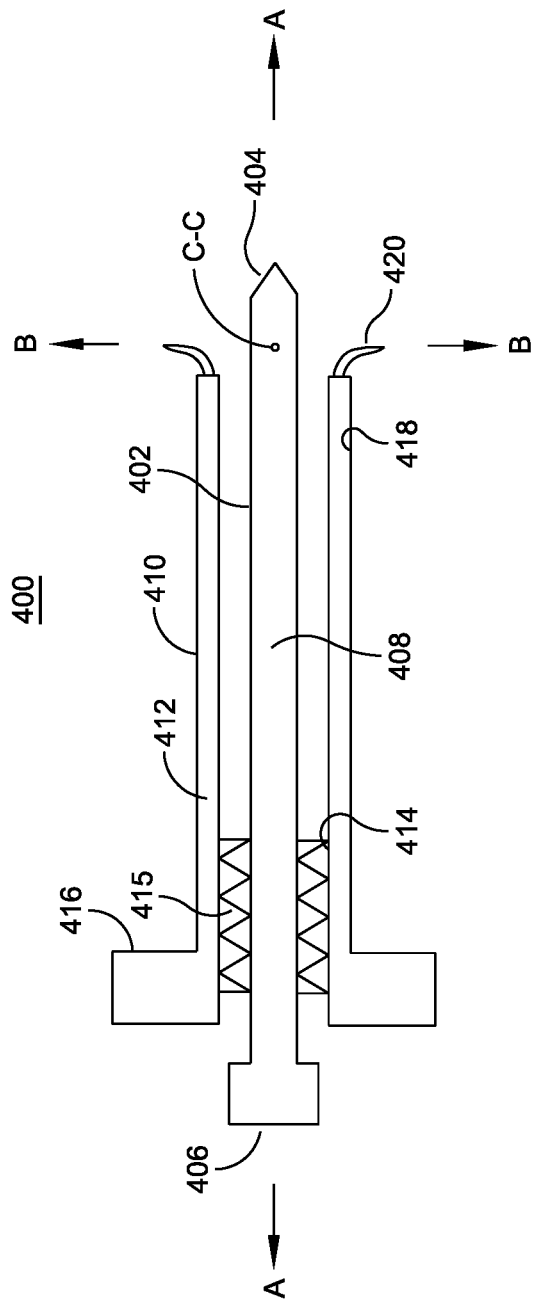
FIG. 4A is a cross-sectional view of a system for accessing the capsule of a joint, according to an embodiment of the invention.

FIG. 4A illustrates a system 400 for accessing the capsule of a joint. The system 400 includes an elongated needle 402. As used herein, "needle" may encompass various devices for penetrating the capsular tissue, and is meant to include a variety of puncturing devices including, for example, trocars, coring (hollow) needles, non-coring (solid) needles, and stylet/needle combinations, as well as blunt-tipped instruments such as dilators or tubular devices. Needle 402 may be a commercially available 18-27 gauge spinal needle. Needle 402 may be constructed from a metal (e.g., stainless steel) or a polymer. Needle 402 may include one or more lumens fluidly connected to one or more openings in or near a distal tip 404. Distal tip 404 may include one or more bevels. Needle 402 may include a sensor, such as a strain gauge or load cell, functionally coupled to an interior or exterior portion of the needle.

Needle 402 may include an enlarged proximal member 406. Enlarged proximal member 406 may be a comparatively enlarged mass of material (e.g., a flange) with respect to a central portion 408 of needle 402. Proximal member 406 and/or central portion 408 may include threaded portions. Proximal member 406 may also be a fluidic connector, such as a Luer connector, in fluid communication with one or more lumens and respective distal openings. If a sensor is included with the needle, the sensor may be electrically connected to an electrical connector of proximal member 406.

System 400 also includes a cannula or elongated sheath 410. Sheath 410 includes a cylindrical body 412 with an inner surface 414. Inner surface 414 may be diametrically sized to enable needle 402 and sheath 410 to freely slide with respect to each other along longitudinal direction A-A. Inner surface 414 may include threads 415 which may threadably engage with a portion of needle 402. Inner surface 414 may be diametrically sized to allow other cylindrical devices, such as cannulas, sheaths, stents, etc., to fit between needle 402 and inner surface 414. Inner surface 414 may have a diameter ranging from 2 to 15 millimeters. Sheath 410 may be constructed from a metal (e.g., stainless steel) or a polymer. Sheath 410 includes a proximal flange 416 which extends circumferentially from cylindrical body 412. Sheath 410 may have an overall length of 50 to 150 millimeters.

A distal end 418 of sheath 410 includes a plurality of grasping members 420. Sheath 410 includes at least two opposed grasping members 420, and may include more (e.g., 3 to 20) grasping members 420. Grasping members 420 are circumferentially spaced with respect to cylindrical body 412 in an even manner. Grasping members 420 may extend in an approximate radial direction B-B, which is tangent to directions A-A, from cylindrical body 412. Grasping members 420 may also extend in an approximate tangential direction C-C, which is tangent to directions A-A and B-B, from cylindrical body 412. The grasping members may also extend in directions between directions A-A, B-B, and C-C.

Grasping members 420 may be configured as hooks or barbs. Grasping members 420 may fixedly extend from distal end 418 or be retractable and extendable within or along proximal end 418. Portions of grasping members 420 may slidably extend within cylindrical body 412 to proximal flange 416. Grasping members 420 may be constructed from a metal (e.g., stainless steel, shape-memory or super elastic nitinol (Ni—Ti)) or a polymer. Grasping members 420 may be part of a greater structure, such as a sheath or stent, internally or externally coupled to sheath 410.

Figure 4B:
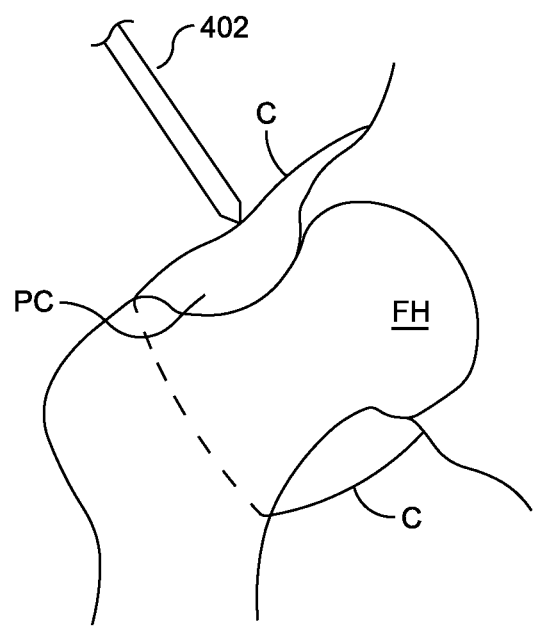
FIGS. 4B-4F are cross-sectional views of a hip joint being accessed by a system for accessing the capsule of a joint, according to an embodiment of the invention.

FIGS. 4B-4F illustrate a method of use for system 400, for accessing and penetrating the capsule of a joint. In FIG. 4B, an incision is made in the skin and needle 402 is used to penetrate the outer tissue surrounding capsule C. Needle 402 may be placed in various portal access locations, such as the anterolateral, distal-anterolateral and anterior locations. Needle 402 is then maintained at the surface of the capsule. Optionally, needle 402 may partially or fully penetrate the capsular tissue.

Figure 4C:
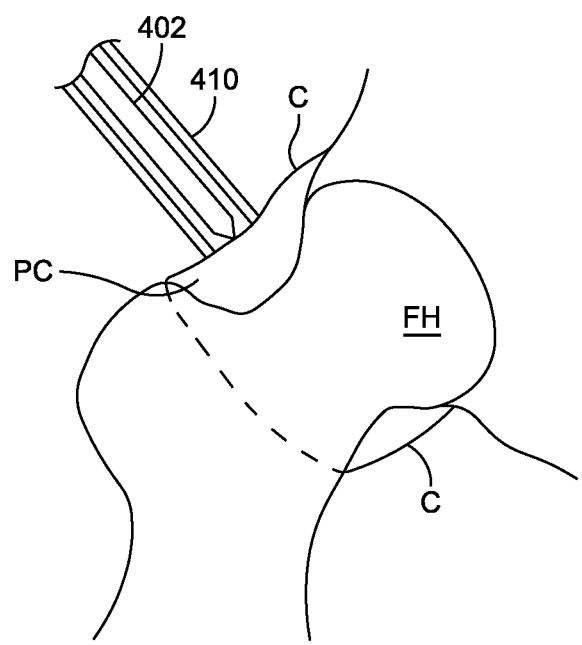
Figure 4D:
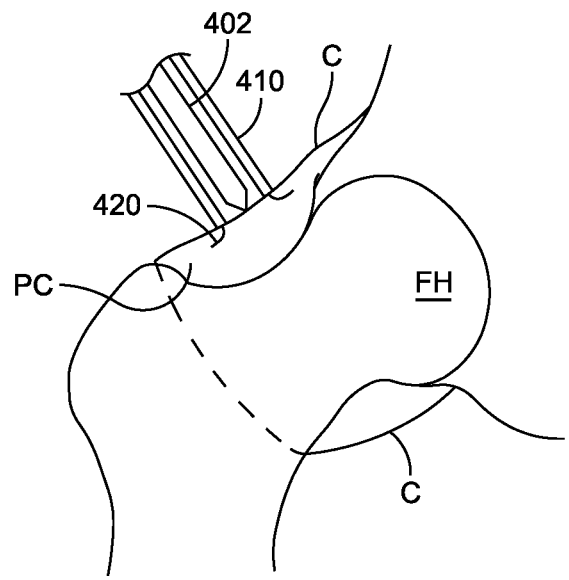

In FIG. 4C, sheath 410 is advanced over needle 402 to the surface of capsule C. In FIG. 4D, grasping members 420 engage capsule C by penetrating into capsule C to securely attach sheath 410. Grasping members 420 may engage capsule C by actuation of grasping members 420 at proximal flange 416 and/or by physical manipulation (e.g., rotating or pushing) of cylindrical body 412. Needle 402 may be replaced by a different needle more suitable for penetrating capsule C, such as a specialized trocar, or an additional cutting sheath may supplement needle 402, for example by inserting the cutting sheath between needle 402 and sheath 410.

Figure 4E:
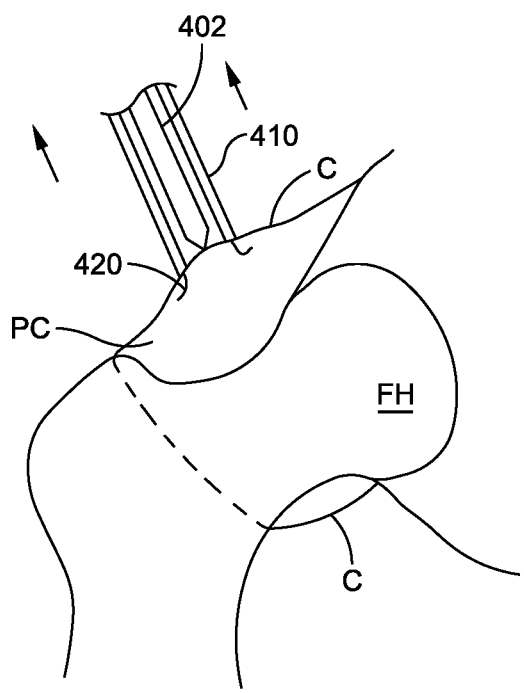

In FIG. 4E, sheath 410 is pulled away from the joint as shown by the directional arrows and maintained in that position. This causes capsule C to tent away from femoral head FH and increase the volume of peripheral compartment PC.

Figure 4F:
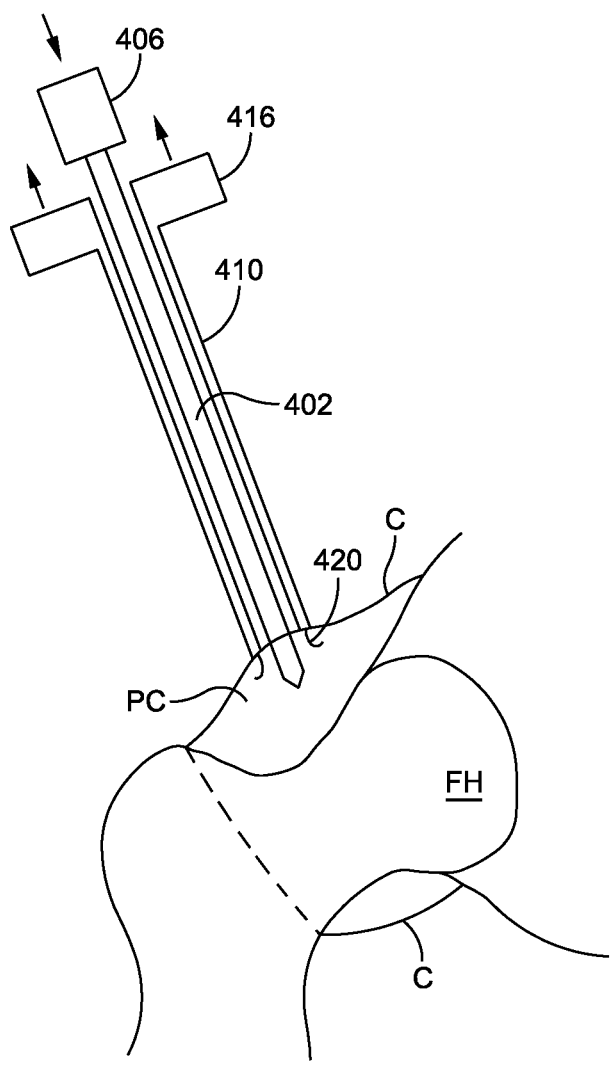

In FIG. 4F, needle 402 is used to penetrate capsule C. Needle 402 is advanced while sheath 410 tents capsule C by pulling sheath 410 away from femoral head FH. Needle 402 is unlikely to damage tissue underneath capsule C, as a significant gap is created between capsule C and femoral head FH. Accordingly, "popping" through capsule C and damaging tissue beyond is minimized. Needle 402 may threadably engage sheath 410, and be turned to advance through capsule C, which results in a controlled rate of penetration. If a sensor is present on needle 402, the sensor can provide an electrical signal to an indication system which indicates penetration of capsule C by a visual or aural indicator. Optionally, a distention fluid, such as saline, may be injected into peripheral compartment PC through needle 402 to distend capsule C.

Figure 5A:
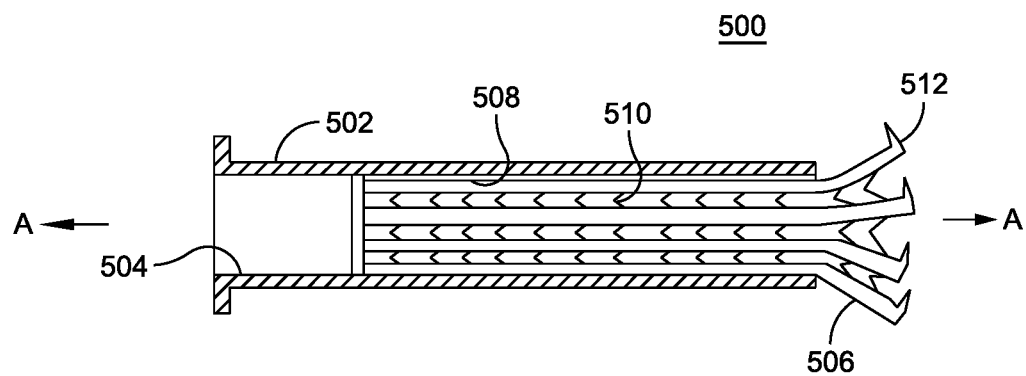
FIGS. 5A and 5B are cross-sectional and side views of a system for accessing the capsule of a joint, according to an embodiment of the invention.
Figure 5B:
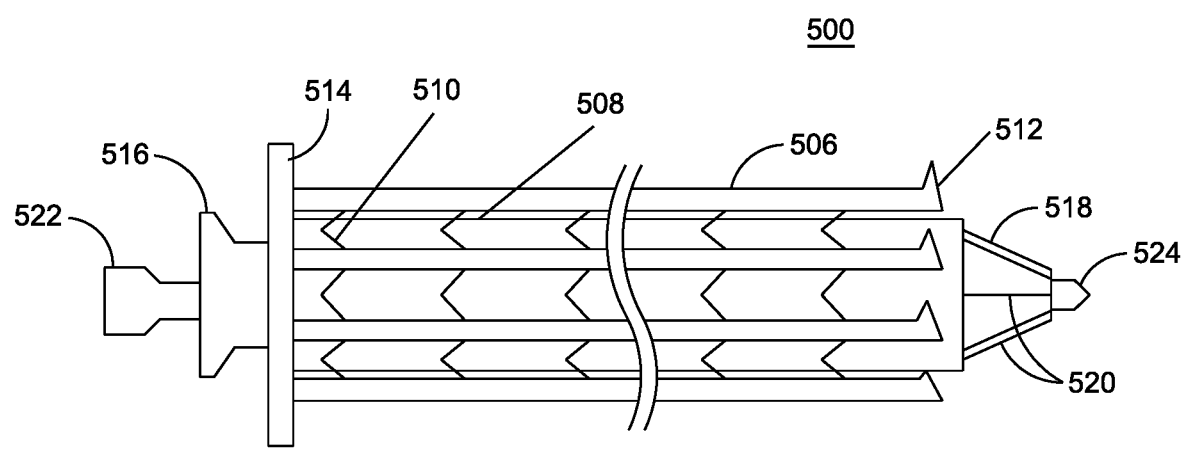

FIGS. 5A and 5B illustrates another system 500 for accessing the capsule of a joint. System 500 includes a tear away cannula or sheath 502. Sheath 502 is similarly configured to sheath 410. Sheath 502 has an inner lumen 504 in which is placed an expansion device 506, which is shown partially extending from sheath 502 (not shown). Before use, expansion device 506 is completely withdrawn within sheath 502. Expansion device 506 may be constructed similarly to a stent. Expansion device 506 includes a plurality of struts 508 connected by a plurality of expandable members 510. A plurality of grasping members 512 configured as tangential hooks are connected to struts 508. Other configurations of grasping members 512 may be used, as disclosed elsewhere herein. Expansion device 506 may be constructed from a metal, such as a shape memory or super elastic Ni—Ti, or a stainless steel.

FIG. 5B shows system 500 in an expanded configuration. A second cannula or sheath 514 is configured to slidably fit within expansion device 506. Expansion device 506 may be diametrically sized in an expanded configuration such that sheath 502 may be used as second sheath 514. A trocar 516 is slidably coupled with sheath 514. Trocar 516 includes a cutting tip 518. Cutting tip 518 may have a pyramid shape with a plurality of sharpened edges 520. Stylet 522 is slidably coupled within trocar 516. Stylet 522 includes a blunt distal tip 524 which extends past cutting tip 518.

Figure 5C:
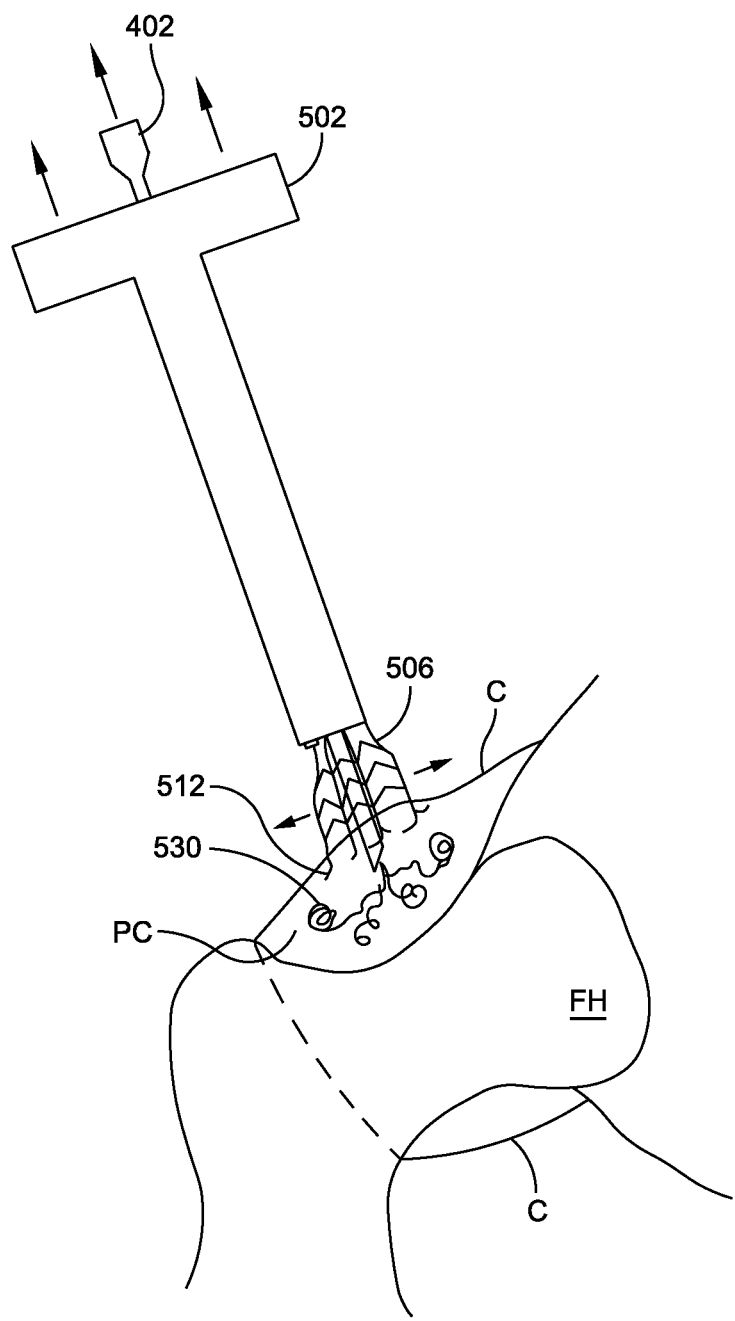
FIGS. 5C-5F are partial cross-sectional views of a hip joint being accessed by a system for accessing the capsule of a joint, according to an embodiment of the invention.

FIGS. 5C-5F illustrate a method of use for system 500, for accessing and penetrating the capsule of a joint. In FIG 5C, sheath 502 has been slightly withdrawn to expose grasping members 512 of expansion device 506. Grasping members 512 fixedly engage with capsule C by rotating the exposed grasping members 512 into capsule C. Needle 402 is then advanced relative to sheath 502 to puncture capsule C while sheath 502 tents capsule C by pulling sheath 502 away from femoral head FH. Grasping members 512 may exude a diametric expansion force on the capsule to expand and maintain the puncture site. Needle 402 may be used to inject capsule C with saline 530 to pressurize and distend capsule C. Needle 402 and sheath 502 may then be withdrawn from system 500.

Figure 5D:
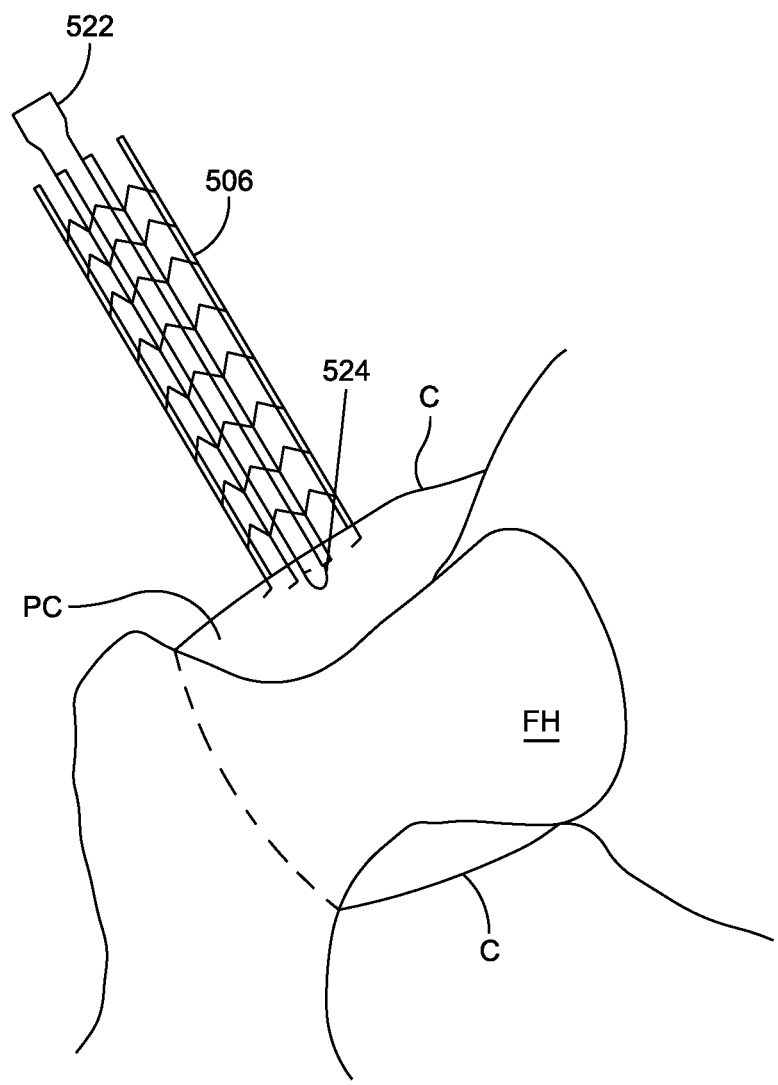

In FIG. 5D, expansion device 506 is fully expanded after sheath 502 has been removed. Stylet 522 is exchanged with needle 402 to enlarge and maintain the opening created by needle 402. Blunt distal tip 524 prevents damage to tissue beyond capsule C.

Figure 5E:
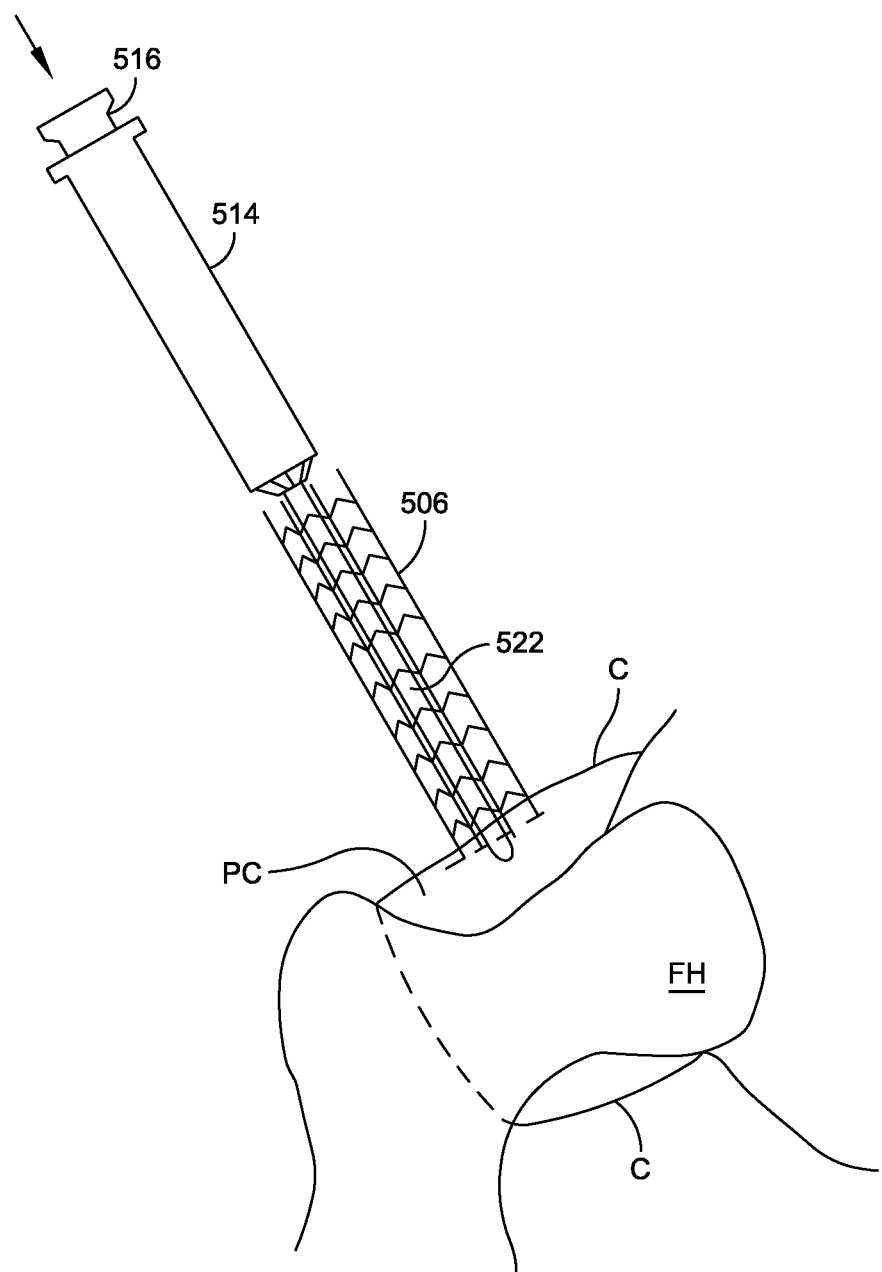
Figure 5F:
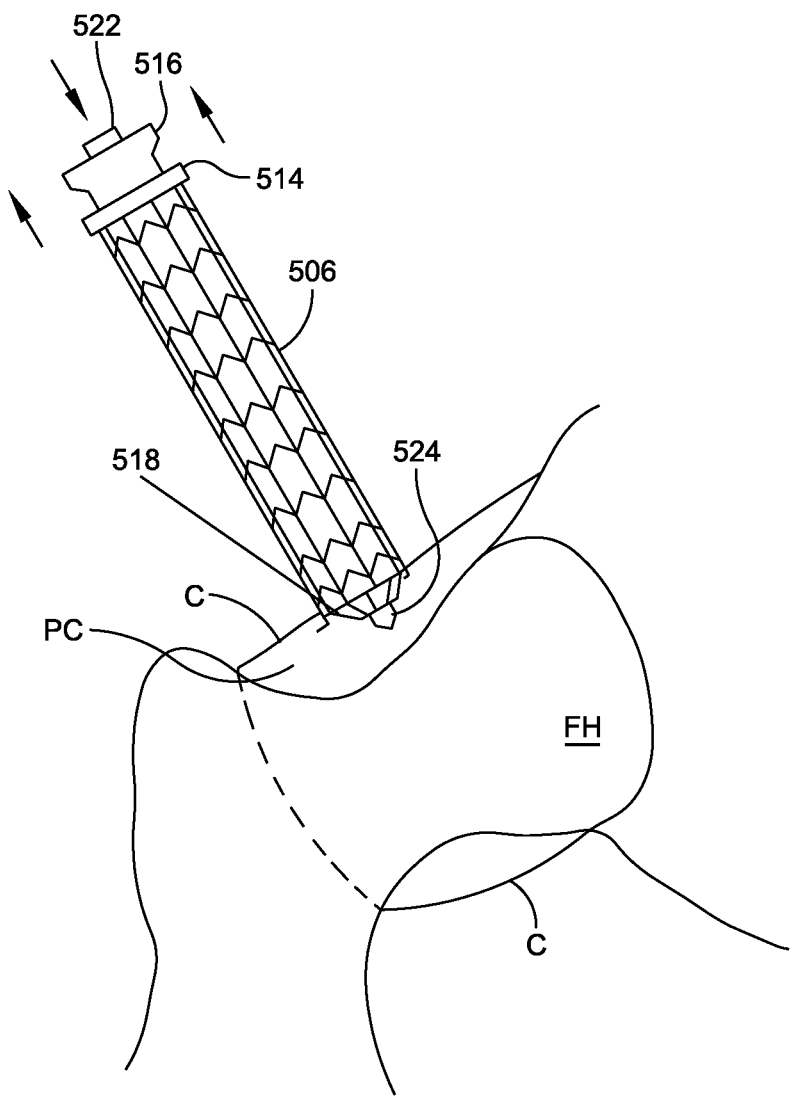

In FIG. 5E, sheath 514 and trocar 516 are introduced over stylet 522 and through expansion device 506. In FIG. 5F, sheath 514 and trocar 516 are advanced to penetrate capsule C. Prior puncturing of capsule C by needle 402 and stylet 522 allows trocar 516 to easily penetrate capsule C and expand the opening. Blunt distal tip 524 of stylet 522 prevents damage to tissue beyond capsule C, while trocar 516 is advanced. Trocar 516 and stylet 522 may then be removed to allow access by other devices through sheath 514.

Figure 6A:
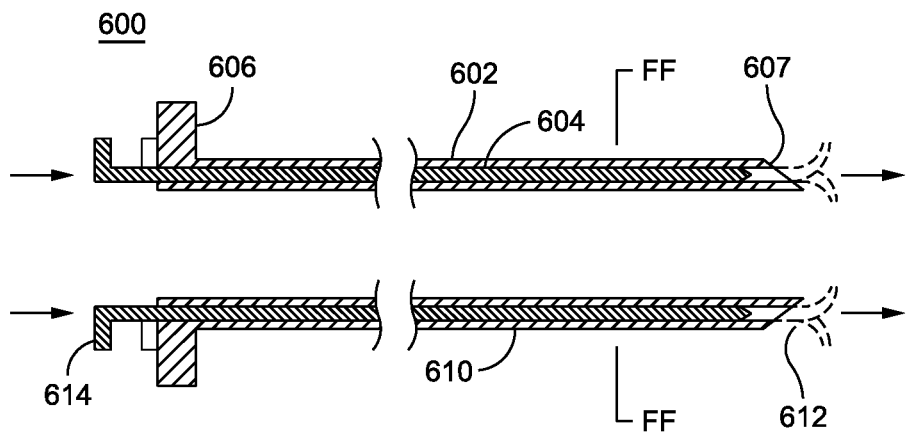
FIG. 6A is a side cross-sectional view of a system for accessing the capsule of a joint, according to an embodiment of the invention.

FIG. 6A illustrates a cannula or sheath 600, which may be used in conjunction with the systems disclosed herein. Sheath 600 includes a cylindrical body 602, a plurality of pathways 604 and a flange 606. A distal end 607 of cylindrical body 602 may be tapered. Pathways 604 extend axially within the sidewall of sheath 600 from its proximal end to its distal end. Sheath 600 may be constructed from a metal or a polymer material. Sheath 600 may be constructed as an expandable stent and include expandable zones between pathways 604. Pathways 604 may be circular or rectangular lumens.

A plurality of grasping members 610 are slidably housed within pathways 604. Grasping members 610 may comprise elongated needles with precurved distal ends 612. Distal ends 612 may be precurved to extend as hooks in an approximate inward or outward radial direction, tangential direction, or directions therebetween. Grasping members 610 may include respective proximal flanges 614. Proximal flanges 614 may be connected to each other by e.g., a ring-shaped member or slide independently from each other. Grasping members 610 may be constructed from a metal (e.g., stainless steel, shape-memory or super elastic Ni—Ti) or a polymer. Grasping members 610 may have circular or rectangular cross-sections.

In use, sheath 600 is used for securing to a capsule in accordance with the methods disclosed herein. Distal ends 612 of grasping members 610 may secure to the capsule by moving proximal flanges 614 in a distal direction such that distal ends 612 of grasping members 610 extend from pathways 604 and assume a precurved hook shape to securely engage capsule C. Distal ends 612 of grasping members 610 may disengage from capsule C by moving proximal flanges 614 in a proximal direction away from flange 606 of sheath 600. Accordingly., distal ends 612 of grasping members 610 will disengage from capsule C and withdraw back into pathways 604.

Figure 6B:
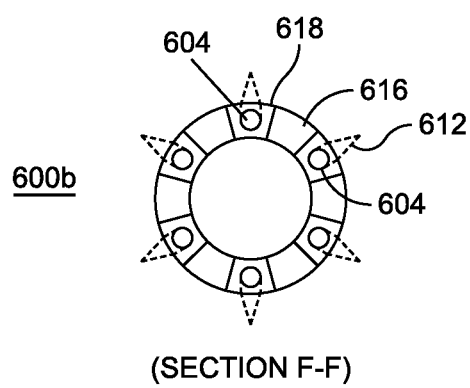
FIGS. 6B and 6C are longitudinal cross-sectional and partial side views, respectively, of a system for accessing the capsule of a joint, according to an embodiment of the invention.
Figure 6C:
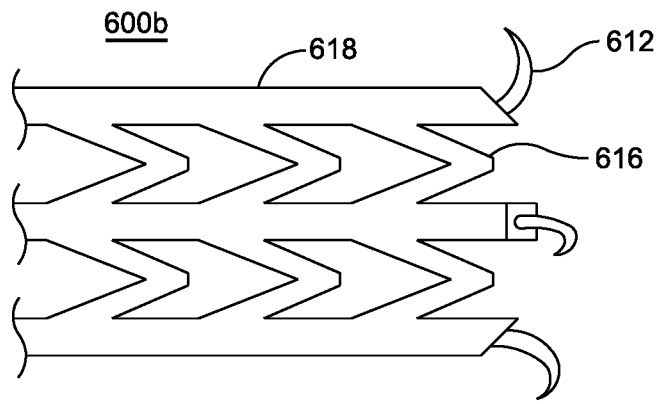

FIGS. 6B and 6C illustrate a sheath 600b according to an alternative construction of sheath 600. Sheath 600b includes a plurality of circumferentially expandable members 616 connected to axial struts 618. Struts 618 may house pathways 604 through which grasping members 610 (shown in FIG. 6A) slidably extend. Alternatively, precurved distal ends 612 may be welded or otherwise fixed to the distal ends of axial struts 618. Sheath 600b may be constructed from a malleable, elastic, super-elastic, or shape-memory material biased into a radially expanded configuration.

In use sheath 600b may be used as described with respect to sheath 600, Sheath 600b may first engage capsule C and then apply tension to capsule C by expanding expandable members 616. Sheath 600b may also combine the functionality of expansion device 506 and sheath 514, and be used in a similar manner to expand and maintain a passage in capsule C. Alternatively, sheath 600b may be placed within a tubular cannula or portal and allowed to expand against the inner wall thereof to hold it in place. Precurved distal ends 612 may extend distally of the distal end of sheath 600b and be used to grasp the capsular tissue to retain the cannula therein. Expandable members 616 may alternatively be a malleable material and expanded by applying internal force to sheath 600b, for example by expanding a balloon therein. Alternatively, expandable members 616 may be expanded by applying heat, in the case of shape-memory material, or by disengaging from a constrained configuration, in the case of an elastic or super-elastic material.

Figure 6D:
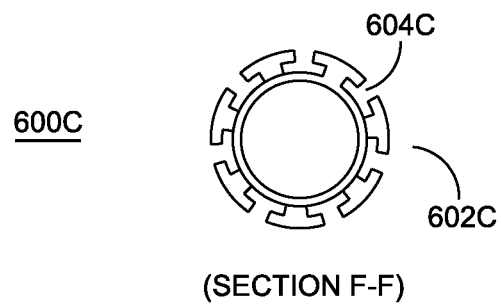
FIG. 6D is a longitudinal cross-sectional view of a system for accessing the capsule of a joint, according to an embodiment of the invention.
Figure 6E:
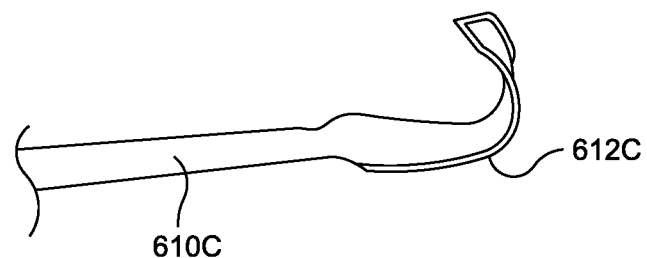
FIG. 6E is a partial perspective view of a grasping device, according to an embodiment of the invention.
Figure 6F:
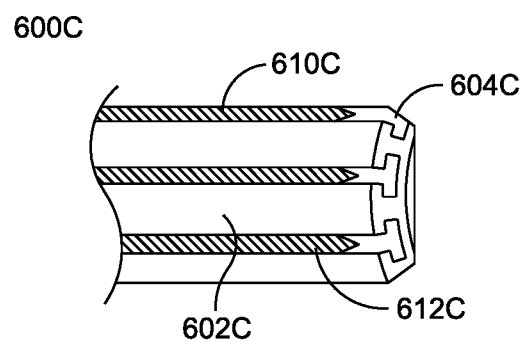
FIG. 6F is a partial side view of a system for accessing the capsule of a joint, according to an embodiment of the invention.

FIGS. 6D-6F illustrate a sheath 600c according to an alternative construction of sheath 600. Sheath 600c includes an extruded cylindrical body 602c with a plurality of longitudinal pathways 604c configured in cross-section as rectangular slots. Pathways 604c have an approximately rectangular cross-section and are partially open along the outer surface of cylindrical body 602c. Pathways 604c slidably house a plurality of grasping members 610c (FIGS. 6E and 6F).

Grasping members 610c are constructed from flattened wire and include precurved distal ends 612c. Precurved distal ends 612c are configured as flattened hooks.

In use, sheath 600c may be used as described with respect to sheath 600.

Figure 6G:
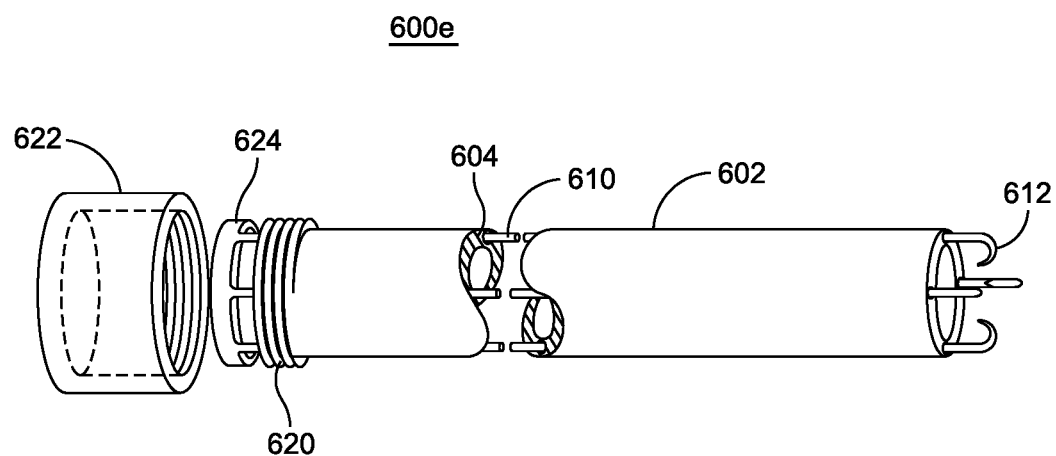
FIG. 6G is a side view of a system for accessing the capsule of a joint, according to an embodiment of the invention.

FIG. 6G illustrates a sheath 600e according to an alternative construction of sheath 600. Sheath 600e shares the general construction of sheath 600. Sheath 600e includes a proximally located threaded section 620 on a cylindrical body 602 which threadably couples to a cap 622. Grasping members 610 are joined by a proximally located ring 624, which is proximal to threaded section 620. A compression spring may be coupled between threaded section 620 and ring 624. Cap 622 may have a proximal opening. Cap 622 is diametrically sized to fit over and to be rotatable relative to ring 624. Cap 622 may be coupled to ring 624 so the two move axially together as the cap is screwed in. Cap 622 may comprise a shaped knob. A flange may be distally located from threaded section 620 on cylindrical body 602. The cap may be turned manually, or an electrical motor, control circuitry, and user interface may be functionally coupled to drive cap 622.

In use, sheath 600e may be used as described with respect to sheath 600. Cap 622 is coupled to threaded section 620 and turned, which causes cap 622 to move in a distal direction. As cap 622 is turned, it will eventually contact ring 624.. or if cap 622 is fixedly attached to ring 624. cap 622 and ring 624 will move in unison. Accordingly, cap 622 moves ring 62.4 in the distal direction while being turned to cause grasping members 610 to move within pathways 604, and eventually cause distal ends 612 of grasping members 610 to extend out of cylindrical body 602 and engage capsule C. Cap 622 may be turned to move in a proximal direction to cause grasping members 610 to withdraw into cylindrical body 602 and disengage from capsule C. While distal ends 612 are shown as being precurved inwardly, they may also be precurved in a radially-outward direction, or in a tangential direction.

Figure 7A:
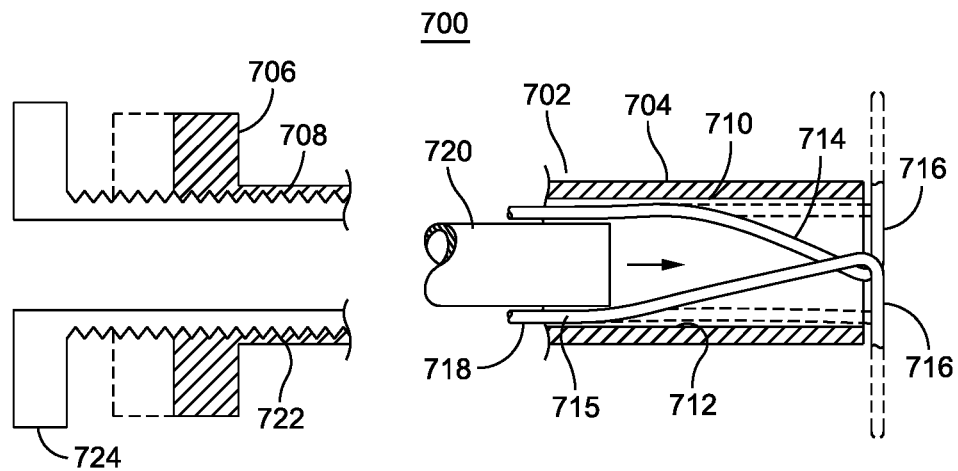
FIGS. 7A and 7B are side and longitudinal cross-sectional views, respectively, of a system for accessing the capsule of a joint, according to an embodiment of the invention.
Figure 7B:
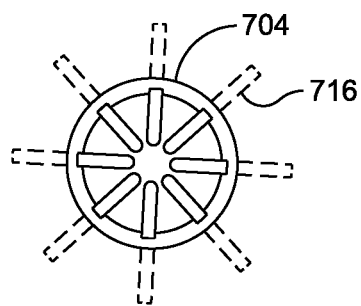

FIGS. 7A and 7B illustrate a system 700 for accessing the capsule of a joint. System 700 includes a cannula or sheath 702, generally constructed as the sheaths disclosed herein. Sheath 702 includes a cylindrical body 704 and a flange 706. Sheath 702 may include a proximally located threaded section 708.

An expansion device 710 is disposed within the inner lumen of sheath 702. Expansion device 710 includes a plurality of grasping members 714 which are biased radially inwardly. Grasping members 714 include elongated axial shafts 715 and respective distal ends 716 located externally to sheath 702 at the distal end thereof. Distal ends 716 of grasping members 714 may be configured as L-shaped hooks arranged to point radially outwardly. Grasping members 714 may be malleable, or resilient and biased radially inwardly. Proximal sections 718 of grasping members 714 may be fixedly attached to inner surface 712 of cylindrical body 704 of sheath 702, or grasping members 714 may be interconnected to create a tubular structure removably positionable in the lumen of sheath 702.

An inner shaft 720 is slidably disposed within expansion device 710. Inner shaft 720 is constructed as an elongated tube. Inner shaft 720 can include a threaded section 722 which threadably couples with threaded section 708 of sheath 702. Alternatively, inner shaft 720 can freely slide within sheath 702. Inner shaft 72( )includes a flange 724, which may be configured as a knob.

In use, system 700 can generally be used with a needle as described in the methods disclosed herein. The distal tip of sheath 702 is first advanced through a penetration in the capsule, which may be formed using a needle or trocar point placed through the inner lumen of inner shaft 720. Sheath 702 may then be securely attached to the capsule by advancing inner shaft 720 with respect to sheath 702. Turning flange 724 causes threaded section 722 to move in a distal direction, or in the case where no threaded sections are present, flange 724 can be simply slid towards flange 706. Distal movement of inner shaft 720 eventually causes inner shaft 720 to displace grasping members 714 radially outwardly. In turn, distal ends 716 expand in a radial direction to securely engage the interior wall of the capsule C.

Figure 8A:
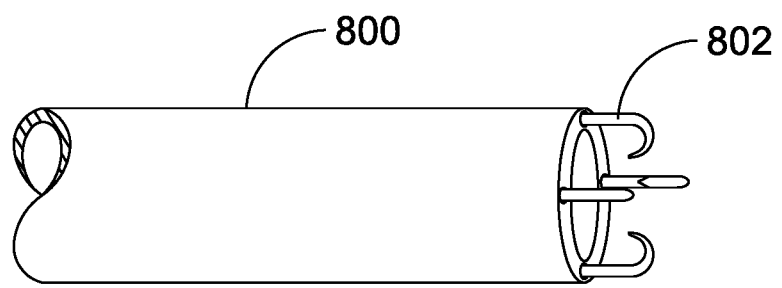
FIGS. 8A and 8B are side-perspective and cross-sectional views, respectively, of a system for accessing the capsule of a joint, according to an embodiment of the invention.
Figure 8B:
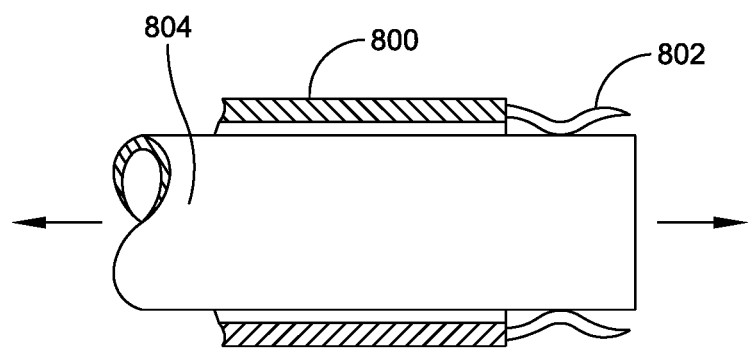

FIGS. 8A and 8B illustrate a cannula construction which may be used in conjunction with the systems disclosed herein. Sheath 800 includes a plurality of fixedly and distally attached grasping members 802. Grasping members 802 are configured as inwardly spring-biased hooks, as shown in FIG. 8A. Grasping members 802 may be constructed from a resilient, shape memory or super-elastic material, such as Ni—Ti. An inner tube 804 is slidably disposed within sheath 800, and outwardly displaces grasping members 802 in one configuration as shown in FIG. 8B.

In use, sheath 800 can generally be used in the manner described elsewhere in connection with the methods disclosed herein. Sheath 800 securely attaches to a capsule of a joint by withdrawing inner shaft 804 with respect to sheath 800. Proximal movement of inner shaft 804 allows grasping members 802 to move from the configuration shown in FIG. 8B to the configuration shown in FIG. 8A. Accordingly, when inner shaft 804 releases grasping members 802, grasping members 802 securely engage capsule C. A needle or other instrument can then be inserted through sheath 800 to puncture capsule C.

Figure 9A:
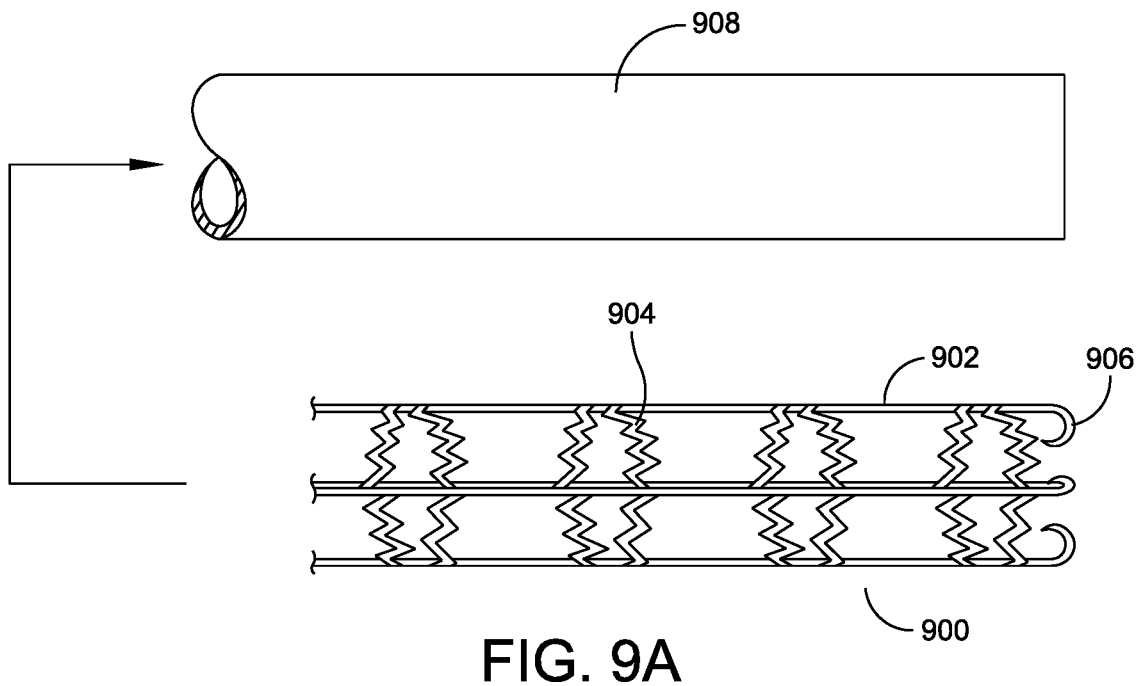
FIGS. 9A-9C are partial side views of a system for accessing the capsule of a joint, according to an embodiment of the invention.
Figure 9B:
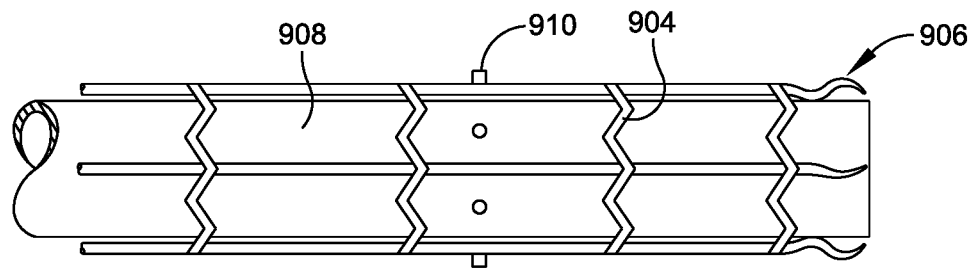
Figure 9C:
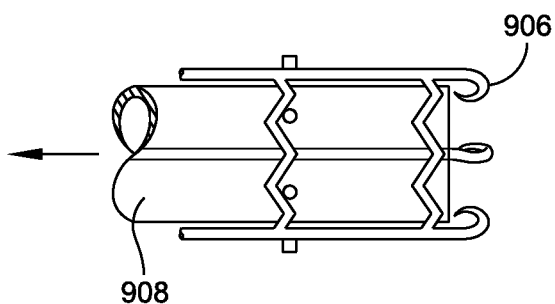

FIGS. 9A-9C illustrate a cannula construction which may be used in conjunction with the systems disclosed herein. An elongated stent 900 includes a plurality of struts 902 and resilient circumferentially expandable and contractible bands 904. Struts 902 include a plurality of respective grasping members 906 configured as inwardly spring-biased hooks, as shown in FIG. 9A. Elongated stent 900 may be constructed from a super-elastic material, such as Ni—Ti. Elongated strut 900 is coupled to a cannula or sheath 908. Sheath 908 is generally constructed as the sheaths disclosed herein. A plurality of travel limiters 910 may extend from sheath 908. Elongated stent 900 is biased into a radially contracted configuration and is coupled to sheath 908 by forcibly expanding elongated stent 900 and inserting sheath 908 therein, as shown in FIG. 9B. Accordingly, elongated stent 900 securely holds onto sheath 908.

In use, grasping members 906 securely attach to the capsule of a joint by placing sheath 908 into contact with the outer surface of the capsule, and advancing elongated stent 900 relative to sheath 908. When grasping members 906 have cleared the distal end of sheath 908, grasping members 906 are allowed to move from the configuration shown in FIG. 9B to the configuration shown in FIG. 9C. Accordingly, when sheath 908 releases grasping members 906, grasping members 906 securely engage capsule C. Travel limiters 910 prevent further movement of elongated stent 900 with respect to sheath 908. A needle or other instrument can then be placed through sheath 908 to puncture capsule C and perform procedures therein.

FIGS. 10A-10D illustrate a cannula construction which may be used in conjunction with the systems disclosed herein. A cannula or sheath 1000 includes an elongated inner tube 1005 including a plurality of radial arranged grasping members 1010 extending therefrom. Grasping members 1010 may be constructed from a resilient or malleable material and include tapered, straight/flat, or duckbill configurations as shown from top to bottom in FIG. 10B. An outer tube 1015 is rotatably engaged over inner tube 1005. Outer tube 1015 includes a plurality of slots 1020 (FIG. 10D) which are slidably engaged with grasping members 1010. Outer tube 1015 is diametrically sized to fit over inner tube 1005 and rotationally movable from a first position in which grasping members 1010 are radially collapsed, as shown in FIG. 10A, to a second position in which grasping members 1010 are radially extended, as shown in FIGS. 10C and 10D. Outer tube 1015 and inner tube 1005 can include a locking mechanism, such as a button extending from inner tube 1005 which locks into an opening of outer tube 1015, for maintaining the configuration shown in FIG. 10D.

In use, sheath 1000 can generally be used with a needle as described in the methods disclosed herein. Sheath 1000 is placed against the capsule and a needle may be positioned through sheath 1000 to puncture capsule C. The tip of sheath 1000 is then inserted into the capsule. Grasping members 1010 securely attach to capsule C of a joint by rotating inner tube 1005 and outer tube 1015 with respect to each other. Accordingly, either inner tube 1005 or outer tube 1015 is held stationary, and the other is rotated. This action causes grasping members 1010 to extend from slots 1020 and securely engage the inner surface of capsule C. Rotating either inner tube 1005 or outer tube 1015 back into its original position causes grasping members 1010 to withdraw back into sheath 1000 and disengage from capsule C.

Capsular Distention

Further embodiments of the invention include distension devices which are used to distend capsule C and enlarge peripheral compartment PC. It should be understood that the distension devices disclosed herein can be used with any of the systems disclosed herein to access capsule C.

FIG. 11A illustrates a system 1100 for accessing and distending the capsule of a joint. System 1100 includes a cannula or sheath 1102, which is configured similarly to the sheaths disclosed herein. An expansion device 1104 is coupled within sheath 1102. Expansion device 1104 includes a plurality of grasping members 1106 shown in an exposed position. Expansion device 1104 may generally be configured similarly to the expansion devices disclosed herein.

A balloon device 1108 is slidably disposed within sheath 1102. Balloon device 1108 includes an elongated shaft 1110 with a distally positioned balloon 1112. Shaft 1110 may be constructed from a flexible or stiff material, such as a metal or polymer. Shaft 1110 may include at least one lumen. Shaft 1110 can be circular in cross-section and have an outer diameter sized to be exchangeable with the needles disclosed herein, for example 18-27 gauge. Balloon 1112 may be constructed from a non-compliant (e.g., 0-10% compliance range) thin-walled material such as polyethylene terephthalate (PET), or from a semi-compliant (e.g., 10-20% compliance range) thin-walled material, such as PET, nylon, and polyurethane. Balloon 1112 may be capable of withstanding high pressures (e.g., up to 400 psi), and include reinforcement features, such as integrated woven fibers, to help prevent bursting. Balloon 1112 can have a wall thickness ranging from 0.0001 to 0.0006 inches, and may also have multiple layered wall, e.g., 2-ply or 3-ply, with the layers either adhered to each other or not. Balloon 1112 is shown in an expanded configuration and may have an expanded diameter of 5 to 20 millimeters. Balloon 1112 may be folded or collapsed into an unexpanded configuration to have an effective diameter which is roughly equivalent to or slightly larger than the outer diameter of shaft 1110. Balloon 1112 may utilize various shapes and sizes other than the generally spherical shape shown, such as spherical, donut, cylindrical, oval, curved, conical or kidney shapes.

An atraumatic tip 1114 extends from balloon 1112. Atraumatic tip 11114 can be constructed from a soft material, such as rubber. A connector 1116 for coupling to an inflation device, such as a syringe or angioplasty balloon inflation device, is proximally located on shaft 1110. Connector 1116 is fluidly coupled to balloon 1112.

FIG. 11B illustrates a system 1100b for accessing and distending the capsule of a joint. System 1100b is largely identical to system 1100 except that in system 1100b, sheath 1102b has hinged sections 1118b. Hinged sections 1118b provide sheath 1102b with a long configuration, and a short configuration as shown. Hinged sections 1118b radially and outwardly expand into flanges in the short configuration. These flanges are configured to engage the outer wall of the capsule while grasping members 1106 engage the inner wall to sandwich the capsular wall therebetween, thereby firmly retaining sheath 1102b. A clip 1120 may attach to a section 1122 between expansion device 1104 and sheath 1102b, to prevent relative movement therebetween and maintain sheath 1102b in the short configuration.

Figure 11C:
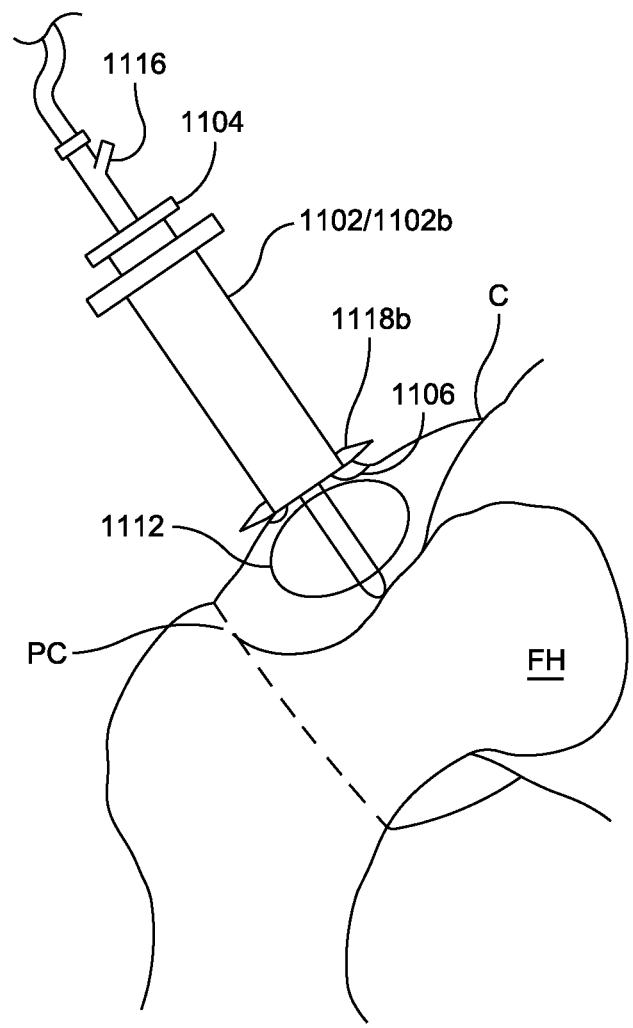

FIG. 11C illustrates a method of use for systems 1100, 1100b, for accessing and distending the capsule of a joint. In FIG. 11C, system 1100 or 1100b has already been used to puncture capsule C, as similarly described herein. In the case of system 1100b, hinged sections 1118b can be moved to the short configuration to form a flange which holds capsule C between hinged section 1118b and grasping members 1106. Balloon device 1108 is then advanced into peripheral compartment PC and balloon 1112 is expanded to distend capsule C. Balloon 1112 can be maintained in this position over time to stretch capsule C. Accordingly, peripheral compartment PC is enlarged to enable access by other devices. Balloon 1112 may then be deflated and removed from shaft 1110. Alternatively catheters or other devices may be placed through an inner lumen of balloon device 1108, distally of balloon 1112 and into the peripheral or central compartments of the joint to perform interventional procedures therein.

Figure 12A:
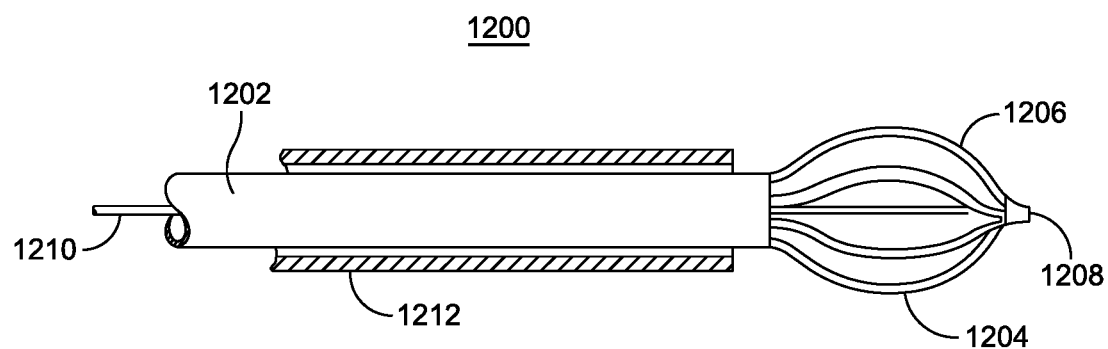

FIG. 12A illustrates a basket device 1200 for distending the capsule of a joint after accessing the capsule in accordance with systems and methods described herein. Basket device 1200 includes an elongated shaft 1202. Shaft 1202 may be constructed from a flexible or stiff material, including metals or polymers. Shaft 1202 may include at least one lumen. Shaft 1202 can be circular in cross-section and have an outer diameter sized to be exchangeable with the needles disclosed herein, for example 18-27 gauge. An expandable basket 1204 extends distally from shaft 1202. Basket 1204 includes a plurality of basket leaves 1206 circumferentially arranged around shaft 1202. Basket leaves 1206 can be pre-shaped to bow outwardly, or naturally assume a straightened configuration. Basket leaves 1206 may be constructed from a metal, such as such as super-elastic Ni—Ti or stainless steel, or from a polymer material. An atraumatic tip 1208 joins basket leaves 1206 to a pull wire 1210 which proximally extends within shaft 1202.

Figure 12B:
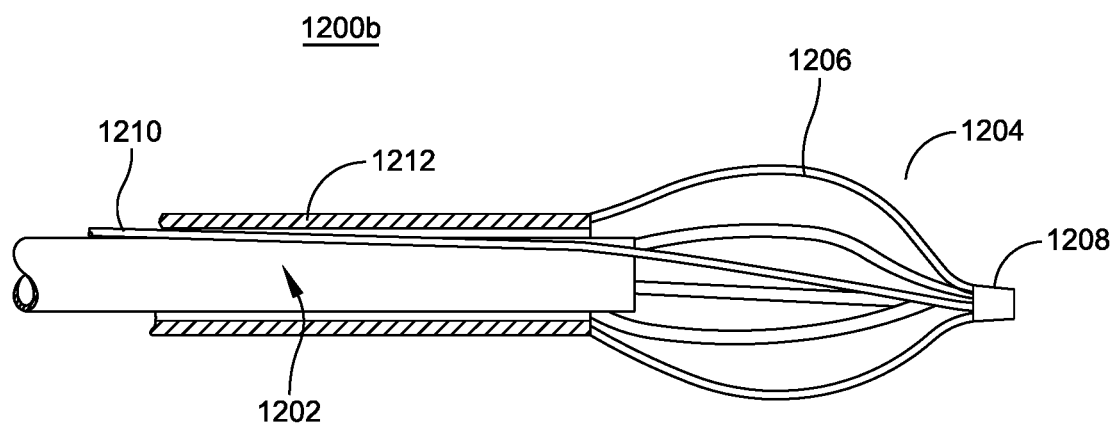

FIG. 12B shows an alternatively constructed basket device 1200*b* where pull wire 1210 is positioned outside of shaft 1202.

In use, basket device 1200 or 1200*b* may be used to distend capsule C in a similar manner to balloon device 1108 of systems 1100 and 1100*b*. Basket 1204 is advanced within a cannula or sheath 1212 and into peripheral compartment PC. Pull wire 1210 is then pulled proximally with respect to shaft 1202 to expand basket leaves 1206 and distend capsule C. In the case where basket 1204 is pre-shaped, pull-wire 1210 is initially moved distally with respect to shaft 1202 to collapse basket leaves 1206 so that basket 1204 can be advanced down sheath 1212 and into peripheral compartment PC. Pull wire 1210 is then released (or pulled proximally) to expand basket leaves 1206 and distend capsule C. Other devices may access peripheral compartment PC through shaft 1202.

Figure 12C:
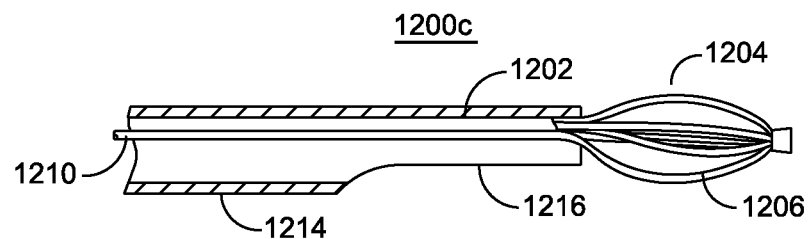
Figure 12D:
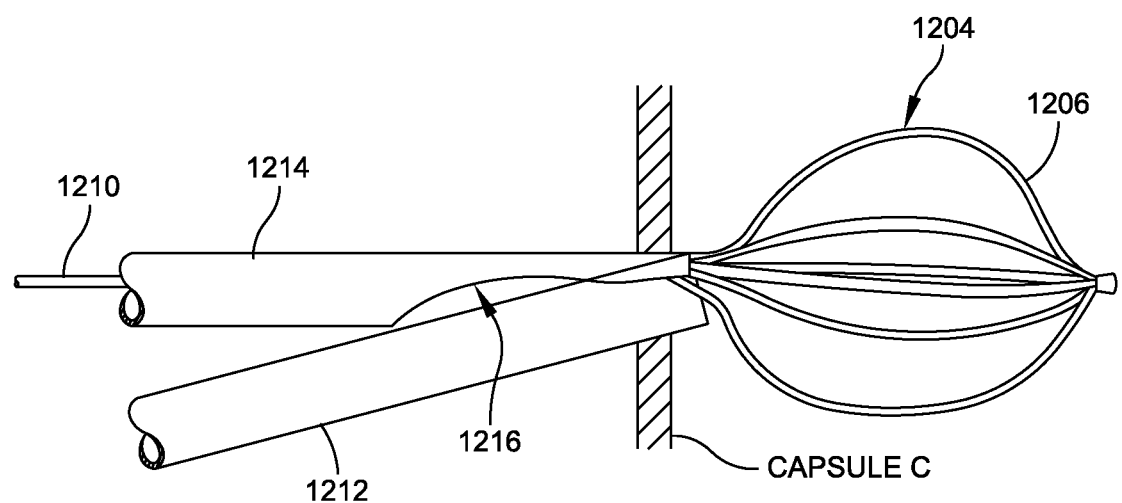

FIGS. 12C and 12D illustrate a basket device 1200*c* for distending capsule C. Basket device 1200*c* comprises a tubular shaft 1214 and an expandable basket 1204 coupled to its distal end. Basket 1204 comprises a plurality of elongated leaves 1206 or tines of a resilient material fixed at their proximal ends to the inner surface 1202 of shaft 1214. Shaft 1214 includes a cutout portion 1216 in its sidewall near the distal end thereof configured to receive a second shaft, cannula, or instrument introduced from a laterally offset location as described below. A pull wire 1210 is fixed at its distal end to the distal end of basket 1204 and extends proximally through the interior of shaft 1214. Exerting tension on pull wire 1210 causes leaves 1206 to bow outwardly into a radially expanded configuration.

In use. basket device 1200*c* is advanced through a penetration in the capsule to insert basket 1204 inside capsule C, as shown in FIG. 12D. Basket 1204 may then be expanded to distend the capsule. A sheath, cannula, or other instrument 1212 may then be introduced alongside shaft 1214 and positioned through cutout portion 1216 so that the distal end of instrument 1212 is within the expanded basket 1204. Cutout portion 1216 allows shaft 1214 and instrument 1212 to be arranged at a relatively shallow angle with respect to each other. Other devices can be inserted through instrument 1212 to perform procedures in the peripheral or central compartments while basket device 1200*c* maintains distension of capsule C.

Figure 12E:
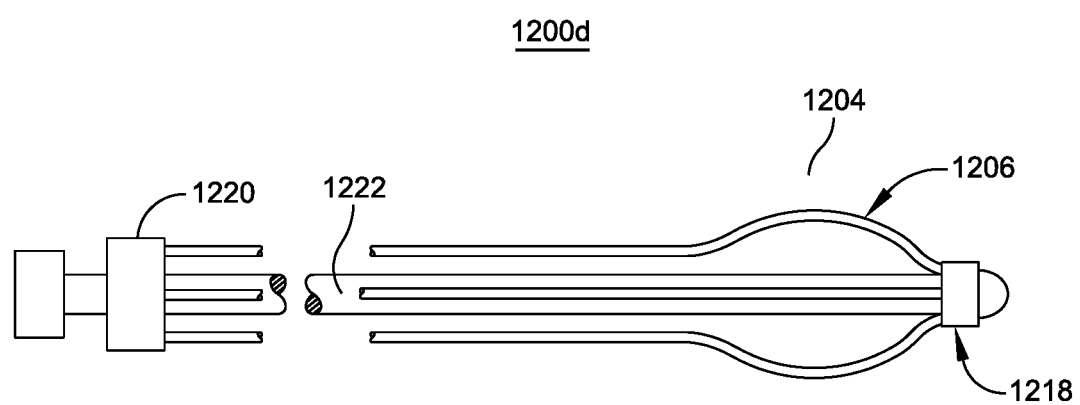

FIG. 12E illustrates a basket device 1200*d* for distending a capsule. Basket device 1200*d* includes a plurality of basket leaves 1206 which are pre-shaped into basket 1204, as shown. A distal ring 1218 distally joins basket leaves 1206, while a proximate ring 1220 proximally joins basket leaves 1206. An elongated shaft 1222 is removably coupled to distal ring 1218 and slides within proximate ring 1220. A locking mechanism can be functionally coupled to proximate ring 1220 and shaft 1222 to lock proximate ring 1220 and shaft 1222 to each other. Alternatively, basket leaves 1206 may be normally biased into a straight configuration and bowed outwardly by exerting tension on shaft 1222.

In use, shaft 1222 is moved distally with respect to proximate ring 1220 to cause basket 1204 to unbow and move towards shaft 1222. This position reduces the effective diameter of basket 1204 and allows basket device 1200*d* to be advanced into instrument 1212 (shown in FIGS. 12A, 12B and 12D) and into peripheral compartment PC. Once basket 1204 is within peripheral compartment PC, shaft 1222 is moved proximally with respect to proximate ring 1220 which causes basket 1204 to bow and expand peripheral compartment PC. Shaft 1222 can then be removed from instrument 1212. Accordingly, as the interior of instrument 1212 is unoccupied by shaft 1222, other devices can simultaneously be inserted into instrument 1212 while basket device 1200*d* maintains distension of capsule C. Optionally, shaft 1222 may be tubular so as to allow the introduction of catheters or instruments therethrough.

FIGS. 13A and 13B illustrate a piston device 1300 for distending the capsule of a. joint. Piston device 1300 includes an elongate body 1302. Elongate body 1302 can house a pneumatic or hydraulic cylinder 1304 or electrical motor, such as a step-motor. Pneumatic cylinder 1304 is moveable within elongate body 1302 and is also fluidly sealed therein. A moveable shaft 1306 extends from pneumatic cylinder 1304 and elongate body 1302. Moveable shaft 1306 has a range of motion between a fully extended position and a fully unextended position. Atraumatic bumpers 1308 are connected to one end of moveable shaft 1306 and to one end of elongate body 1302. A pressure hose 1310 is fluidly connected to elongate body 1302. Alternatively, an electrical cable can be connected to elongate body 1302 if an electrical motor is housed therein. An elongated applicator device 1312 is detachably coupled to one of the atraumatic bumpers 1308 at a distal cup 1314. A push rod 1316 is moveably housed within applicator device 1312 and can moveably extend into distal cup 1314.

FIG. 13C illustrates a method of use for piston device 1300 to distend capsule C of a joint. In FIG. 13C, capsule C has already been punctured in accordance with the methods disclosed herein. Applicator device 1312 is advanced into a sheath to deposit piston device 1300 within peripheral compartment PC. Actuation of push rod 1316 detaches piston device 1300 from distal cup 1314. Piston device 1300 may be placed within peripheral compartment PC, so that atraumatic bumpers 1308 are positioned at capsule C and greater trochanter T, or at capsule C and femoral neck FN, or in various other positions. Pressure hose 1310 is coupled to a pressure source and pressurized. Accordingly, the increased pressure causes pneumatic cylinder 1304 to move moveable shaft 1306 to the fully extended position and distend capsule C between atraumatic bumpers 1308. Alternatively, an electrical signal is sent to piston device 1300, if an electrical motor is used, to move moveable shaft 1306 to the fully extended position and distend capsule C between atraumatic bumpers 1308.

FIG. 14A illustrates a distention device 1400 for distending the capsule of a joint. Distention device 1400 includes an elongate shaft 1402. An atraumatic foot 1404 is distally connected to shaft 1402. Atraumatic foot 1404 may be curved to fit the profile of portions of a joint, such as femoral neck FN. Shaft 1402 includes a threaded section 1406 which is threadably coupled to a knob 1408. Knob 1408 is rotatably coupled to a sheath 1410. Sheath 1410 can assume the general construction of sheaths disclosed herein.

FIG. 14B illustrates a method of use for distention device 1400 to distend capsule C of a joint. In FIG. 14B, sheath 1410 has been securely attached to capsule C, and capsule C has already been punctured in accordance with the methods described herein. Shaft 1402 is advanced within sheath 1410 into peripheral compartment PC to contact atraumatic foot 1404 against femoral neck FN. Knob 1408 is then rotated until it contacts and couples with secured sheath 1410. Knob 1408 is continually rotated to cause shaft 1402 to move distally with respect to knob 1408 and sheath 1410. Accordingly, atraumatic foot 1404 of shaft 1402 pushes against femoral neck FN, which causes capsule C to stretch and distend between femoral neck IN and secured sheath 1410.

FIG. 15A illustrates a system 1500 for distending the capsule of a joint. System 1500 includes a first elongated strap 1502 and a second elongated strap 1504. Straps 1502., 1504 may be constructed from a flexible cord, such as a braided polymer rope. Straps 1502, 1504 may each include a stiffening core wire 1506. Core wire 1506 can be laterally stiffer than the braided rope. Core wire 1506 can be comprised from a preshaped, super-elastic alloy to angle a distal portion of each strap at a predefined angle, for example 30 to 90 degrees, as shown by the dotted lines. Straps 1502, 1504 each include a distally connected magnetic member 1508a, 1508b. The straps are generally identical except for the configuration of the magnetic members 1508a, 1508b. Magnetic members 1508a, 1508b can be magnets with distally positioned opposite polarities. One magnetic member can be a ferromagnetic substance such as steel, while the other can be a magnet. Magnetic members 1508a, 1508b can include rare-earth magnets, such as neodymium magnets. The magnetic members 1508a, 1508b are shown configured as cylinders, but can include dissimilar and coupling shapes such as a cup and ball arrangement. Straps 1502, 1504 are diametrically configured to be slidable within a cannula or sheath 1510.

Figure 15B:
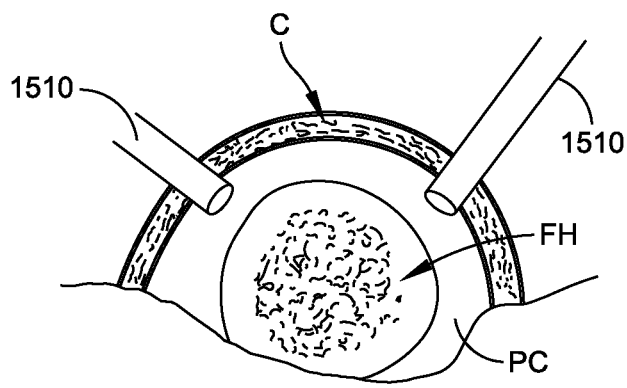

FIGS. 15B-F illustrate system 1500 in use for distending capsule C of a joint. In FIG. 15B, two sheaths 1510 are made to access the peripheral compartment beyond capsule C. Sheaths 1510 can access the capsule in accordance with the methods disclosed herein. Capsule C can also be pre-distended in accordance with the methods disclosed herein.

Figure 15C:
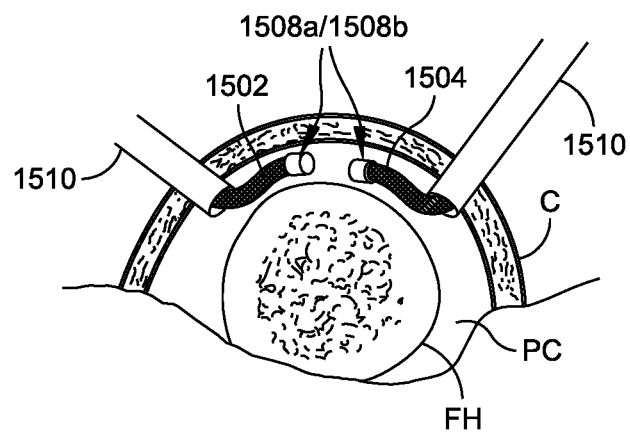

In FIG. 15C, straps 1502, 1504 are respectively advanced within the sheaths into peripheral compartment PC. Straps 1502, 1504 are manipulated to guide magnetic members 1508a, 1508b to unite. Core wires 1506, if present, can aid to steer magnetic members 1508a, 1508b towards each other. Once magnetic members 1508a, 1508b are guided into general vicinity, a magnetic force will cause them to magnetically couple to join the two straps. Accordingly, straps 1502, 1504 become united.

Figure 15D:
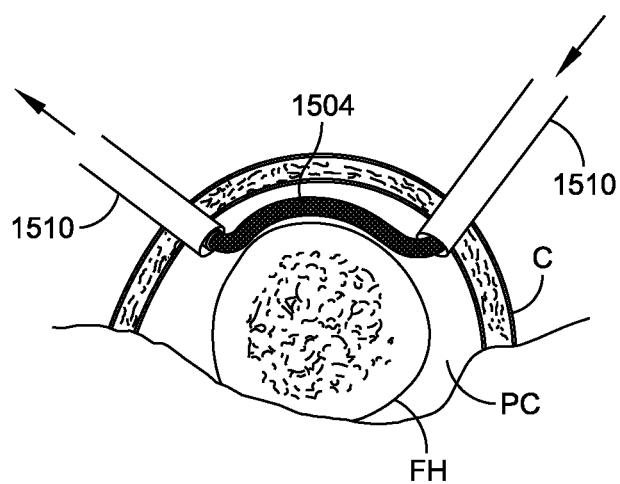

In FIG. 15D, strap 1502 is pulled out of its respective sheath 1510. Straps 1502, 1504 are magnetically united which causes strap 1504 to follow as strap 1502 is pulled. Accordingly, a mid-section of strap 1504 is made to occupy peripheral compartment PC. Sheaths 1510 can then be removed from capsule C.

Figure 15E:
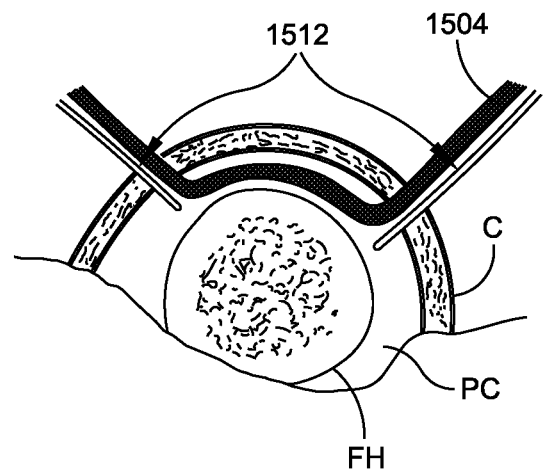

In FIG. 15E, two guide probes 1512 are advanced into the openings where sheaths 1510 previously resided. Sheaths 1510, or other sheaths, can be guided over guide probes 1512 to be guided back into the openings adjacent to strap 1504.

Figure 15F:
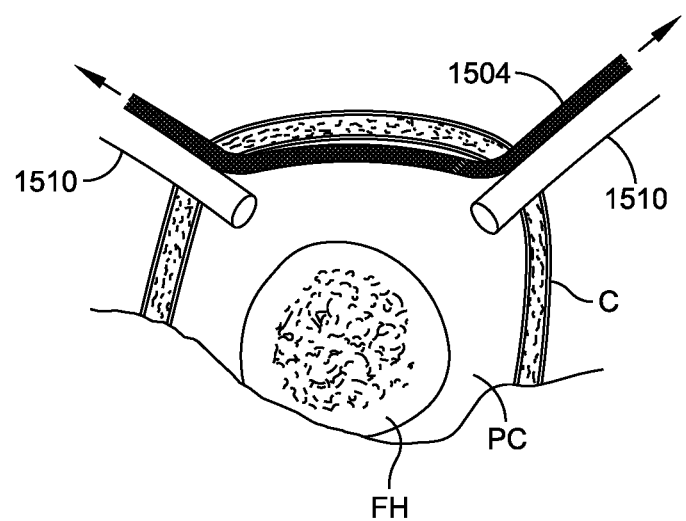
Figure 16:
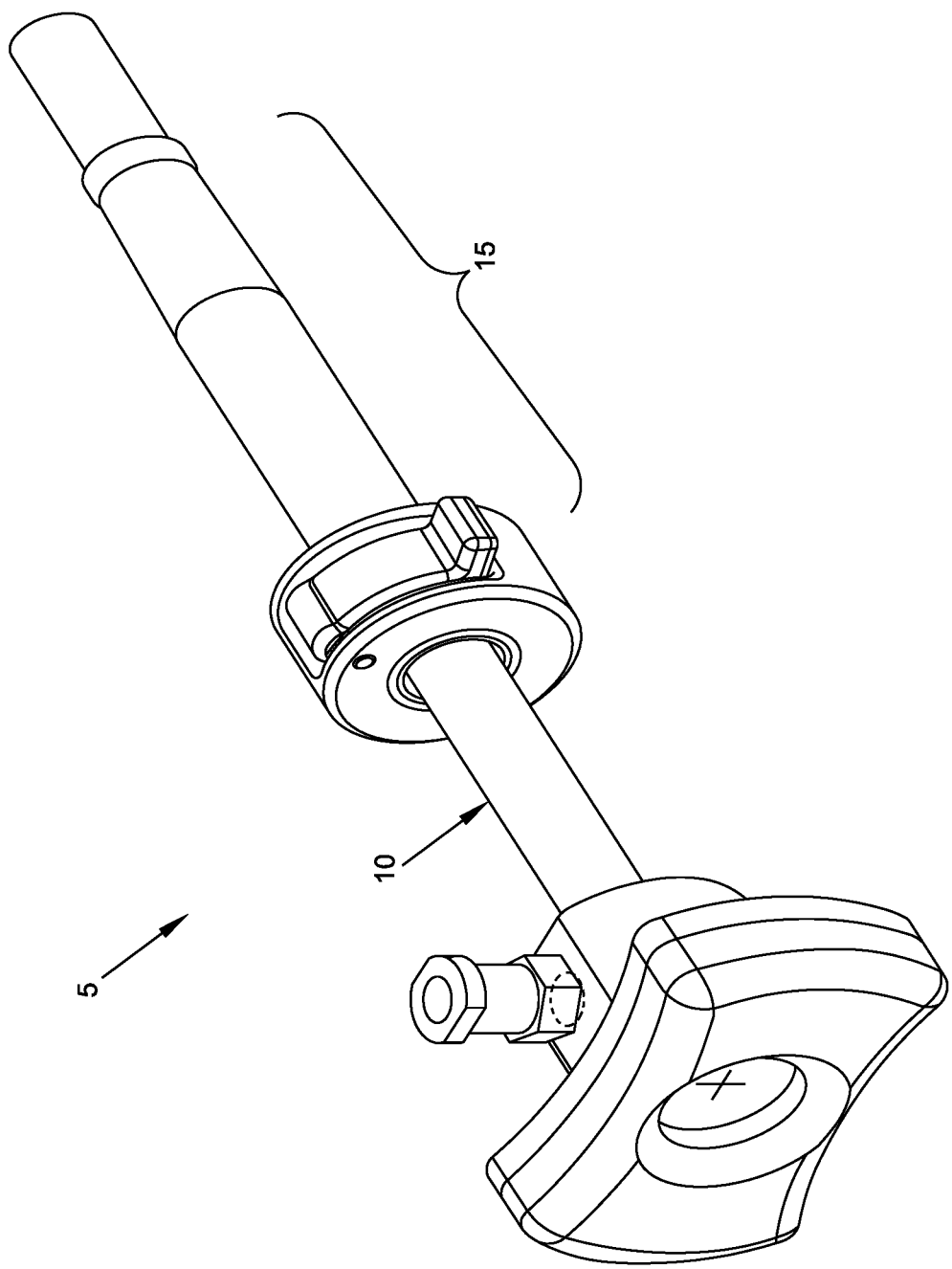

In FIG. 15F, the ends of strap 1504 are pulled away from the joint to distend capsule C, as shown. Tension may be continuously maintained on strap 1504 by a traction mechanism to maintain capsule C in the distended position. Other devices may then access peripheral compartment PC using sheaths 1510 for a following procedure. Strap 1504 may be removed by discontinuing application of tension and pulling strap 1504 out of one the openings. Strap 1504 may be cut at a location near the joint to aid in removal.

Additional Methods and Apparatus for Accessing the Interior of a Hip Joint and Increasing the Workspace Adjacent to the Head of the Femur and/or the Acetabulum During an Arthroscopic Hip Procedure Access Cannula with Capsulary Lock The present embodiment is directed to a cannula that allows quick access to the interior of the hip joint while also providing a capsulary lock mechanism for selectively locking the distal end of the cannula within the capsule of the hip and/or creating additional workspace at the surgical site.

Looking next at FIGS. 16-24, there is shown a locking access cannula 5 formed in accordance with the present invention. Locking access cannula 5 generally comprises a cannula sub-assembly 10 and a locking sub-assembly 15 for mounting over cannula sub-assembly 10.

Figure 17B:
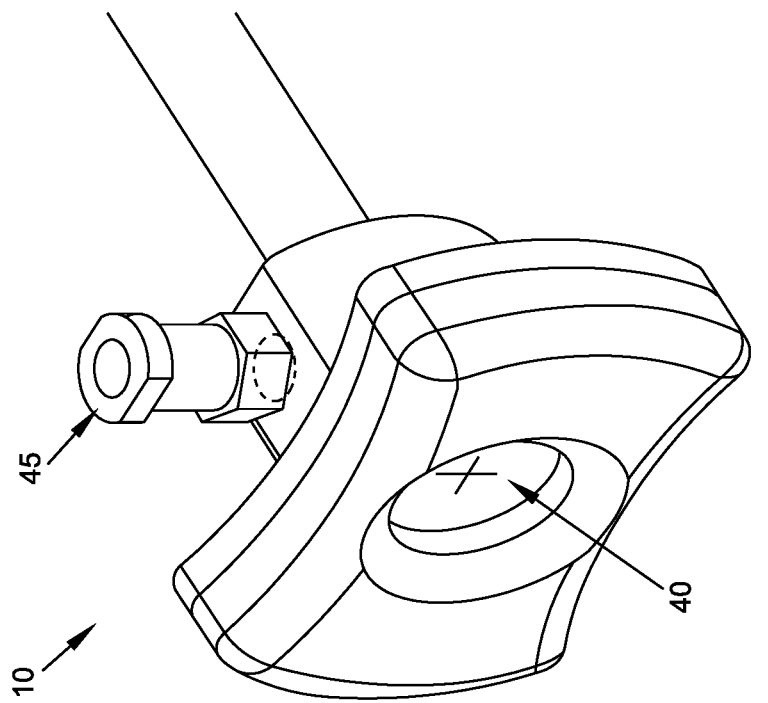
Figure 17A:
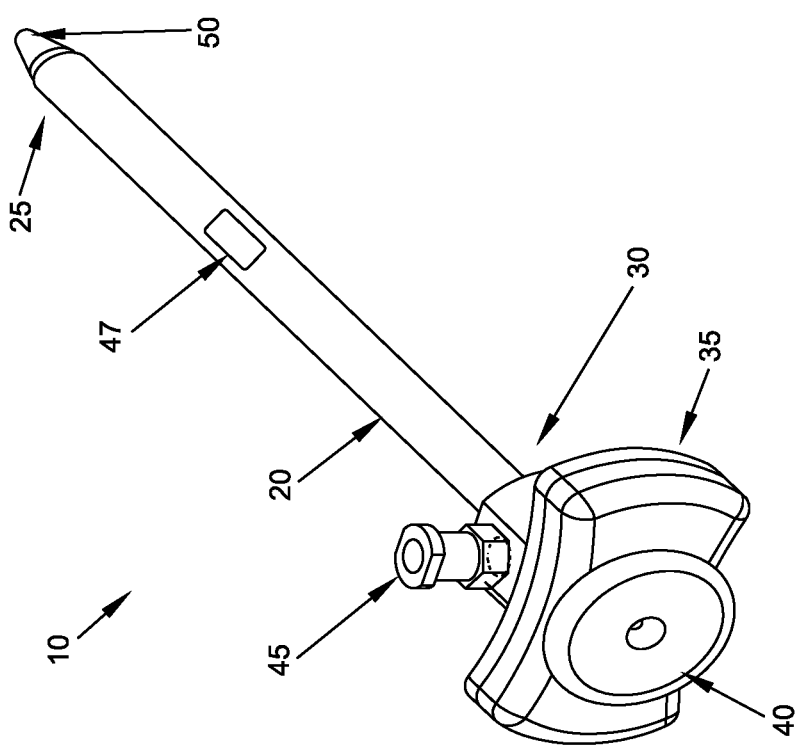
Figure 18:
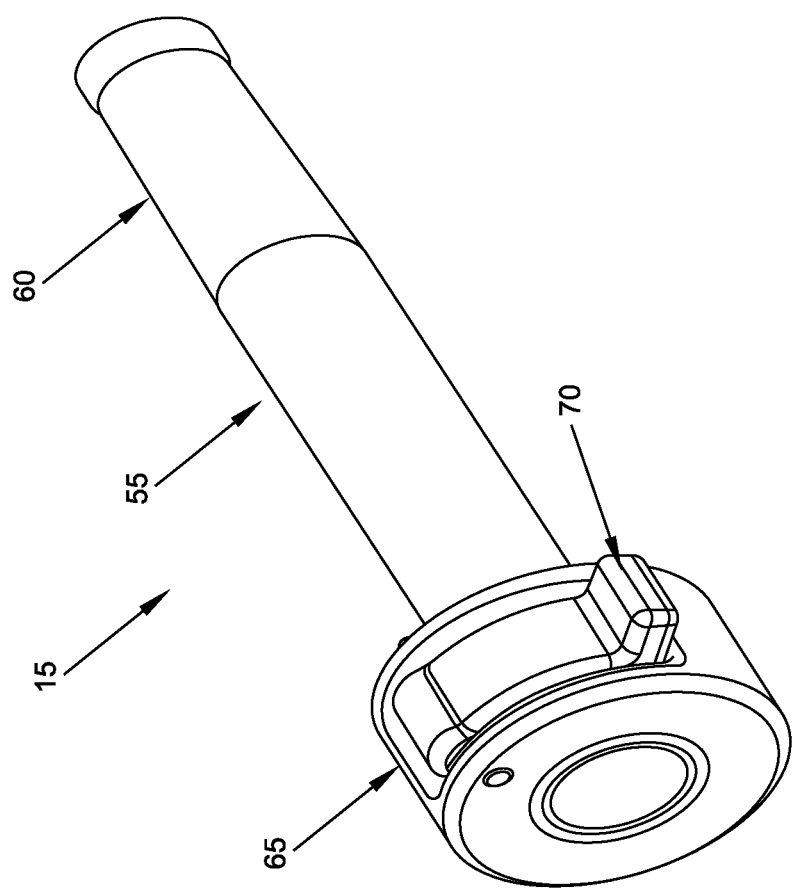
Figure 19:
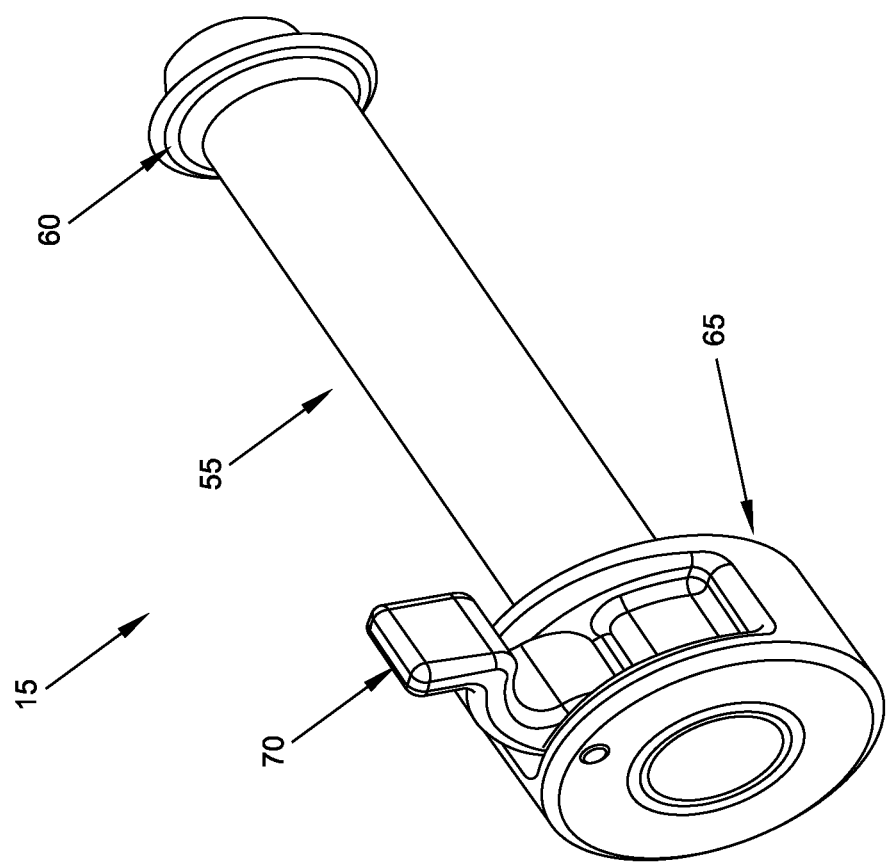

More particularly, and looking now at FIGS. 17A and 17B, cannula sub-assembly 10 generally comprises a hollow tube 20 having a distal end 25 and a proximal end 30 terminating in a proximal hub 35. Cannula sub-assembly 10 is of the type generally known in the art, in the sense that it includes a central lumen opening on distal end 25 and proximal hub 35, and may include a seal 40 for selectively sealing the central lumen and/or a luer lock 45 for introducing or removing fluid from the surgical site. Preferably cannula sub-assembly 10 includes a cannulated obturator 50 for selectively filling the lumen of hollow tube 20, e.g., when locking access cannula 5 is inserted into the body. Cannula sub-assembly has windows 47 formed therein (FIG. 17A) for receiving a finger of locking sub-assembly 15, which will hereinafter be discussed in further detail.

Locking sub-assembly 15 (FIGS. 18 and 19) comprises a sleeve 55 having an expandable collar 60 on its distal end, and a housing 65 which includes a locking lever 70 for expanding and retracting expandable collar 60. Locking sub-assembly 15 also comprises an internal finger 72 (not shown) for extending through a window 47 formed in cannula sub-assembly 10.

It should be appreciated that although locking access cannula 5 comprises two separate sub-assemblies, the two separate sub-assemblies may be joined during manufacture so as to create a single construction. At the time of manufacture, locking sub-assembly 15 is mounted onto cannula sub-assembly 10 so that finger 72 is aligned with window 47 (in order that the finger can thereafter be selectively moved through the window, as will hereinafter be discussed in further detail), and then locking sub-assembly 15 is secured onto cannula sub-assembly 10, e.g., by ultrasonic welding.

Figure 20:
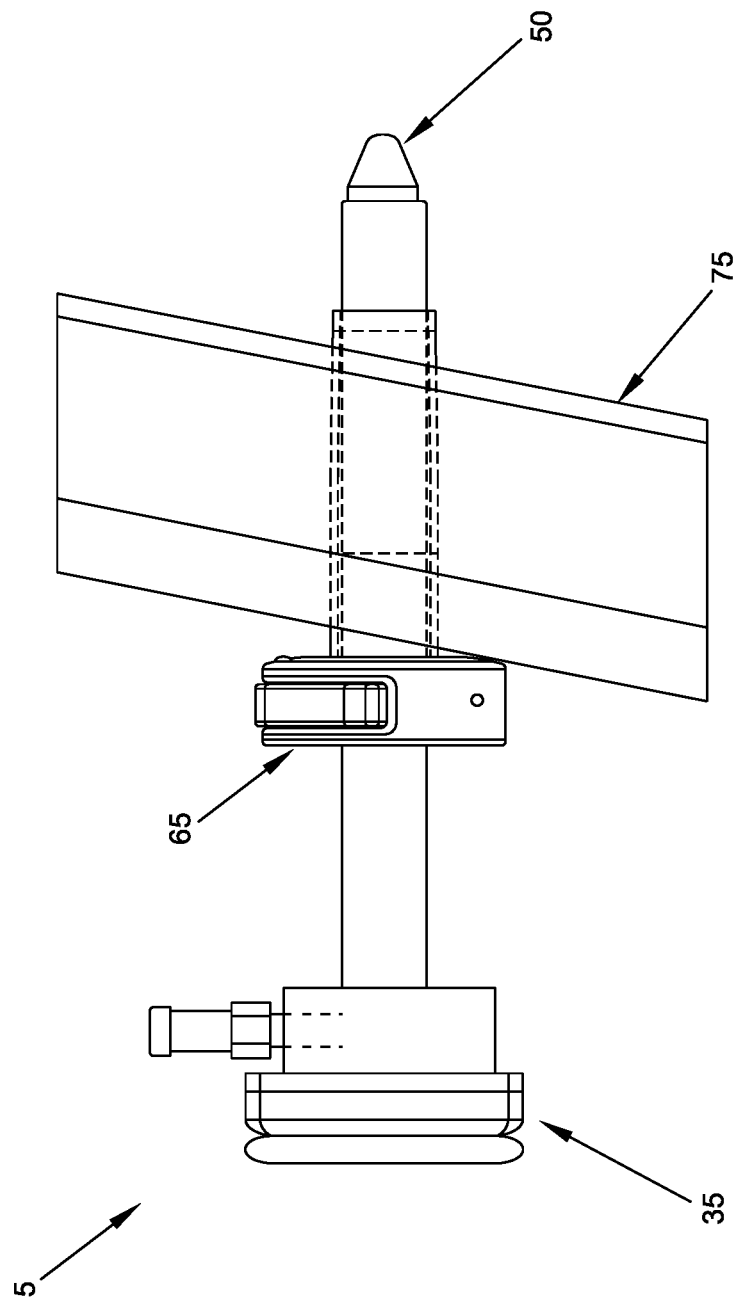
Figure 21:
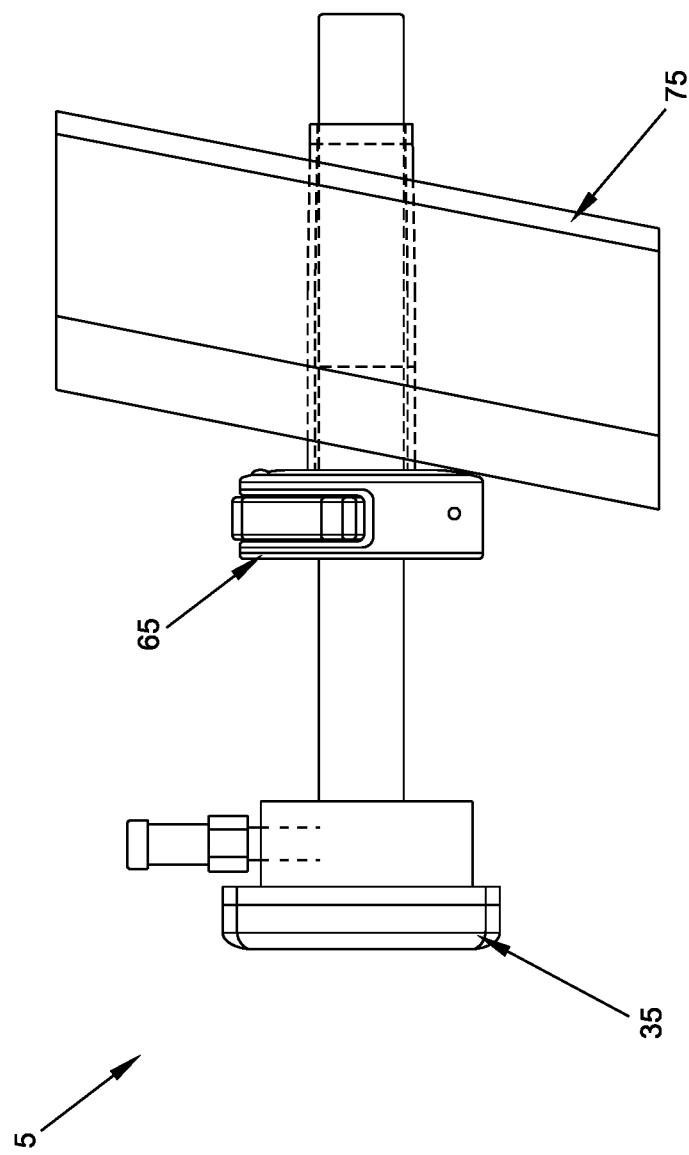
Figure 22:
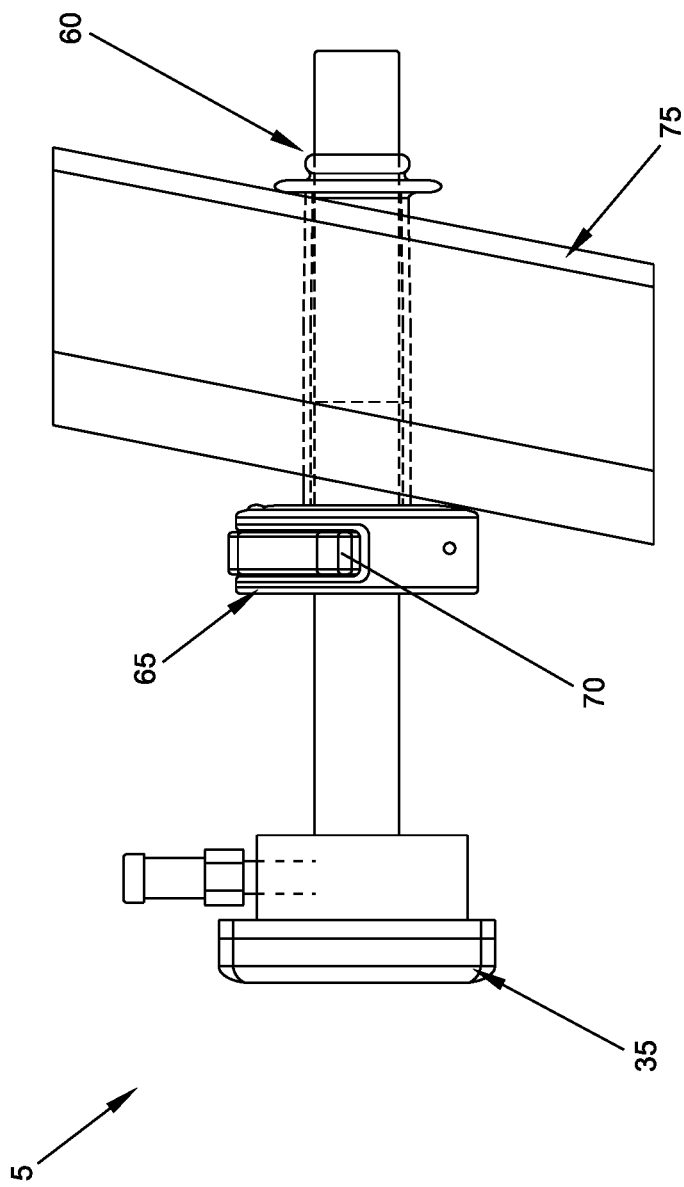

In use, and looking next at FIGS. 20-24, a guidewire or access needle is first passed through the skin, through the intervening tissue, and then into the hip joint. Next, locking access cannula 5, with obturator 50 in place, is passed coaxially over the guidewire (not shown), through the intervening tissue 75, and into the interior of the capsule of the hip (FIG. 20). Then obturator 50 is removed from the cannula and the guidewire is removed from the cannula (FIG. 21). Locking lever 70 is then actuated so as to enlarge expandable collar 60 on the distal end of locking sub-assembly 15. This causes expandable collar 60 to enlarge with the enlarged collar 60 being located on the joint side of the capsule. This helps hold the distal end of the cannula in place within the capsule (FIG. 22).

Thereafter, if desired, locking access cannula can then be positioned by the surgeon so that expandable collar 60 is pressed against the interior surface of the capsule, and the capsule can then be "tented" by pulling outwardly on the proximal end of the locking access cannula whereby to create additional workspace between the capsule and the hip joint.

Figure 23:
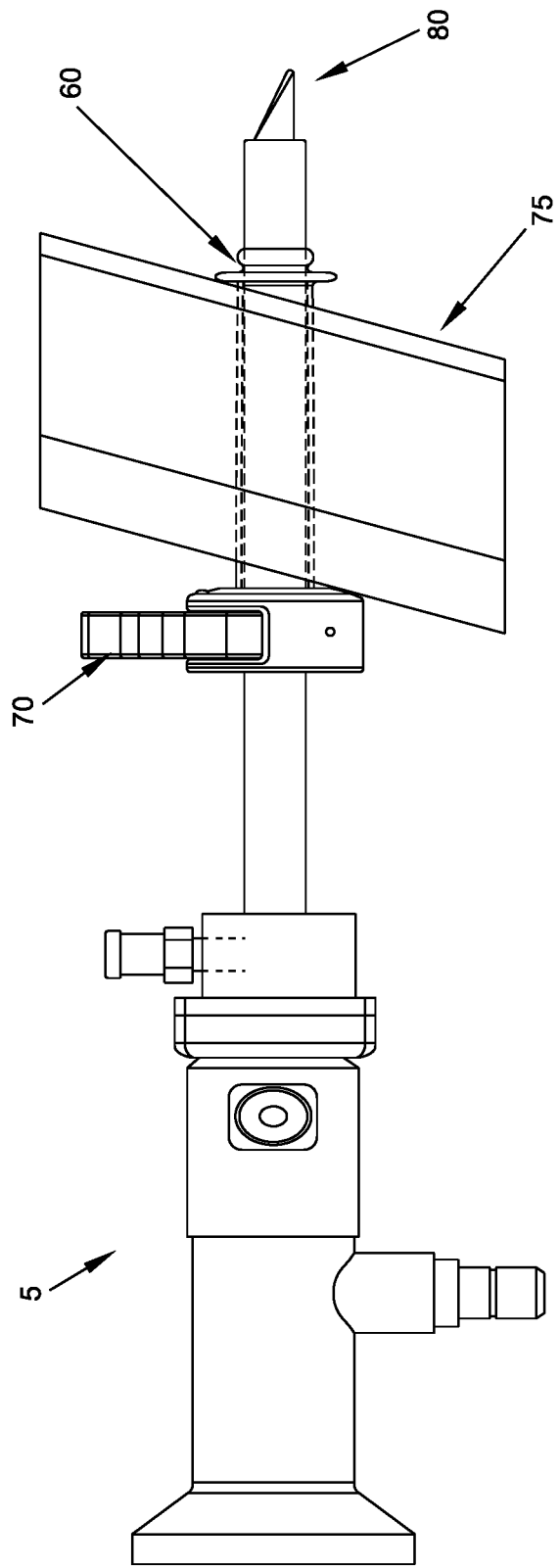
Figure 24:
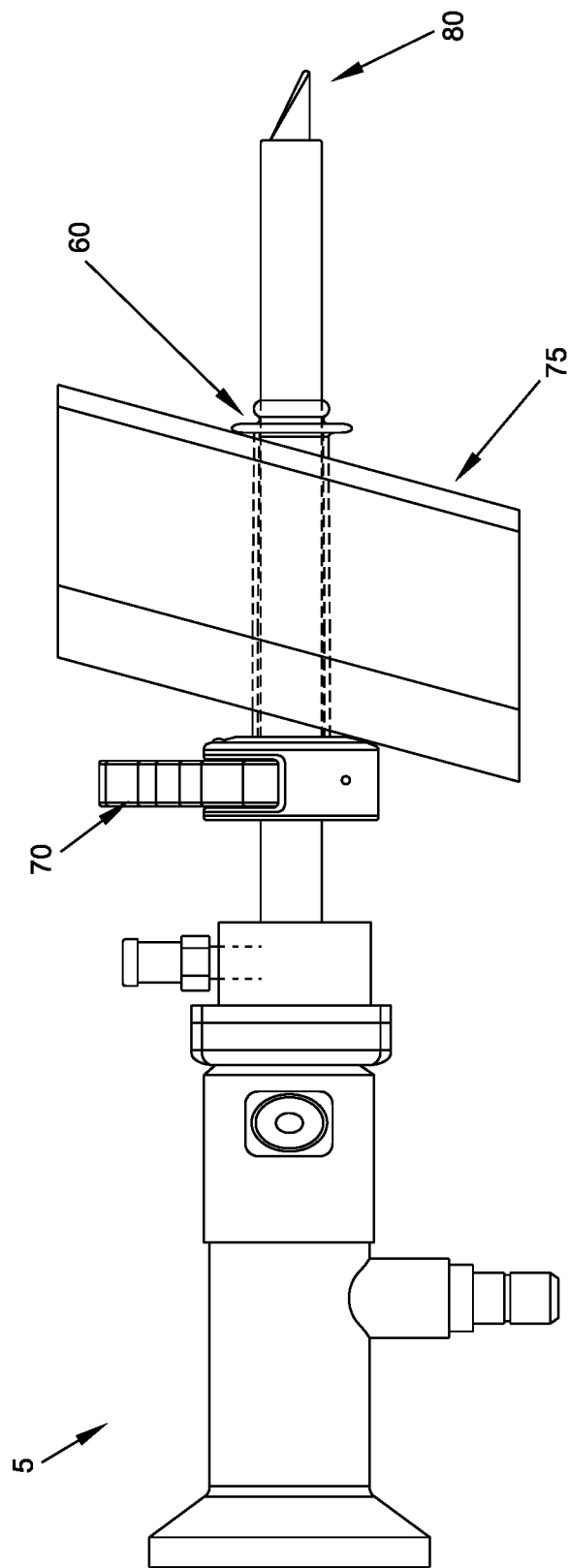

Locking lever 70 may be "un-locked" so as to withdraw finger 72 from window 47, so as to allow a scope or other instrument 80 to be introduced through the lumen of cannula sub-assembly 10 and down to the surgical site (FIG. 23). Locking lever 70 can then be actuated again so as to cause finger 72 to protrude through window 47 into the lumen of cannula sub-assembly 10 and thereby lock the scope or other instrument 80 to the inner cannula sub-assembly 10, and hence to locking access cannula 5.

It should be appreciated that although locking lever 70 may actuate both expandable collar 60 and finger 72, more preferably, separate locking levers 70 can be used to separately actuate expandable collar 60 and finger 72. Significantly, a surgeon can actuate a first lever to open expandable collar 60 and lock the distal end of the cannula within the capsule, and then be able to move the cannula so as to "tent" the tissue. In this embodiment of the present invention, a surgeon can then insert and/or otherwise move a scope within the locking access cannula and then actuate a second lever to lock the scope to the locking access cannula.

It should also be appreciated that expandable collar 60 may be expanded by other mechanisms well known in the art (e.g., fluid or air expansion, etc.).

In view of the foregoing, locking access cannula 5 can be used as both an access cannula for delivering scopes or other instruments to a surgical site, as well as used to create additional workspace in the hip joint during a procedure.

Access Cannula with Expansion Wheel Tensioner

In another preferred embodiment, the present invention is directed to a cannula that allows quick access to the interior of the hip joint while also providing an expansion wheel mechanism for creating additional workspace.

Looking next at FIGS. 25-27, there is shown a tensioning access cannula 100 formed in accordance with the present invention. Tensioning access cannula 100 generally comprises a hollow tube 105 having a distal end 110 terminating in capsule locking sleeve 115, and a proximal end 120 terminating in a proximal hub 125.

Tensioning access cannula 100 includes a central lumen opening on its distal end and may include a proximal seal for selectively sealing the central lumen and/or a proximal luer lock for introducing or removing fluid from the surgical site. Preferably tensioning access cannula includes a cannulated obturator (not shown) for selectively filling the lumen of hollow tube 105, e.g., when tensioning access cannula 100 is inserted into the body.

Hollow tube 105 is partially threaded along a portion T of its length and also comprises an expansion wheel tensioner 130 mounted thereon. It should be appreciated that expansion wheel tensioner 130 has a complementary thread to threaded portion T of hollow tube 105, so as to allow expansion wheel tensioner 130 to move laterally along threaded portion T of hollow tube 105.

Proximal hub 125 comprises an actuator 135 for expanding capsule locking sleeve 115.

In use, and looking next at FIGS. 26 and 27, a guidewire or access needle is first passed through the skin, through the intervening tissue, and then into the hip joint. Next, tensioning access cannula 100, with its obturator in place (not shown), is passed coaxially over the guidewire (not shown), through the intervening tissue 140, and to the interior of the capsule of the hip (FIG. 26). Then the obturator is removed from the cannula and the guidewire is removed from cannula. Actuator 135 is then actuated so as to expand capsule locking sleeve 115 so as to form a collar shape. Expansion wheel tensioner 130 is then tightened by the surgeon so as to shorten the distance between expansion wheel 130 and the enlarged capsule locking sleeve 115. This causes capsule C to be "tented" by the retracting enlarged capsule locking sleeve 115 (FIG. 27). Thus, tensioning access cannula 100 can be used to increase the workspace inside the hip joint, in the peripheral compartment.

By virtue of the fact that expansion wheel tensioner 130 is movably threaded on threaded portion T of hollow tube 105, it can be used to adjust the tension applied to the tissue during the procedure. This is important since during a lengthy procedure, the tissue tends to swell due to the retention of saline fluids applied to the surgical site. Thus, the provision of expansion wheel tensioner 130 allows a surgeon to adjust the tension applied to the tissue so as to accommodate for tissue swelling.

In addition, since the enlarged capsule locking sleeve 115 and expansion wheel tensioner 130 form a stable construct, the tissue can be maintained in its tented position without constant manual intervention. This "hands-free" operation can be extremely useful to the surgeon.

In view of the foregoing, tensioning access cannula 100 can be used as both an access cannula for delivering scopes or other instruments to a surgical site, as well as used to create additional workspace in the hip joint and to adjust tension applied to tissue during a procedure.

Capsule Retraction with an Anchor Attached to a Length of Suture

In another embodiment of the present invention, and looking now at FIGS. 28A-28E, an anchor 2000 attached to a length of suture S may be used to retract the capsule in order to create additional workspace in the hip joint. Anchor 2000 comprises a body 2005 which is attached at a center portion to a length of suture S. Body 2005 may be formed from a shape memory or super elastic material (e.g., nitinol) so that body 2005 may assume a first, folded configuration (FIGS. 28A and 28B) when body 2005 is in a stressed condition and a second, straight configuration (FIG. 28E) when body 2005 is in a non-stressed condition.

Figure 28F:
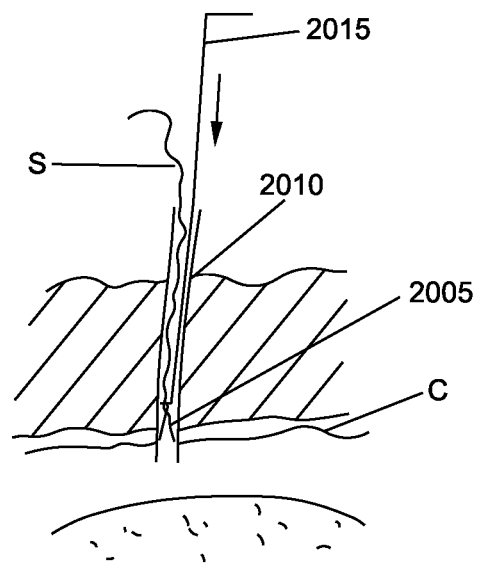
Figure 28G:
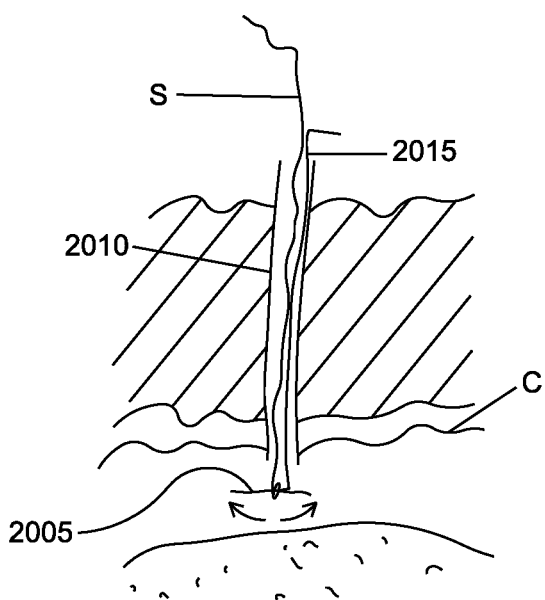
Figure 28H:
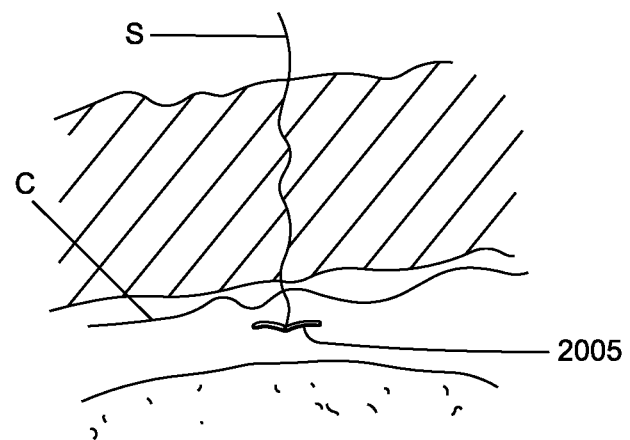
Figure 28I:
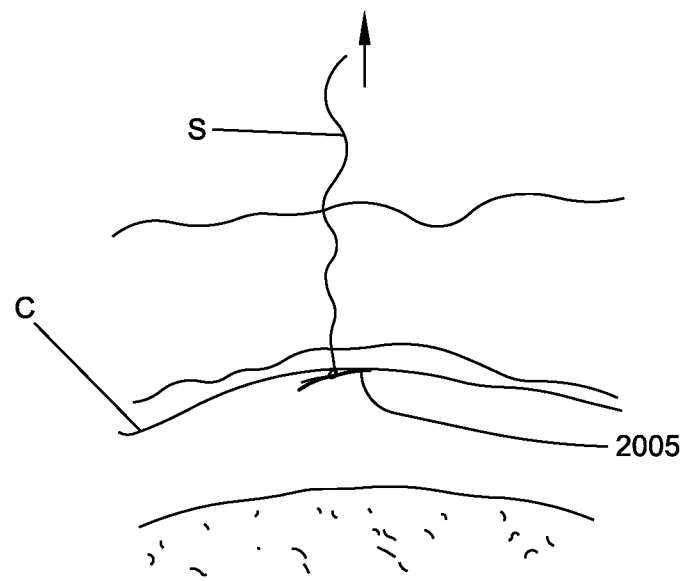

In use, and looking now at FIGS. 28F-28I, anchor 2000, with suture S attached, is folded in half and passed through a sheath 2010 which maintains body 2005 in its first, folded configuration. Sheath 2010 is then passed through capsule C so that the distal end of sheath 2010 is positioned within the interior of the joint (FIG. 28F). Using a push rod 2015, body 2005 is pushed through the distal end of sheath 2010, forcing body 2005 into its second, straight configuration (FIG. 28G). Sheath 2010 and push rod 2015 can now be removed from the joint (FIG. 28H) and suture S can be manipulated so as to position body 2005 against the interior surface of the capsule. The capsule can then be "tented" by pulling suture S proximally, whereby to create additional workspace between the capsule and the hip joint (FIG. 28I).

Capsule Retraction with a Rod Having a Pivoting Distal End

In another embodiment of the invention, and looking now at FIG. 29 and FIGS. 29A-D, a rod 3000 may be used to retract capsule C in order to create additional workspace in the hip joint. Rod 3000 comprises an elongated shaft 3005 having a distal end 3010 with a pivot point 3020 axially spaced from distal end 3010. Preferably, distal end 3010 comprises a sharpened distal end so that rod 3000 may be passed directly through the capsule. However, if desired, rod 3000 (with or without a sharpened distal tip) may also be passed through a cannula or sheath positioned against the capsule. Rod 3000 also comprises a pull wire 3025 (FIG. 29C) extending through the center of elongated shaft 3005 which may be pushed or pulled in order to pivot distal end 3010 (at pivot point 3020) from a first position in which distal end 3010 is substantially aligned with the longitudinal axis of elongated shaft 3005 (FIGS. 29A-C) to a second position in which distal end 3010 extends at an angle (e.g., perpendicularly) to the longitudinal axis of elongated shaft 3005 (FIGS. 29 and 29D).

In use, and looking now at FIGS. 29E and 29F, pull wire 3025 (not shown in FIGS. 29E and 29F, but shown in FIGS. 29C and 29D) is pulled proximally so as to position distal end 3010 in its first position. Rod 3000 is then inserted percutaneously directly through capsule C. After distal end 3010 of elongated shaft 3005 passes through capsule C (FIG. 29E), pull wire 3025 may be pushed distally in order to cause distal end 3010 to pivot from its first position to its second position, with distal end 3010 positioned against the interior surface of capsule C (FIG. 29F). Elongated shaft 3005 may then be pulled proximally so as to "tent" capsule C and create additional workspace between the capsule and the head of the femur. After a surgeon no longer needs access to the hip joint, pull wire 3025 may be pulled proximally in order to cause distal end 3010 to pivot back to its first position and rod 3000 may be removed from the joint.

Capsule Retraction with a Rod having a Projection

Looking now at FIG. 30, a rod 4000 may be used to retract capsule C in order to create additional workspace in the hip joint. Rod 4000 comprises an elongated shaft 4005 having a distal end 4010 with a pivot point 4020 axially spaced from distal end 4010. A projection 4025 is attached to elongated shaft 4005 at pivot point 4020. Rod 4000 also comprises a length of wire having two portions 4030 and 4035 extending along the longitudinal axis of elongated shaft 4005 and configured to cause projection 4025 to move from a first position which is substantially aligned with elongated rod 4005 to a second position in which projection 4025 extends at an angle to the longitudinal axis of elongated shaft 4005.

In use, and looking now at FIGS. 30A and 30B, the wire is manipulated so as to position projection 4025 in its first position. Rod 4000 may then be passed directly through the capsule, or through a cannula or sheath 4040 positioned through the capsule. After distal end 4010 of elongated shaft 4005 passes through capsule C (FIG. 30A), portion 4035 of the wire may be pulled proximally in order to cause projection 4025 to move from its first position to its second position (FIG. 30B). Rod 4000 may now be manipulated so as to position projection 4025 against the neck of the femur. When projection 4025 (extending at an angle to shaft 4005) is positioned against the neck of the femur, the projection pushes against the neck of the femur, which causes capsule C to stretch and retract between the neck of the femur and the interior surface of the capsule, thereby creating additional workspace within the joint. After a surgeon no longer needs access to the hip joint, portion 4030 of the wire may be pulled proximally in order to cause projection 4025 to rotate back to its first position and rod 4000 may be removed from the joint.

Capsule Retraction with a Rod Having a Corkscrew

In another embodiment of the invention, and looking now at FIG. 31, a rod 5000 having a corkscrew may be used to retract capsule C in order to create additional workspace in the hip joint. Rod 5000 comprises a body 5005 having a corkscrew 5010 at its distal end.

In use, and looking now at FIGS. 31A-31C, rod 5000 may be passed through a cannula or needle 5015 positioned on the outside surface of capsule C, so that corkscrew 5010 of body 5005 is also positioned on the outside surface of capsule C (FIG. 31A). Body 5005 is then rotated so as to cause corkscrew 5010 to advance into capsule C, thereby engaging capsule C (FIG. 31B). Rod 5000 may then be pulled proximally so as to "tent" capsule C away from the joint, whereby to create additional workspace in the hip joint (FIG. 31C).

Capsule Retraction with Suture

In another embodiment of the invention, a device and method are provided which may be used when the capsule is cut open, e.g., in a manner shown in FIG. 33, in order to create additional workspace within the hip joint.

Looking now at FIG. 32, a device for creating additional workspace within the joint is provided. The device shown in FIG. 32 comprises a length of suture S with a T-bar anchor 6000a secured to one end of the length of suture S and a T-bar anchor 6000b secured to the other end of the length of suture S.

In an alternative form of the present invention, T-bar anchor 6000b is omitted from the device. In this embodiment, the device comprises a length of suture S having a T-bar anchor 6000a secured to one end of the length of suture 5, with the other end of the length of suture remaining free.

The device shown in FIG. 32, and the device omitting T-bar anchor 6000b, may be used in the following manner to create additional workspace within the hip joint.

Looking first at FIG. 33, a T-shaped cut (or any other shaped cut which creates two edges in the capsule) is made in capsule C in order to create two flaps, F1 and F2, and expose both the head of the femur and the acetabular cup.

Looking now at FIGS. 34-38B, a push rod 6005 is used to load suture 5, with at least one T-bar anchor extending therefrom, through a needle 6010 (FIG. 34). Needle 6010 is passed percutaneously through the skin, into the hip joint and through flap F1 of capsule C. A second needle 6010, with a suture S and at least one T-bar anchor loaded within the needle, is passed percutaneously through the skin, into the hip joint and through flap F2 of capsule C (FIG. 35). Push rod 6005 is used to push T-bar anchor 6000a and suture S through needle 6010 so that T-bar anchor 6000a extends out of the distal end of needle 6010 and into the interior of the capsule, leaving T-bar anchor 6000a located within the interior of the capsule and a length of suture extending to the exterior of the capsule (FIGS. 36A and 36B).

Looking next at FIG. 37, both push rod 6005 and needle 6010 are removed from capsule C, and suture S is pulled proximally so as to lock T-bar anchor 6000a on the underside of capsule C.

The two ends of suture S extending from T-bar anchors 6000a may now be pulled proximally so as to retract flaps F1 and F2 of capsule C (FIGS. 38A and 38B). This permits a surgeon improved access to the neck of the femur normally covered by the capsule.

It is important to note that the T-shaped cut in the capsule can also be made in the capsule after T-bar anchors 6000a have been locked on the underside of capsule C rather than before the T-bar anchors are locked on the underside of the capsule, as described above. Additionally, T-bar anchors 6000a could be used in capsule C where no cut is made; in other words, T-bar anchors 6000a are placed in a region of the capsule where it is desired to tent, or retract, the capsule.

Once the necessary arthroscopic procedures are completed, T-bar anchors 6000a may be removed from the joint as follows.

Figure 39:
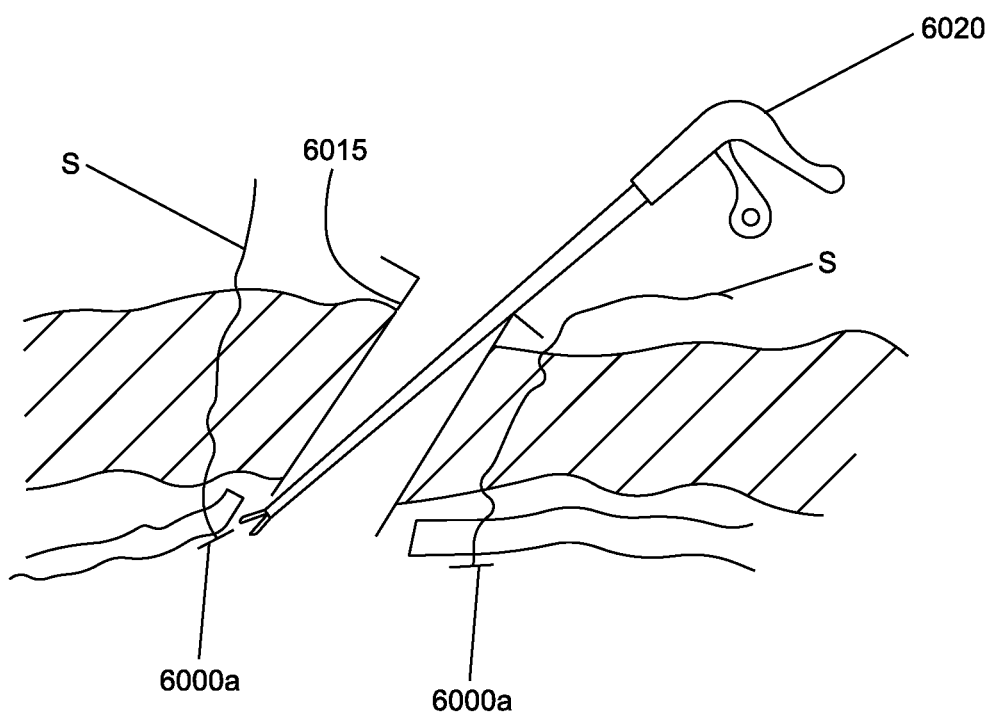

Looking now at FIG. 39, a cannula 6015 may be inserted into the capsule and grasping forceps 6020 may be passed through the cannula to grasp each T-bar anchor 6000a from the underside of capsule C (FIG. 39). Each T-bar anchor 6000a, with suture S attached, is then pulled proximally from the underside of capsule C until all the suture is removed from the joint space through the cannula. It is important to note that, when T-bar anchor 6000b is attached to the other end of the length of suture, T-bar anchor 6000b may be cut from the end of the suture prior to pulling T-bar anchor 6000a from the underside of capsule C so that the other end of the length of suture is free to slide out of the joint (in this example, from the skin to the capsule through the adjoining tissue structures).

Figure 40:
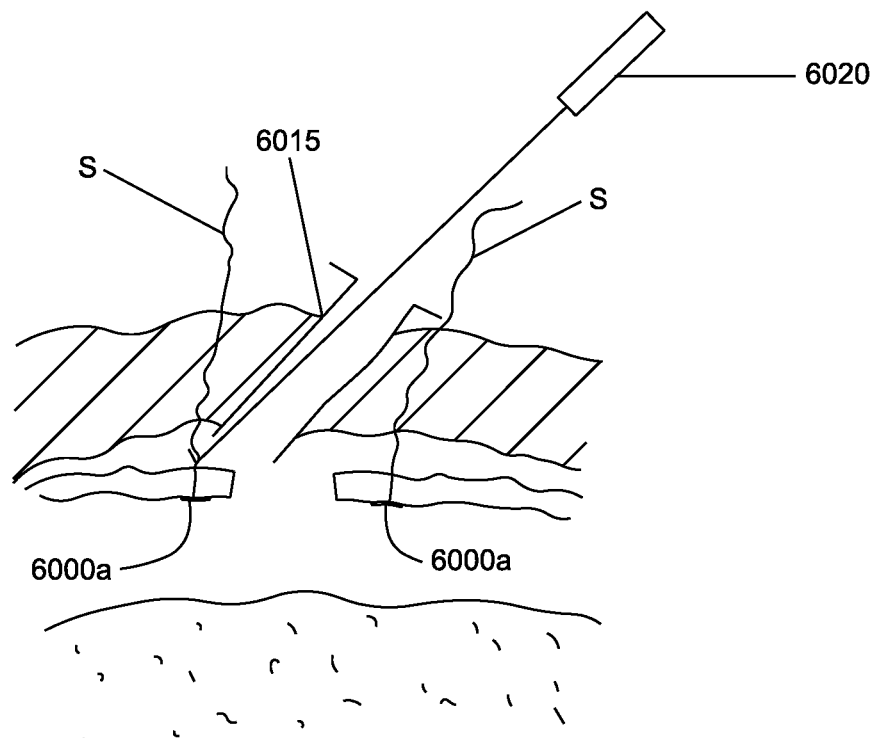
Figure 41:
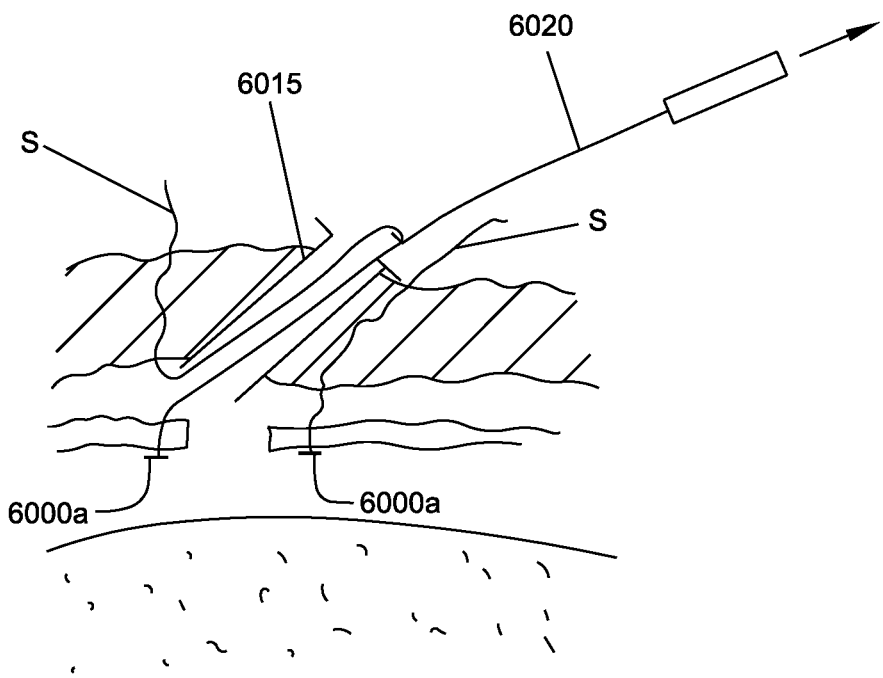
Figure 42:
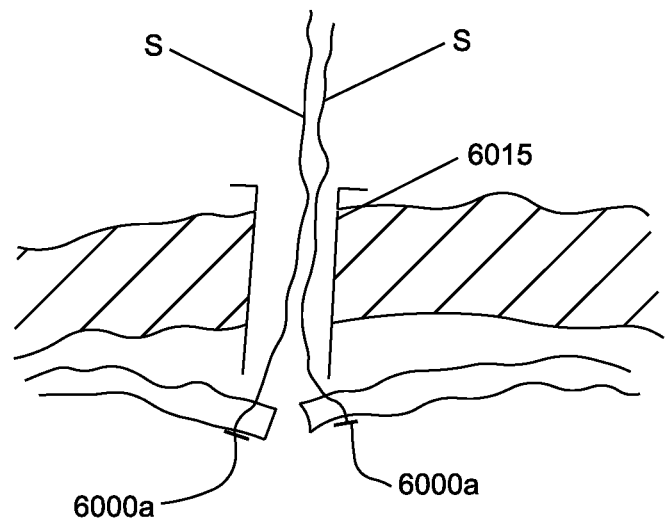
Figure 43:
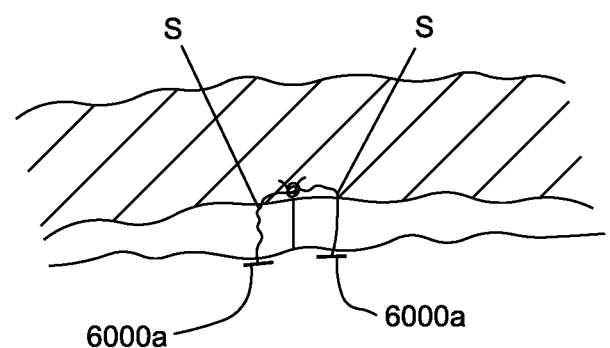
Figure 44:
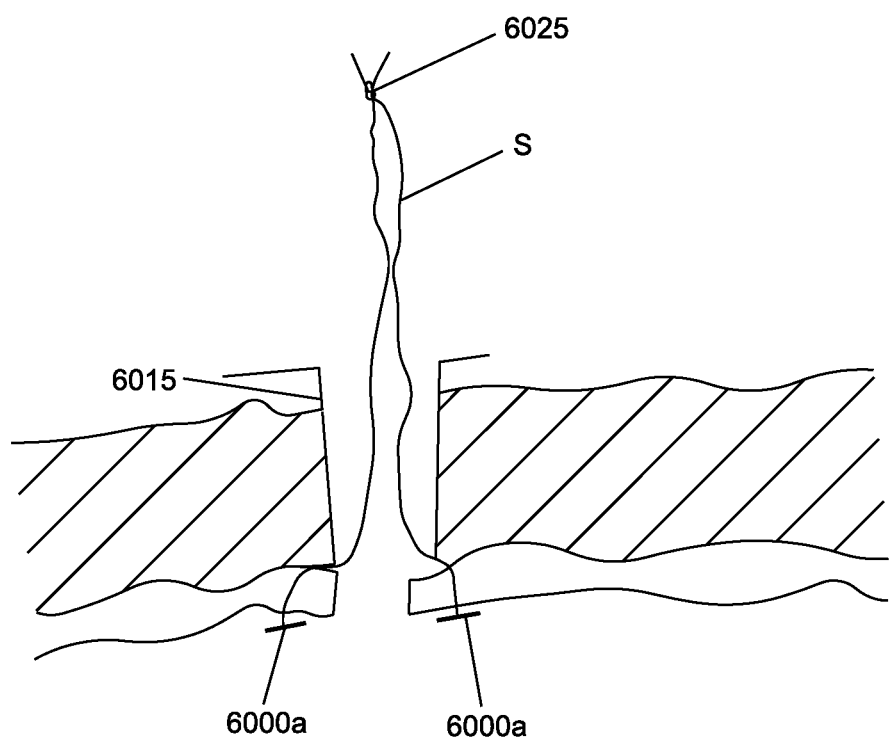

Instead of removing T-bar anchors 6000a from the joint, it may also be desirable to close capsule C using T-bar anchors 6000a, with T-bar anchors 6000a remaining in the joint after the capsule has been closed. In this embodiment, and looking now at FIGS. 40-43, a cannula 6015 may be inserted into the capsule and a grasping or hooking instrument 6020 may be passed through the cannula to grasp or hook the portion of the suture positioned on the outside of capsule C (FIG. 40). Each leg of the suture is passed up through the cannula (FIG. 41) until two free ends of suture extend from the capsule (FIG. 42). The two free ends of the suture extending from the capsule may then be tied off (e.g., using a half hitch or other non-sliding knot well known to those skilled in the art) so as to re-stitch and secure the capsule (FIG. 43). If desired, suture S and T-bar anchors 6000a may be formed from an absorbable material so that they dissolve over time.

In another embodiment, it may be desirable to remove T-bar anchors 6000a from the joint, and close the capsule, leaving only suture S in the joint. In this embodiment, and looking now at FIG. 44, a cannula 6015 may be inserted into the capsule and a grasping or hooking instrument 6020 may be passed through the cannula to grasp or hook the portion of the suture positioned on the outside of capsule C. Each leg of the suture is passed up through the cannula until two free ends of suture extend from the capsule. Once the free ends of suture S have been passed up through the cannula, a knot 6025 is formed on the free ends of suture S. Subsequently, a grasping instrument may be used to grasp each T-bar anchor 6000a from the underside of capsule C (not shown). Each T-bar anchor 6000a, with suture S attached, is then pulled proximally from the underside of capsule C until T-bar anchors 6000a are removed from the joint space through the cannula. As the T-bar anchors are removed from the joint space, knot 6025 is positioned along the capsule. The ends of the suture with T-bar anchors 6000a may then be tied off (e.g., using a half hitch or other non-sliding knot well known to those skilled in the art) so as to re-stitch and secure the capsule (not shown). If desired, suture S may be formed from an absorbable material so that the sutures dissolve over time.

In still another embodiment of the present invention, it may be desirable to close capsule C using T-bar anchors 6000a and 6000b, with T-bar anchors 6000b remaining in the joint after the capsule has been closed. In this embodiment, and looking now at FIGS. 45-48, a cannula may be inserted into the capsule and grasping forceps may be passed through the cannula to grasp each T-bar anchor 6000a from the underside of capsule C (FIG. 45). Each T-bar anchor 6000a, with suture S attached, is then pulled proximally from the underside of capsule C (FIG. 46) until T-bar anchors 6000b are resting on the outside of capsule C (FIG. 47A-47C). The free ends of the suture extending from the capsule may then be tied off (e.g., using a half hitch or other non-sliding knot well known to those skilled in the art) so as to re-stitch and secure the capsule (FIG. 48). If desired, suture S may be formed from an absorbable material so that the sutures dissolve over time In another form of the present invention, and looking at FIG. 49, a length of suture may be used to retract capsule C, and a cannula 7000 having a projection 7005 may be used to secure the suture so as to maintain the capsule in the retracted position while the necessary arthroscopic procedures are completed.

In use, a T-shaped cut (or any other shaped cut which creates two edges in the capsule) is made in capsule C so as to create two flaps, F1 and F2, and expose both the head of the femur and the acetabular cup.

A push rod may be used to load suture S through a needle (not shown). The needle is passed through cannula 7000 and through flap F1 of capsule C so that two free ends of suture S extend from flap F1. A second needle, with suture S loaded therein, is passed through cannula 7000b and through flap F2 of capsule C so that two free ends of suture S extend from flap F2. Each of the two free ends of suture S may now be pulled proximally so as to retract flaps F1 and F2 of capsule C. In order to permit a surgeon to better access the hip joint, each of the two free ends of suture extending from the flaps can be tied around projection 7005 in order to maintain the flaps in their retracted position.

Projection 7005 may comprise a post on which to wrap suture S. Post may include a narrow slit to capture a portion of suture S. The slit is narrower than the width of suture S so that the slit squeezes the suture to provide a gripping force. The slit may be formed out of an elastomeric material. Alternatively, projection 7005 may comprise a clamp into which suture S is secured. Clamp may be activated manually or with a spring.

It is important to note that a length of suture may also be used to retract capsule C, and cannula 7000 with projection 7005 may be used to secure the suture so as to maintain the capsule in the retracted position even when a cut has not been made in the capsule.

Capsule Retraction with a Rod Having a Hook

Looking now at FIG. 50, a rod 8000 having a hook 8005 may be used to retract capsule C after the capsule has been cut open, e.g., in a manner shown in FIG. 33 (or any other shaped cut which creates two edges in the capsule), in order to create additional workspace in the hip joint. Rod 8000 comprises a body 8005 having a hook 8010 at its distal end.

In use, a T-shaped cut is made in capsule C so as to create two flaps, and expose both the neck and/or head of the femur and/or the acetabular cup. Hook 8010 of rod 8000 may be positioned underneath a flap of the cut capsule. Rod 8000 may then be pulled proximally so as to pierce capsule C and retract capsule C away from the joint.

Use of the Present Method and Apparatus for Other Joints, Etc.

It should be appreciated that the present systems and methods disclosed herein may also be used for increasing the workspace in joints in addition to the hip joint, e.g., the present methods and systems may be used to increase the workspace in the knee joint, the shoulder joint, etc. Furthermore, the present methods and systems may also be used to increase workspace in other interior bodily spaces, e.g., the abdomen, the bladder, regions around the spine, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

In the claims:

1. A method of repositioning tissue disposed within the interior of a body, the method comprising:
    providing an elongated shaft having a proximal end and a distal end, the distal end comprising a tissue-penetrating element, wherein the tissue-penetrating element comprises a corkscrew;
    forming a cut in the tissue so as to create a first flap of tissue on one side of the cut in the tissue and a second flap of tissue on a second side of the cut in the tissue;
    passing the elongated shaft through the skin so that the distal end of the elongated shaft is positioned on one of the first and second flaps of tissue to be repositioned;
    rotating the elongated shaft so as to advance at least a portion of the corkscrew into the flap of tissue to be repositioned; and
    moving the elongated shaft so as to reposition the flap of tissue.

2. The method of claim 1 wherein repositioning the flap of tissue comprises retracting the flap of tissue by moving the elongated shaft proximally.

3. The method of claim 1 wherein repositioning the flap of tissue comprises improving access to the interior of the body.

4. The method of claim 1 wherein passing the elongated shaft through the skin comprises passing the elongated shaft directly through the skin.

5. The method of claim 1 wherein passing the elongated shaft through the skin comprises passing the elongated shaft through a hollow access lumen.

6. The method of claim 5 wherein the hollow access lumen comprises one from the group consisting of a hollow needle and an access cannula.

7. The method of claim 1 wherein the flap of tissue is repositioned within a joint.

8. The method of claim 7 wherein repositioning the flap of tissue creates additional workspace within the joint.

9. The method of claim 7 further comprising performing an arthroscopic procedure within the joint while the flap of tissue is repositioned.

10. The method of claim 1 wherein the tissue is the capsule of a joint.

11. The method of claim 1 wherein the corkscrew comprises a tissue penetrating tip.

12. The method of claim 1 wherein the elongated shaft is rigid.

13. A method of repositioning tissue disposed within the interior of a body, the method comprising:
    providing an elongated shaft having a proximal end and a distal end, the distal end comprising a tissue-penetrating element, wherein the tissue-penetrating element comprises a corkscrew;
    passing the elongated shaft through the skin so that the distal end of the elongated shaft is positioned on the tissue to be repositioned;
    rotating the elongated shaft so as to advance at least a portion of the corkscrew into the tissue to be repositioned; and
    moving the elongated shaft so as to reposition the tissue;
    wherein the tissue is repositioned within a joint.

14. The method of claim 13 wherein repositioning the tissue comprises retracting the tissue by moving the elongated shaft proximally.

15. The method of claim 13 wherein repositioning the tissue comprises improving access to the interior of the body.

16. The method of claim 13 wherein passing the elongated shaft through the skin comprises passing the elongated shaft directly through the skin.

17. The method of claim 13 wherein passing the elongated shaft through the skin comprises passing the elongated shaft through a hollow access lumen.

18. The method of claim 17 wherein the hollow access lumen comprises one from the group consisting of a hollow needle and an access cannula.

19. The method of claim 13 further comprising forming a cut in the tissue so as to create two sides of the tissue extending from the cut in the tissue.

20. The method of claim 13 wherein repositioning the tissue creates additional workspace within the joint.

21. The method of claim 13 further comprising performing an arthroscopic procedure within the joint while the tissue is repositioned.

22. The method of claim 13 wherein the tissue is the capsule of a joint.

23. The method of claim 13 wherein the corkscrew comprises a tissue penetrating tip.

24. The method of claim 13 wherein the elongated shaft is rigid.

* * * * *